US012575830B2

(12) United States Patent
Shelton, IV et al.

(10) Patent No.: US 12,575,830 B2
(45) Date of Patent: *Mar. 17, 2026

(54) SURGICAL STAPLING SYSTEMS INCLUDING A TIMER FOR THE FIRING MOTION

(71) Applicant: Cilag GmbH International, Zug (CH)

(72) Inventors: Frederick E. Shelton, IV, Hillsboro, OH (US); Jeffrey S. Swayze, West Chester, OH (US); James R. Giordano, Milford, OH (US)

(73) Assignee: Cilag GmbH Semiconductor, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/932,125

(22) Filed: Oct. 30, 2024

(65) Prior Publication Data

US 2025/0120718 A1 Apr. 17, 2025

Related U.S. Application Data

(63) Continuation of application No. 18/368,236, filed on Sep. 14, 2023, now Pat. No. 12,161,329, which is a
(Continued)

(51) Int. Cl.
*A61B 34/30* (2016.01)
*A61B 17/068* (2006.01)
(Continued)

(52) U.S. Cl.
CPC ...... *A61B 17/07207* (2013.01); *A61B 17/068* (2013.01); *A61B 34/30* (2016.02);
(Continued)

(58) Field of Classification Search
CPC ......... A61B 34/30; A61B 34/71; A61B 34/76; A61B 34/068; A61B 17/128;
(Continued)

(56) References Cited

U.S. PATENT DOCUMENTS

| | | | |
|---|---|---|---|
| 4,106,620 | A | 8/1978 | Brimmer et al. |
| 4,652,820 | A | 3/1987 | Maresca |

(Continued)

FOREIGN PATENT DOCUMENTS

| | | |
|---|---|---|
| CA | 2851239 A1 | 11/2007 |
| CN | 1163558 A | 10/1997 |

(Continued)

OTHER PUBLICATIONS

IPR2018-00938_Notice_of_Refund_07_03_2019.
(Continued)

*Primary Examiner* — Nathaniel C Chukwurah
(74) *Attorney, Agent, or Firm* — Lempia Summerfield Katz LLC

(57) ABSTRACT

Surgical instruments and/or fastener apparatuses comprising an end effector with a pair of jaws pivoted at a proximal end thereof and movable between an open and closed position. At least one of the jaws may comprise a channel for receiving a cartridge containing a plurality of surgical fasteners. Also, an electrically powered actuator may be for deploying the surgical fasteners and may comprise a power source and a motor. An activation mechanism may be attached to the handle to move the pair of jaws from the open to the closed position and to activate the actuator. A lockout mechanism may be configured to permit current to flow from the power source to the motor when the pair of jaws is in the closed position and to prevent current from flowing to the power source to the motor when the pair of jaws is in the open position.

20 Claims, 69 Drawing Sheets

Related U.S. Application Data continuation of application No. 17/208,296, filed on Mar. 22, 2021, now Pat. No. 11,793,518, which is a continuation of application No. 16/906,397, filed on Jun. 19, 2020, now Pat. No. 10,952,728, which is a continuation of application No. 16/420,870, filed on May 23, 2019, now Pat. No. 11,051,813, which is a continuation of application No. 15/864,922, filed on Jan. 8, 2018, now Pat. No. 10,675,028, which is a continuation of application No. 13/796,996, filed on Mar. 12, 2013, now Pat. No. 9,861,359.

(51) Int. Cl.

| | |
|---|---|
| *A61B 17/072* | (2006.01) |
| *A61B 34/00* | (2016.01) |
| *A61B 17/00* | (2006.01) |
| *A61B 17/115* | (2006.01) |
| *A61B 17/29* | (2006.01) |
| *A61B 90/00* | (2016.01) |
| *A61B 90/30* | (2016.01) |

(52) U.S. Cl.
CPC .............. *A61B 34/71* (2016.02); *A61B 34/76* (2016.02); *A61B 2017/00017* (2013.01); *A61B 2017/00199* (2013.01); *A61B 2017/00221* (2013.01); *A61B 2017/00371* (2013.01); *A61B 2017/00398* (2013.01); *A61B 2017/00402* (2013.01); *A61B 2017/00685* (2013.01); *A61B 2017/00734* (2013.01); *A61B 17/072* (2013.01); *A61B 2017/07214* (2013.01); *A61B 2017/0725* (2013.01); *A61B 2017/07278* (2013.01); *A61B 2017/07285* (2013.01); *A61B 17/115* (2013.01); *A61B 2017/2943* (2013.01); *A61B 2090/064* (2016.02); *A61B 2090/065* (2016.02); *A61B 2090/0803* (2016.02); *A61B 2090/0811* (2016.02); *A61B 90/30* (2016.02)

(58) Field of Classification Search
CPC .............. A61B 17/115; A61B 17/0686; A61B 17/07207; A61B 90/06; A61B 34/10; A61B 17/072; A61B 17/068; A61B 17/1155; A61B 2090/061; A61B 2017/00039; A61B 2017/00119; A61B 2017/07214; A61B 2090/065; A61B 2090/0811; A61B 2017/00022; A61B 17/29; A61B 2017/00106

See application file for complete search history.

(56) References Cited

U.S. PATENT DOCUMENTS

| | | | |
|---|---|---|---|
| 5,307,976 | A | 5/1994 | Olson et al. |
| 5,330,487 | A | 7/1994 | Thornton et al. |
| 5,361,902 | A | 11/1994 | Abidin et al. |
| 5,383,880 | A | 1/1995 | Hooven |
| 5,395,033 | A | 3/1995 | Byrne et al. |
| 5,405,073 | A | 4/1995 | Porter |
| 5,465,894 | A | 11/1995 | Clark et al. |
| 5,465,895 | A | 11/1995 | Knodel et al. |
| 5,518,163 | A | 5/1996 | Hooven |
| 5,535,937 | A | 7/1996 | Boiarski et al. |
| 5,653,374 | A | 8/1997 | Young et al. |
| 5,667,517 | A | 9/1997 | Hooven |
| 5,688,270 | A | 11/1997 | Yates et al. |
| 5,709,680 | A | 1/1998 | Yates et al. |
| 5,904,702 | A | 5/1999 | Ek et al. |
| 5,931,853 | A | 8/1999 | McEwen et al. |
| 5,954,259 | A | 9/1999 | Viola et al. |
| 6,024,741 | A | 2/2000 | Williamson, IV et al. |
| 6,132,368 | A | 10/2000 | Cooper |

| | | | |
|---|---|---|---|
| 6,231,565 | B1 | 5/2001 | Tovey et al. |
| 6,331,181 | B1 | 12/2001 | Tierney et al. |
| 6,443,973 | B1 | 9/2002 | Whitman |
| 6,491,701 | B2 | 12/2002 | Tierney et al. |
| 6,646,307 | B1 | 11/2003 | Yu et al. |
| 6,670,806 | B2 | 12/2003 | Wendt et al. |
| 6,716,223 | B2 | 4/2004 | Leopold et al. |
| 6,783,524 | B2 | 8/2004 | Anderson et al. |
| 6,786,382 | B1 | 9/2004 | Hoffman |
| 6,908,472 | B2 | 6/2005 | Wiener et al. |
| 6,964,363 | B2 | 11/2005 | Wales et al. |
| 6,978,921 | B2 | 12/2005 | Shelton, IV et al. |
| 6,981,628 | B2 | 1/2006 | Wales |
| 7,044,352 | B2 | 5/2006 | Shelton, IV et al. |
| 7,055,731 | B2 | 6/2006 | Shelton, IV et al. |
| 7,077,856 | B2 | 7/2006 | Whitman |
| 7,083,075 | B2 | 8/2006 | Swayze et al. |
| 7,111,769 | B2 | 9/2006 | Wales et al. |
| 7,119,534 | B2 | 10/2006 | Butzmann |
| 7,143,923 | B2 | 12/2006 | Shelton, IV et al. |
| 7,380,696 | B2 | 6/2008 | Shelton, IV et al. |
| 7,386,730 | B2 | 6/2008 | Uchikubo |
| 7,407,078 | B2 | 8/2008 | Shelton, IV et al. |
| 7,416,101 | B2 | 8/2008 | Shelton, IV et al. |
| 7,422,139 | B2 | 9/2008 | Shelton, IV et al. |
| 7,461,767 | B2 | 12/2008 | Viola et al. |
| 7,464,846 | B2 | 12/2008 | Shelton, IV et al. |
| 7,464,847 | B2 | 12/2008 | Viola et al. |
| 7,464,849 | B2 | 12/2008 | Shelton, IV et al. |
| 7,467,740 | B2 | 12/2008 | Shelton, IV et al. |
| 7,494,501 | B2 | 2/2009 | Ahlberg et al. |
| 7,559,452 | B2 | 7/2009 | Wales et al. |
| 7,568,603 | B2 | 8/2009 | Shelton, IV et al. |
| 7,604,118 | B2 | 10/2009 | Iio et al. |
| 7,607,557 | B2 | 10/2009 | Shelton, IV et al. |
| 7,644,848 | B2 | 1/2010 | Swayze et al. |
| 7,670,334 | B2 | 3/2010 | Hueil et al. |
| 7,673,780 | B2 | 3/2010 | Shelton, IV et al. |
| 7,673,783 | B2 | 3/2010 | Morgan et al. |
| 7,695,485 | B2 | 4/2010 | Whitman et al. |
| 7,717,312 | B2 | 5/2010 | Beetel |
| 7,721,931 | B2 | 5/2010 | Shelton, IV et al. |
| 7,731,072 | B2 | 6/2010 | Timm et al. |
| 7,753,904 | B2 | 7/2010 | Shelton, IV et al. |
| 7,766,210 | B2 | 8/2010 | Shelton, IV et al. |
| 7,770,775 | B2 | 8/2010 | Shelton, IV et al. |
| 7,819,297 | B2 | 10/2010 | Doll et al. |
| 7,824,401 | B2 | 11/2010 | Manzo et al. |
| 7,845,537 | B2 | 12/2010 | Shelton, IV et al. |
| 7,918,377 | B2 | 4/2011 | Measamer et al. |
| 7,922,061 | B2 | 4/2011 | Shelton, IV et al. |
| 7,954,682 | B2 | 6/2011 | Giordano et al. |
| 7,959,050 | B2 | 6/2011 | Smith et al. |
| 8,028,885 | B2 | 10/2011 | Smith et al. |
| 8,157,145 | B2 | 4/2012 | Shelton, IV et al. |
| 8,161,977 | B2 | 4/2012 | Shelton, IV et al. |
| 8,167,185 | B2 | 5/2012 | Shelton, IV et al. |
| 8,186,555 | B2 | 5/2012 | Shelton, IV et al. |
| 8,194,122 | B2 | 6/2012 | Amling et al. |
| 8,210,411 | B2 | 7/2012 | Yates et al. |
| 8,292,888 | B2 | 10/2012 | Whitman |
| 8,357,144 | B2 | 1/2013 | Whitman et al. |
| 8,397,971 | B2 | 3/2013 | Yates et al. |
| 8,444,036 | B2 | 5/2013 | Shelton, IV |
| 8,453,907 | B2 | 6/2013 | Laurent et al. |
| 8,459,520 | B2 | 6/2013 | Giordano et al. |
| 8,498,691 | B2 | 7/2013 | Moll et al. |
| 8,608,044 | B2 | 12/2013 | Hueil et al. |
| 8,632,535 | B2 | 1/2014 | Shelton, IV et al. |
| 8,652,120 | B2 | 2/2014 | Giordano et al. |
| 8,708,213 | B2 | 4/2014 | Shelton, IV et al. |
| 8,752,747 | B2 | 6/2014 | Shelton, IV et al. |
| 8,822,934 | B2 | 9/2014 | Sayeh et al. |
| 8,876,857 | B2 | 11/2014 | Burbank |
| 8,905,977 | B2 | 12/2014 | Shelton et al. |
| 9,351,727 | B2 | 5/2016 | Leimbach et al. |
| 9,517,068 | B2 | 12/2016 | Shelton, IV et al. |
| 9,554,803 | B2 | 1/2017 | Smith et al. |
| 9,629,626 | B2 | 4/2017 | Soltz et al. |

(56) References Cited

U.S. PATENT DOCUMENTS

| | | | |
|---|---|---|---|
| 9,861,359 B2 | 1/2018 | Shelton, IV et al. | |
| 10,010,322 B2 | 7/2018 | Shelton, IV et al. | |
| 10,238,391 B2 | 3/2019 | Leimbach et al. | |
| 10,426,463 B2 | 10/2019 | Shelton, IV et al. | |
| 10,517,590 B2 | 12/2019 | Giordano et al. | |
| 10,675,028 B2 | 6/2020 | Shelton, IV et al. | |
| 10,736,628 B2 | 8/2020 | Yates et al. | |
| 10,905,415 B2 | 2/2021 | DiNardo et al. | |
| 10,952,728 B2 | 3/2021 | Shelton, IV et al. | |
| 11,051,813 B2 | 7/2021 | Shelton, IV et al. | |
| 11,612,393 B2 | 3/2023 | Morgan et al. | |
| 11,793,518 B2 | 10/2023 | Shelton, IV et al. | |
| 12,004,741 B2 | 6/2024 | Shelton, IV et al. | |
| 12,161,329 B2 * | 12/2024 | Shelton, IV | A61B 34/76 |
| 2002/0091374 A1 | 7/2002 | Cooper | |
| 2003/0093103 A1 | 5/2003 | Malackowski et al. | |
| 2004/0122419 A1 | 6/2004 | Neuberger | |
| 2004/0232197 A1 | 11/2004 | Shelton, IV et al. | |
| 2005/0080342 A1 | 4/2005 | Gilreath et al. | |
| 2005/0131390 A1 | 6/2005 | Heinrich et al. | |
| 2007/0078484 A1 | 4/2007 | Talarico et al. | |
| 2007/0175950 A1 | 8/2007 | Shelton et al. | |
| 2007/0175951 A1 | 8/2007 | Shelton et al. | |
| 2007/0175955 A1 | 8/2007 | Shelton et al. | |
| 2007/0175956 A1 | 8/2007 | Swayze et al. | |
| 2008/0196253 A1 | 8/2008 | Ezra et al. | |
| 2009/0090763 A1 | 4/2009 | Zemlok et al. | |
| 2009/0099876 A1 | 4/2009 | Whitman | |
| 2010/0069942 A1 * | 3/2010 | Shelton, IV | A61B 17/07207 227/175.1 |
| 2011/0006101 A1 | 1/2011 | Hall et al. | |
| 2011/0024477 A1 | 2/2011 | Hall | |
| 2011/0290856 A1 | 12/2011 | Shelton, IV et al. | |
| 2011/0295295 A1 | 12/2011 | Shelton, IV et al. | |
| 2012/0292367 A1 | 11/2012 | Morgan et al. | |
| 2013/0020376 A1 | 1/2013 | Shelton, IV et al. | |
| 2013/0026208 A1 | 1/2013 | Shelton, IV et al. | |
| 2014/0284371 A1 | 9/2014 | Morgan et al. | |
| 2014/0367445 A1 | 12/2014 | Ingmanson et al. | |

FOREIGN PATENT DOCUMENTS

| | | | |
|---|---|---|---|
| CN | 2868212 Y | 2/2007 | |
| CN | 101401736 A | 4/2009 | |
| JP | 2005135344 A | 5/2005 | |
| RU | 2008830 C1 | 3/1994 | |
| SU | 1009439 A | 4/1983 | |
| SU | 1042742 A1 | 9/1983 | |
| WO | WO-9308754 A1 | 5/1993 | |
| WO | WO-2007137304 A2 | 11/2007 | |

OTHER PUBLICATIONS

IPR2018-00938_Petitioners_Request_for_Refund_of_Post-Institution_Fees_06_12_2019.

IPR2018-00938_DECISION_ON_REQUEST_FOR_REHEARING_Denying_Petitioners_Request for_Rehearing_37_CFR_sec_4271(d)_06_11_2019.

IPR2018-00938_Petitioners_Request_for_Rehearing_12_20_2018.

IPR2018-00938_Trial_Instituted_Document_12_04_2018.

IPR2018-00938 Statutory_Disclaimer_under_37_CFR_1321(a),_filed_on_September_5_2018 for_US_Patent_No_9113874_09-06-2018.

IPR2018-00938 Excerpts_from_Technology_Tutorial_filed_in_Ethicon_LLC_et_al_v_Intuitive Surgical_Inc_et_al_CA_No_17-871_(LPS)(CJB)_(District of Delaware).

IPR2018-00938_Patent_Owners_Preliminary_Response_09-06-2018.

IPR2018-00938_Patent_Owners_Updated_Mandatory_Notices_Pursuant_to_37_CFR_428_07-03-2018.

IPR2018-00938_Notice_of_Accord_Filing_Date_06_07_2018.

IPR2018-00938_Patent_Owners_Mandatory_Notices_Pursuant_to_37_CFR_428_06_06_2018.

IPR2018-00938_Patent_Owners_Power_of_Attorney_06_06_2018.

IPR2018-00938 Excerpts_from_the_Prosecution_History_of_the_874_Patent_Part_1_of_2 05-16-2018 Part_1_of_4.

IPR2018-00938_Excerpts_from_the_Prosecution_History_of_the_874_Patent_Part_1_of_2 05-16-2018_Part_2_of_4.

IPR2018-00938_Excerpts_from_the_Prosecution_History_of_the_874_Patent_Part_1_of_2 05-16-2018_Part_3_of_4.

IPR2018-00938_Excerpts_from_the_Prosecution_History_of_the_874_Patent_Part_1_of_2 05-16-2018_Part_4_of_4.

IPR2018-00938_US_Patent_No_9113874_to_Shelton_IV_et_al_05-16-2018_Part_1_of_3.

IPR2018-00938_US_Patent_No_9113874_to_Shelton_IV_et_al_05-16-2018_Part_2_of_3.

IPR2018-00938_US_Patent_No_9113874_to_Shelton_IV_et_al_05-16-2018_Part_3_of_3.

IPR2018-00938_US_Pat_App_Pub_No_20020165541_to_Whitman_05_16_2018.

IPR2018-00938_Excerpts_from_the_Prosecution_Histoy_of_the_537_patent_Part_2_of_2 05-16-2018_Part_1_of_2.

IPR2018-00938_Excerpts_from_the_Prosecution_Histoy_of_the_537_patent_Part_2_of_2 05-16-2018_Part_2_of_2.

IPR2018-00938_US_Patent_No_5662667_to_Knodel_et_al_05-16-2018.

IPR2018-00938_8161977_to_Shelton_IV_05-16-2018_Part_1_of_3.

IPR2018-00938_8161977_to_Shelton_IV_05-16-2018_Part_2_of_3.

IPR2018-00938_8161977_to_Shelton_IV_05-16-2018_Part_3_of_3.

IPR2018-00938_Excerpts_from_the Prosecution_History_of_the_977_Patent_05-16-2018_Part_1_of_14.

IPR2018-00938_Excerpts_from_the Prosecution_History_of_the_977_Patent_05-16-2018_Part_2_of_14.

IPR2018-00938_Excerpts_from_the Prosecution_History_of_the_977_Patent_05-16-2018_Part_3_of_14.

IPR2018-00938_Excerpts_from_the Prosecution_History_of_the_977_Patent_05-16-2018_Part_4_of_14.

IPR2018-00938_Excerpts_from_the Prosecution_History_of_the_977_Patent_05-16-2018_Part_5_of_14.

IPR2018-00938_Excerpts_from_the Prosecution_History_of_the_977_Patent_05-16-2018_Part_6_of_14.

IPR2018-00938_Excerpts_from_the Prosecution_History_of_the_977_Patent_05-16-2018_Part_7_of_14.

IPR2018-00938_Excerpts_from_the Prosecution_History_of_the_977_Patent_05-16-2018_Part_8_of_14.

IPR2018-00938_Excerpts_from_the Prosecution_History_of_the_977_Patent_05-16-2018_Part_9_of_14.

IPR2018-00938_Excerpts_from_the Prosecution_History_of_the_977_Patent_05-16-2018_Part_10_of_14.

IPR2018-00938_Excerpts_from_the Prosecution_History_of_the_977_Patent_05-16- 2018_Part_11_of_14.

IPR2018-00938_Excerpts_from_the Prosecution_History_of_the_977_Patent_05-16- 2018_Part_12_of_14.

IPR2018-00938_Excerpts_from_the Prosecution_History_of_the_977_Patent_05-16- 2018_Part_13_of_14.

IPR2018-00938_Excerpts_from_the Prosecution_History_of_the_977_Patent_05-16- 2018_Part_14_of_14.

IPR2018-00938_Excerpts_from_the_Prosecution_Histoy_of_the_537_patent_Part_1_of_2_05-16-2018 Part_1_of_3.

IPR2018-00938_Excerpts_from_the_Prosecution_Histoy_of_the_537_patent_Part_1_of_2_05-16-2018_Part_2_of_3.

IPR2018-00938_Excerpts_from_the_Prosecution_Histoy_of_the_537_patent_Part_1_of_2_05-16-2018_Part_3_of_3.

IPR2018-00938_Petitioners_Power_of_Attorney_05-16-2018.

IPR2018- 00938_Excerpts_from_the_Prosecution_History_of_the_603_Patent_05_16_2018_Part_1_of_20.

IPR2018-00938_Excerpts_from_the_Prosecution_History_of_the_603_Patent May 16, 2018 Part_2_of_20.

IPR2018-00938_Excerpts_from_the_Prosecution_History_of_the_603_Patent May 16, 2018 Part_3_of_20.

IPR2018-00938_Excerpts_from_the_Prosecution_History_of_the_603_Patent May 16, 2018 Part_4_of_20.

(56) References Cited

OTHER PUBLICATIONS

IPR2018-00938_Excerpts_from_the_Prosecution_History_of_the_ 603_Patent May 16, 2018 Part_5_of_20.
IPR2018-0938_Excerpts_from_the_Prosecution_History_of_the_ 603_Patent May 16, 2018 Part_6_of_20.
IPR2018-00938_Excerpts_from_the_Prosecution_History_of_the_ 603_Patent May 16, 2018 Part_7_of_20.
IPR2018-00938_Excerpts_from_the_Prosecution_History_of_the_ 603_Patent May 16, 2018 Part_8_of_20.
IPR2018-00938_Excerpts_from_the_Prosecution_History_of_the_ 603_Patent May 16, 2018 Part_9_of_20.
IPR2018-00938_Excerpts_from_the_Prosecution_History_of_the_ 603_Patent May 16, 2018 Part_10_of_20.
IPR2018-00938_Excerpts_from_the_Prosecution_History_of_the_ 603_Patent May 16, 2018 Part_11_of_20.
IPR2018-00938_Excerpts_from_the_Prosecution_History_of_the_ 603_Patent May 16, 2018 Part_12_of_20.
IPR2018-00938_Excerpts_from_the_Prosecution_History_of_the_ 603_Patent May 16, 2018 Part_13_of_20.
IPR2018-00938_Excerpts_from_the_Prosecution_History_of_the_ 603_Patent May 16, 2018 Part_14_of_20.
IPR2018-00938_Excerpts_from_the_Prosecution_History_of_the_ 603_Patent May 16, 2018 Part_15_of_20.
IPR2018-00938_Excerpts_from_the_Prosecution_History_of_the_ 603_Patent May 16, 2018 Part_16_of_20.
IPR2018-00938_Excerpts_from_the_Prosecution_History_of_the_ 603_Patent May 16, 2018 Part_17_of_20.
IPR2018-00938_Excerpts_from_the_Prosecution_History_of_the_ 603_Patent May 16, 2018 Part_18_of_20.
IPR2018-00938_Excerpts_from_the_Prosecution_History_of_the_ 603_Patent May 16, 2018 Part_19_of_20.
IPR2018-00938_Excerpts_from_the_Prosecution_History_of_the_ 603_Patent 05-16-2018-Part_20_of_20.
IPR2018-00938_Excerpts_from_the_Prosecution_History_of_the_ 874_Patent_Part_2_of_2_05-16-2018_Part_1_of_3.
IPR2018-00938_Excerpts_from_the_Prosecution_History_of_the_ 874_Patent_Part_2_of_2_05-16-2018_Part_2_of_3.
IPR2018-00938_Excerpts_from_the_Prosecution_History_of_the_ 874_Patent_Part_2_of_2_05-16-2018_Part_3_of_3.
IPR2018-00938_Petition_for_Inter_Partes_Review_05-16-2018.
IPR2018-00938_US_Patent_No_7845537_to_Shelton_IV_05-16-2018_Part_1_of_3.
IPR2018-00938_US_Patent_No_7845537_to_Shelton_IV_05-16-2018_Part_2_of_3.
IPR2018-00938_US_Patent_No_7845537_to_Shelton_IV_05-16-2018_Part_3_of_3.
IPR2018-00938_US_Patent_No_5383880_to_Hooven_05-16-2018.
IPR2018-00938_US_Patent_No_8820603_to_Shelton_IV_05-16-2018_Part_1_of_3.
IPR2018-00938_US_Patent_No_8820603_to_Shelton_IV_05-16-2018_Part_2_of_3.
IPR2018-00938_US_Patent_No_8820603_to_Shelton_IV_05-16-2018_Part_3_of_3.
IPR2018-00938_US_Patent_No_5796188_to_Bays_05-16-2018.
IPR2018-00938 US_Patent_No_5702408_to_Wales_et_al_05-16-2018.
IPR2018-00938_Declaration_of_Dr_Bryan_Knodel_05-16-2018.
ITC Investigation No. 337-TA-1167 Commission Opinion (public version), dated Dec. 20, 2021.
United States International Trade Commission, Initial Determination On Violation Of Section 337 And Recommended Determination On Remedy And Bond, Investigation No. 337-TA-1167, Public Version, dated Jun. 8, 2021.
United States International Trade Commission, Notice Of A Final Determination Finding A Violation Of Section 337 And Issuance Of Remedial Orders; Suspension Of Enforcement Of The Remedial Orders Pending Final Resolution Of A Final Written Decision By The Patent Trial And Appeal Board; And Termination Of The Investigation, Investigation No. 337-TA-1167, issued Oct. 14, 2021.

* cited by examiner

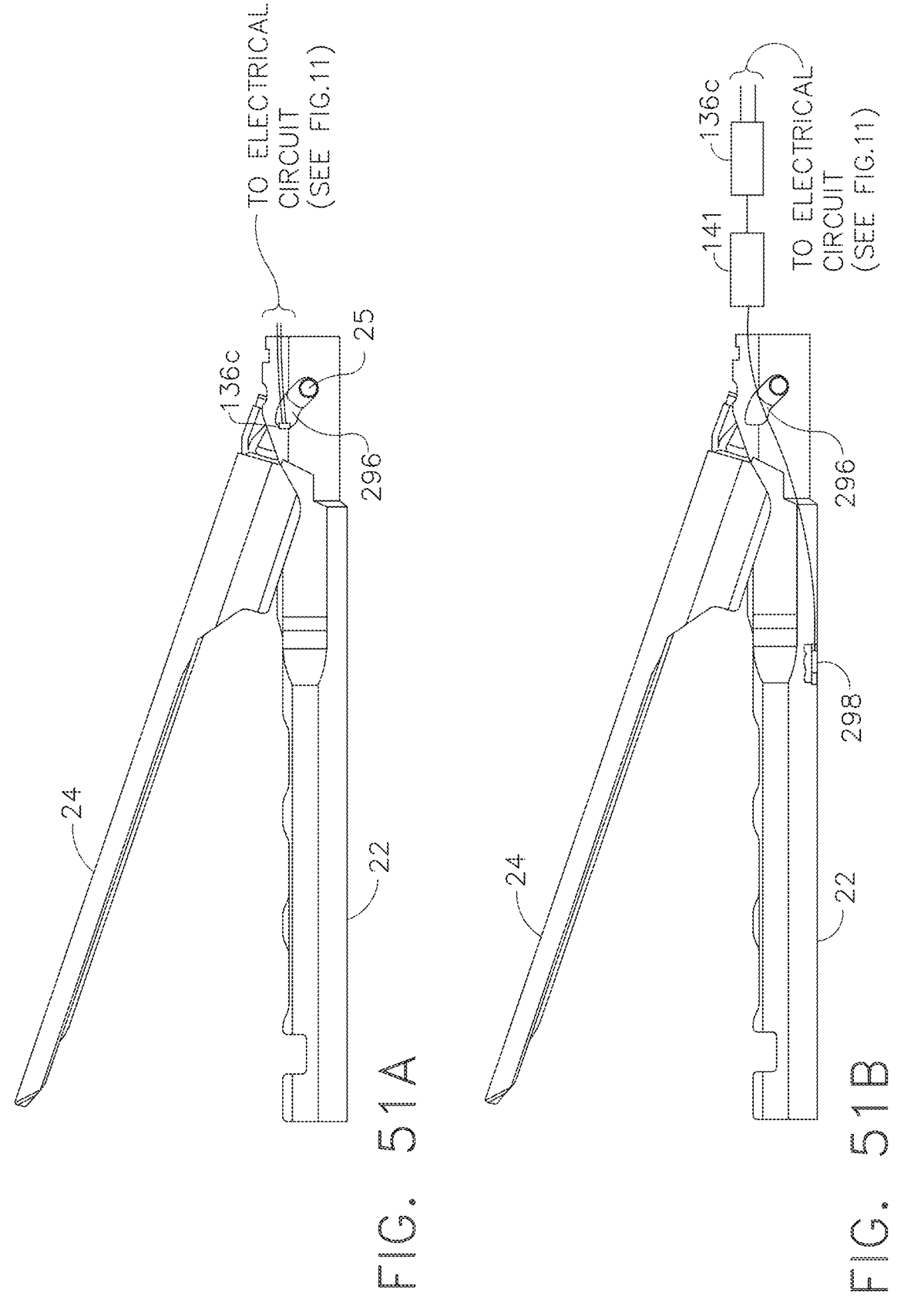
F I G. 5 1 A
F I G. 5 1 B

| EVENT # | CLOSURE LOAD | FIRING STROKE | FIRING LOAD (MAX) | KNIFE POSITION % | ANVIL CLOSED/OPEN | SLED PRESENT YES/NO | CARTRIDGE PRESENT YES/NO |
|---|---|---|---|---|---|---|---|
| 1 | 10 | | | | 0 | 1 | 1 |
| 2 | 12 | | | | 0 | 1 | 1 |
| 3 | 15 | | | | 0 | 1 | 1 |
| 4 | 50 | | | | 1 | 1 | 1 |
| 25 | 25 | 1 | 250 | .33 | 1 | 0 | 1 |
| 26 | 100 | 2 | 400 | .66 | 1 | 0 | 1 |
| 27 | 120 | 3 | 200 | .75 | 1 | 0 | 1 |
| 55 | 50 | | | | 1 | 0 | 1 |
| 56 | 50 | | | | 1 | 0 | 1 |

2300

2302 2304 2306 2308 2310 2312 2314 2316

MEMORY EVENT RECORD

LOCKOUTS LOCKOUT MEMORY IS — (YES – NO – ) — (ON –1 OFF–0)

EXAMPLE: 3 STEP FIRING

SURGICAL STAPLING SYSTEMS INCLUDING A TIMER FOR THE FIRING MOTION

CROSS-REFERENCE TO RELATED APPLICATIONS

This application is a continuation application claiming priority under 35 U.S.C. § 120 to U.S. patent application Ser. No. 18/368,236, entitled POWERED SURGICAL INSTRUMENTS WITH FIRING SYSTEM LOCKOUT ARRANGEMENTS, filed Sep. 14, 2023, which issued on Dec. 10, 2024 as U.S. Pat. No. 12,161,329, which is a continuation application claiming priority under 35 U.S.C. § 120 to U.S. patent application Ser. No. 17/208,296, entitled POWERED SURGICAL INSTRUMENTS WITH FIRING SYSTEM LOCKOUT ARRANGEMENTS, filed Mar. 22, 2021, which issued on Oct. 24, 2023 as U.S. Pat. No. 11,793,518, which is a continuation application claiming priority under 35 U.S.C. § 120 to U.S. patent application Ser. No. 16/906,397, entitled POWERED SURGICAL INSTRU- MENTS WITH FIRING SYSTEM LOCKOUT ARRANGEMENTS, filed Jun. 19, 2020, which issued on Mar. 23, 2021 as U.S. Pat. No. 10,952,728, which is a continuation application claiming priority under 35 U.S.C. § 120 to U.S. patent application Ser. No. 16/420,870, entitled POWERED SURGICAL INSTRUMENTS WITH FIRING SYSTEM LOCKOUT ARRANGEMENTS, filed May 23, 2019, which issued on Jul. 6, 2021 as U.S. Pat. No. 11,051, 813, which is a continuation application claiming priority under 35 U.S.C. § 120 to U.S. patent application Ser. No. 15/864,922, entitled POWERED SURGICAL INSTRU- MENTS WITH FIRING SYSTEM LOCKOUT ARRANGEMENTS, filed Jan. 8, 2018, which issued on Jun. 9, 2020 as U.S. Pat. No. 10,675,028, which is a continuation application claiming priority under 35 U.S.C. § 120 to U.S. patent application Ser. No. 13/796,996, entitled POWERED SURGICAL INSTRUMENTS WITH FIRING SYSTEM LOCKOUT ARRANGEMENTS, filed Mar. 12, 2013, which issued on Jan. 9, 2018 as U.S. Pat. No. 9,861,359, the entire disclosures of each are hereby incor- porated by reference herein. The entire disclosures of U.S. patent application Ser. No. 13/424,648, entitled SURGICAL INSTRUMENT HAVING RECORDING CAPABILITIES, filed Mar. 20, 2012, which issued on Jun. 17, 2014 as U.S. Pat. No. 8,752,747; U.S. patent application Ser. No. 12/949, 099, entitled SURGICAL INSTRUMENT HAVING RECORDING CAPABILITIES, filed Nov. 18, 2010, which issued on May 1, 2012 as U.S. Pat. No. 8,167,185; U.S. patent application Ser. No. 11/343,803, entitled SURGICAL INSTRUMENT HAVING RECORDING CAPABILITIES, filed Jan. 31, 2006, which issued on Dec. 7, 2010 as U.S. Pat. No. 7,845,537; U.S. patent application Ser. No. 12/846,228, entitled MOTOR DRIVEN SURGICAL FASTENER DEVICE WITH CUTTING MEMBER LOCKOUT ARRANGEMENTS, filed Jul. 29, 2010, now U.S. Patent Application Publication No. 2011/0006101; U.S. patent application Ser. No. 12/693,460, entitled DRIVEN SURGI- CAL STAPLER IMPROVEMENTS, filed Jan. 26, 2010, now U.S. Patent Application Publication No. 2011/0024477; U.S. Provisional Patent Application Ser. No. 61/150,382, entitled MOTOR-DRIVEN SURGICAL STAPLER IMPROVEMENTS, filed on Feb. 6, 2009; U.S. patent application Ser. No. 16/420,879, entitled ROBOTICALLY- CONTROLLED END EFFECTOR, filed May 23, 2019, which issued on Mar. 28, 2023 as U.S. Pat. No. 11,612,393; U.S. patent application Ser. No. 14/298,252, entitled SUR- GICAL STAPLING SYSTEM COMPRISING AN ANVIL SENSOR, filed Jun. 6, 2014, now U.S. Patent Application Publication No. 2014/0284371; U.S. patent application Ser. No. 13/372,195, entitled ROBOTICALLY-CONTROLLED END EFFECTOR, filed Feb. 13, 2012, now U.S. Patent Application Publication No. 2012/0292367; and U.S. patent application Ser. No. 13/118,272, entitled ROBOTICALLY- CONTROLLED SURGICAL INSTRUMENT WITH FORCE-FEEDBACK CAPABILITIES, filed May 27, 2011, now U.S. Patent Application Publication No. 2011/0290856, are hereby incorporated by reference herein.

The present application is related to the following U.S. patent applications, the entire disclosures of each are incor- porated herein by reference:

U.S. patent application Ser. No. 11/343,498, now U.S. Pat. No. 7,766,210, entitled MOTOR-DRIVEN SUR- GICAL CUTTING AND FASTENING INSTRU- MENT WITH USER FEEDBACK SYSTEM, Inven- tors: Frederick E. Shelton, IV, John Ouwerkerk and Jerome R. Morgan;

U.S. patent application Ser. No. 11/343,573, now U.S. Pat. No. 7,416,101, entitled MOTOR-DRIVEN SUR- GICAL CUTTING AND FASTENING INSTRU- MENT WITH LOADING FORCE FEEDBACK, Inventors: Frederick E. Shelton, IV, John N. Ouwerkerk, Jerome R. Morgan, and Jeffrey S. Swayze;

U.S. patent application Ser. No. 11/344,035, now U.S. Pat. No. 7,422,139, entitled MOTOR-DRIVEN SUR- GICAL CUTTING AND FASTENING INSTRU- MENT WITH TACTILE POSITION FEEDBACK, Inventors: Frederick E. Shelton, IV, John N. Ouwerkerk, Jerome R. Morgan, and Jeffrey S. Swayze;

U.S. patent application Ser. No. 11/343,447, now U.S. Pat. No. 7,770,775, entitled, MOTOR-DRIVEN SUR- GICAL CUTTING AND FASTENING INSTRU- MENT WITH ADAPTIVE USER FEEDBACK, Inventors: Frederick E. Shelton, IV, John N. Ouwerkerk, and Jerome R. Morgan;

U.S. patent application Ser. No. 11/343,562, now U.S. Pat. No. 7,568,603, entitled MOTOR-DRIVEN SUR- GICAL CUTTING AND FASTENING INSTRU- MENT WITH ARTICULATABLE END EFFECTOR, Inventors: Frederick E. Shelton, IV and Christoph L. Gillum;

U.S. patent application Ser. No. 11/344,024, now U.S. Pat. No. 8,186,555, entitled MOTOR-DRIVEN SUR- GICAL CUTTING AND FASTENING INSTRU- MENT WITH MECHANICAL CLOSURE SYSTEM, Inventors: Frederick E. Shelton, IV and Christoph L. Gillum;

U.S. patent application Ser. No. 11/343,321, now U.S. Patent Publication No. 2007/0175955, entitled SUR- GICAL CUTTING AND FASTENING INSTRU- MENT WITH CLOSURE TRIGGER LOCKING MECHANISM, Inventors: Frederick E. Shelton, IV and Kevin R. Doll;

U.S. patent application Ser. No. 11/343,563, now U.S. Patent Publication No. 2007/0175951, entitled GEAR- ING SELECTOR FOR A POWERED SURGICAL CUTTING AND FASTENING STAPLING INSTRU- MENT, Inventors: Frederick E. Shelton, IV, Jeffrey S. Swayze, Eugene L. Timperman;

U.S. patent application Ser. No. 11/344,020, now U.S. Pat. No. 7,464,846, entitled SURGICAL INSTRU- MENT HAVING A REMOVABLE BATTERY, Inven- tors: Frederick E. Shelton, IV, Kevin R. Doll, Jeffrey S. Swayze and Eugene Timperman;

U.S. patent application Ser. No. 11/343,439, now U.S. Pat. No. 7,644,848, entitled ELECTRONIC LOCK-OUTS AND SURGICAL INSTRUMENT INCLUD-ING SAME, Inventors: Jeffrey S. Swayze, Frederick E. Shelton, IV, Kevin R. Doll;

U.S. patent application Ser. No. 11/343,547, now U.S. Pat. No. 7,753,904, entitled ENDOSCOPIC SURGI-CAL INSTRUMENT WITH A HANDLE THAT CAN ARTICULATE WITH RESPECT TO THE SHAFT, Inventors: Frederick E. Shelton, IV, Jeffrey S. Swayze, Mark S. Ortiz, and Leslie M. Fugikawa;

U.S. patent application Ser. No. 11/344,021, now U.S. Pat. No. 7,464,849, entitled ELECTRO-MECHANI-CAL SURGICAL CUTTING AND FASTENING INSTRUMENT HAVING A ROTARY FIRING AND CLOSURE SYSTEM WITH PARALLEL CLOSURE AND ANVIL ALIGNMENT COMPONENTS, Inven-tors: Frederick E. Shelton, IV, Stephen J. Balek and Eugene L. Timperman;

U.S. patent application Ser. No. 11/343,546, now U.S. Patent Publication No. 2007/0175950, entitled DIS-POSABLE STAPLE CARTRIDGE HAVING AN ANVIL WITH TISSUE LOCATOR FOR USE WITH A SURGICAL CUTTING AND FASTENING INSTRUMENT AND MODULAR END EFFECTOR SYSTEM THEREFOR, Inventors: Frederick E. Shel-ton, IV, Michael S. Cropper, Joshua M. Broehl, Ryan S. Crisp, Jamison J. Float, Eugene L. Timperman; and U.S. patent application Ser. No. 11/343,545, now U.S. Pat. No. 8,708,213, entitled SURGICAL INSTRU-MENT HAVING A FEEDBACK SYSTEM, Inventors: Frederick E. Shelton, IV, Jerome R. Morgan, Kevin R. Doll, Jeffrey S. Swayze and Eugene Timperman.

BACKGROUND

The present invention relates in general to surgical instru-ments, and more particularly to minimally invasive surgical instruments capable of recording various conditions of the instrument.

The disclosed invention relates generally and in various embodiments to surgical stapling and cutting instruments structured and configured for applying lines of staples from a reusable staple cartridge into tissue while cutting the tissue between the applied staple lines. More particularly the disclosed invention relates to electronic interlocks for use in motorized surgical stapling and cutting instruments that prevent cutting of the tissue when the staple cartridge is not installed, is improperly installed, or is spent, or when the surgical stapling and cutting instrument is not otherwise in a condition to perform a stapling and cutting operation in a safe and/or optimal manner. The disclosed invention further relates to electronic interlocks for disabling use of certain instrument features while a stapling and cutting operation is in progress.

Endoscopic surgical instruments are often preferred over traditional open surgical devices because a smaller incision tends to reduce the post-operative recovery time and com-plications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparo-scopic applications, are capable of passing through a can-nula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocat-ing wedges which, when driven distally, pass through open-ings in the staple cartridge and engage drivers supporting the staples to effect the firing of the staples toward the anvil.

An example of a surgical stapler suitable for endoscopic applications is described in U.S. Pat. No. 5,465,895, entitled SURGICAL STAPLER INSTRUMENT to Knodel et al., which discloses an endocutter with distinct closing and firing actions. A clinician using this device is able to close the jaw members upon tissue to position the tissue prior to firing. Once the clinician has determined that the jaw mem-bers are properly gripping tissue, the clinician can then fire the surgical stapler with a single firing stroke, or multiple firing strokes, depending on the device. Firing the surgical stapler causes severing and stapling of the tissue. The simultaneous severing and stapling avoids complications that may arise when performing such actions sequentially with different surgical tools that respectively only sever and staple.

One specific advantage of being able to close upon tissue before firing is that the clinician is able to verify via an endoscope that the desired location for the cut has been achieved, including a sufficient amount of tissue has been captured between opposing jaws. Otherwise, opposing jaws may be drawn too close together, especially pinching at their distal ends, and thus not effectively forming closed staples in the severed tissue. At the other extreme, an excessive amount of clamped tissue may cause binding and an incom-plete firing.

When endoscopic surgical instruments fail, they are often returned to the manufacturer, or other entity, for analysis of the failure. If the failure resulted in a critical class of defect in the instrument, it is necessary for the manufacturer to determine the cause of the failure and determine whether a design change is required. In that case, the manufacturer may spend many hundreds of man-hours analyzing a failed instrument and attempting to reconstruct the conditions under which it failed based only on the damage to the instrument. It can be expensive and very challenging to analyze instrument failures in this way. Also, many of these analyses simply conclude that the failure was due to improper use of the instrument.

Because the actuating force (i.e., the "force-to-fire", or FTF) necessary to close the jaws and simultaneously per-form the cutting and stapling operation may be considerable, a manually-powered cutting and stapling instrument such as that described above may not be utilizable by otherwise qualified users who are unable to generate the required FTF. Accordingly, powered cutting and stapling instruments have been developed for decreasing the force-to-fire (FTF). Such instruments typically incorporate motors or other actuating mechanisms suitable for supplementing or replacing user-generated force for performing the cutting and stapling operation.

Although powered instruments provide numerous advan-tages, it is desirable to prevent inadvertent firing of the instrument under certain conditions. For example, firing the instrument without having a staple cartridge installed, or firing the instrument having an installed but spent staple cartridge, may result in cutting of tissue without simultaneous stapling to minimize bleeding. Additionally, firing of the instrument without proper closure of the jaw members may result in an unacceptable cutting and stapling operation and/or cause mechanical damage to the instrument. Similar consequences may result if the jaw members are inadvertently opened while a cutting and stapling operation is in progress. It is particularly desirable that interlock features for preventing such inadvertent firing and jaw manipulation be accomplished in a reliable way that is not subject to an intervening malfunction. Moreover, for ease of manufacturing and assembly, it is further desirable that the interlock features be accomplished with a minimum number of components.

Consequently, a significant need exists for electronic interlock features for use in powered cutting and stapling instruments that prevent inadvertent firing (i.e., cutting and stapling) and jaw manipulation during conditions such as those described above.

SUMMARY

In one general aspect, the present invention is directed to a surgical instrument. The surgical instrument has an end effector and a trigger in communication with the end effector. The surgical instrument also has a first sensor and an externally accessible memory device in communication with the first sensor. The first sensor has an output that represents a first condition of either the trigger or the end effector. The memory device is configured to record the output of the first sensor. In various embodiments, memory device may include an output port and/or a removable storage medium.

Also, in various embodiments, the output of the first sensor represents a condition of the end effector and the instrument further comprises a second sensor with an output representing a condition of the trigger. The memory device is configured to record the output of the first sensor and the second sensor.

In another general aspect, the present invention is directed to a method of recording the state of a surgical instrument. The method comprises the step of monitoring outputs of a plurality of sensors. The outputs represent conditions of the surgical instrument. The method also comprises the step of recording the outputs to a memory device when at least one of the conditions of the surgical instrument changes. In various embodiments, the method may also comprise the step of providing the recorded outputs of the plurality of sensors to an outside device.

DRAWINGS

Various embodiments of the present invention are described herein by way of example in conjunction with the following figures, wherein FIGS. 1 and 2 are perspective views of a surgical cutting and fastening instrument according to various embodiments of the present invention;

Figure 51C:
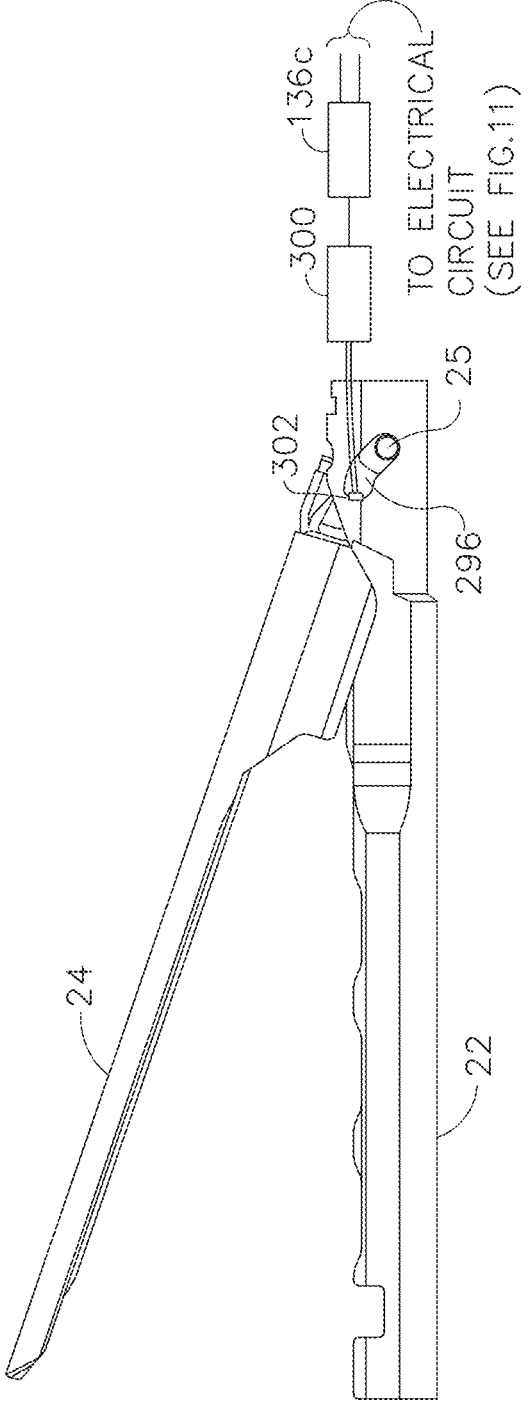
Figure 52A:
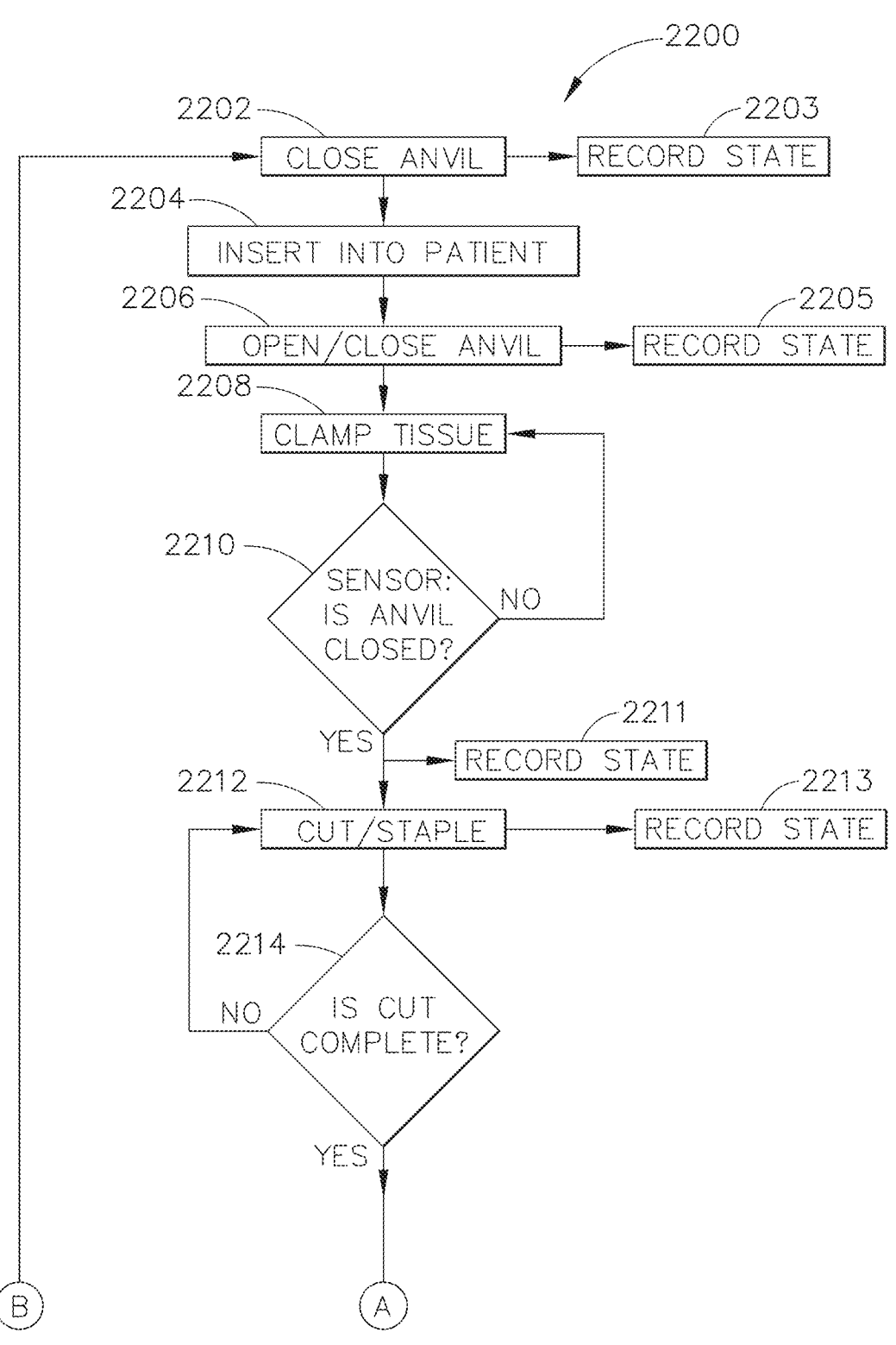
Figure 52B:
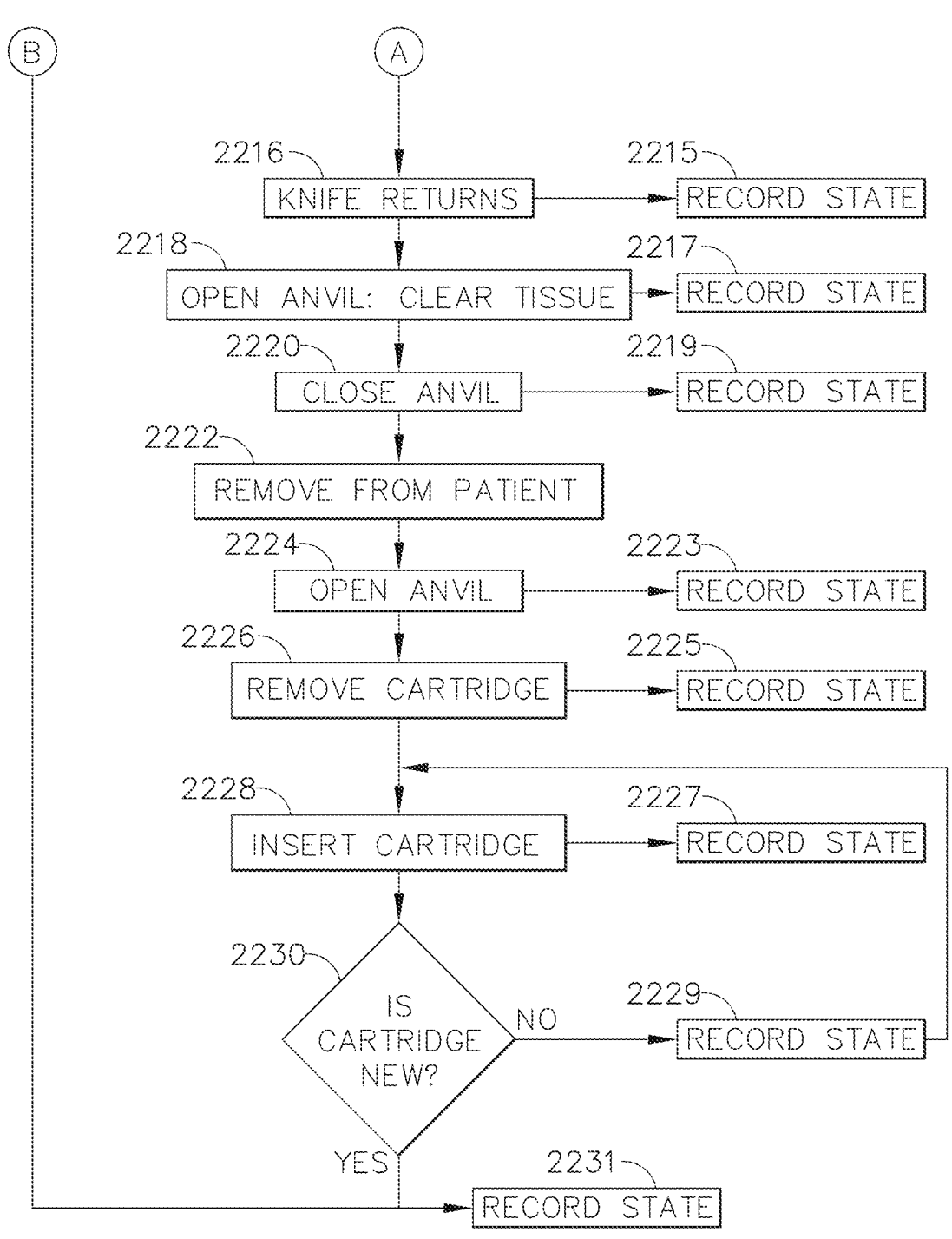
Figure 53:
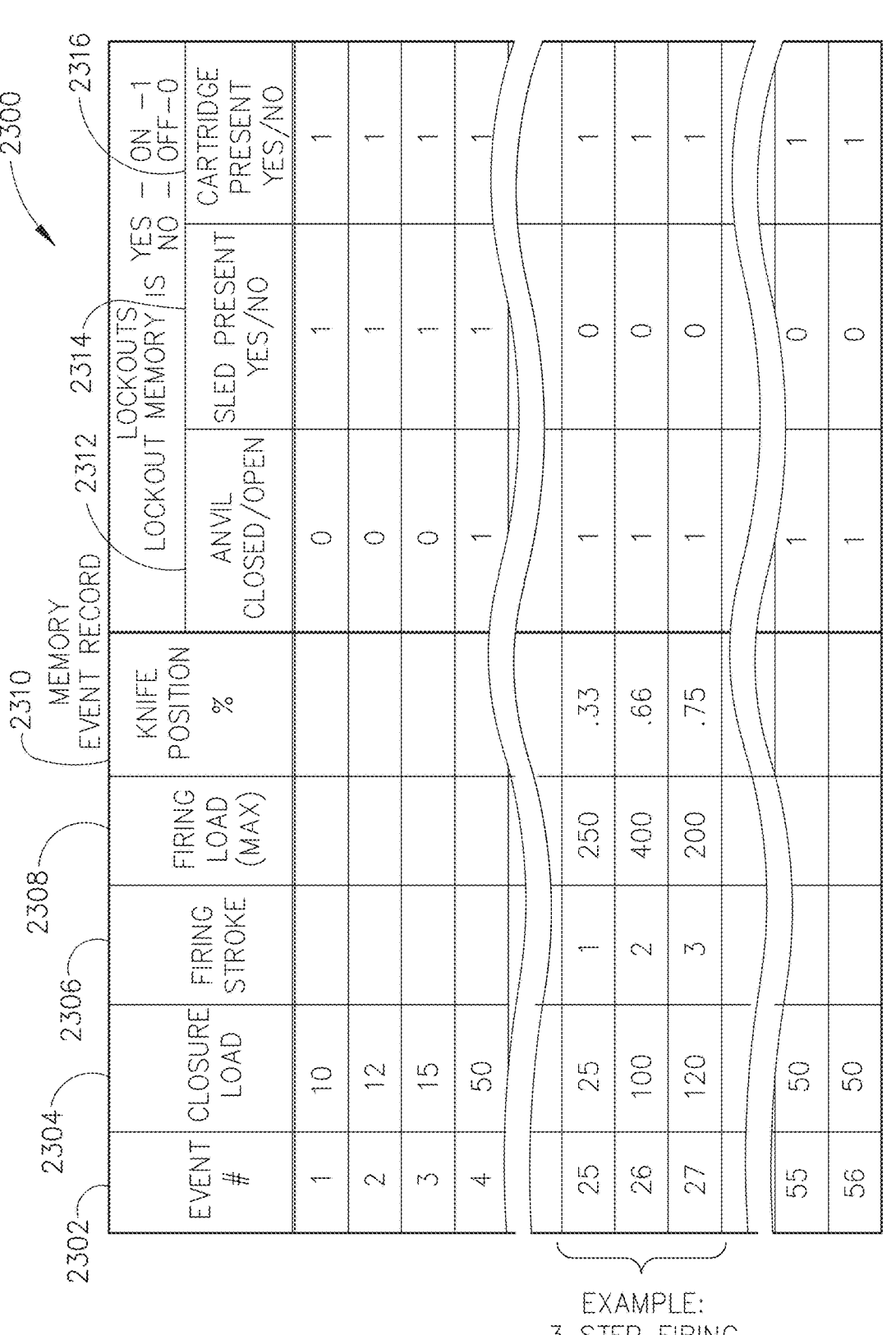

FIGS. 51A, 51B, and 51C illustrate mounting arrangements and configurations of the lockout sensor switches of an interlock circuit according to various embodiments of the present invention;

FIGS. 52A and 52B illustrate a flow chart showing a method for operating the instrument according to various embodiments; and FIG. 53 illustrates a memory chart showing exemplary recorded conditions of the instrument according to various embodiments of the present invention.

Figure 54:
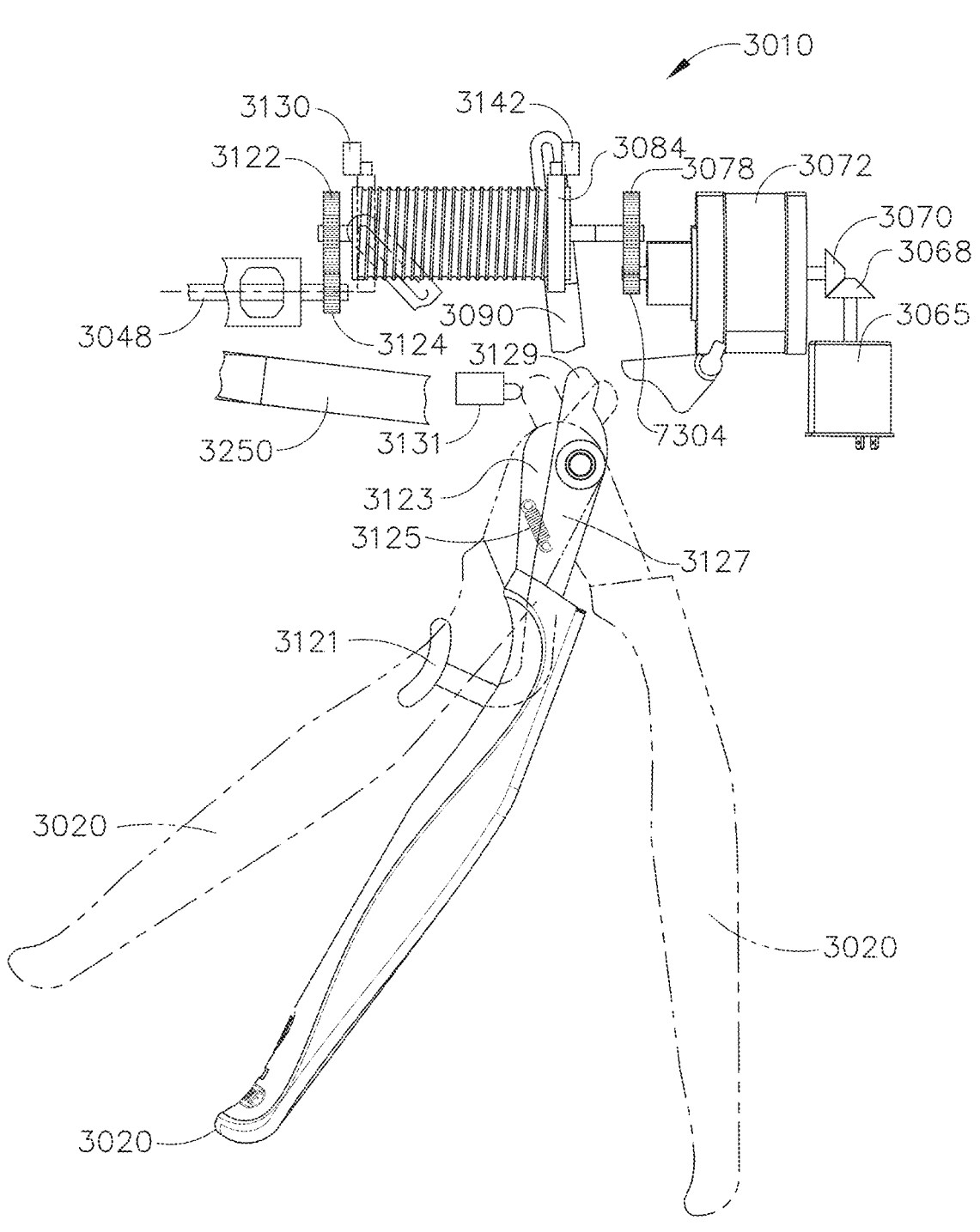
Figure 55:
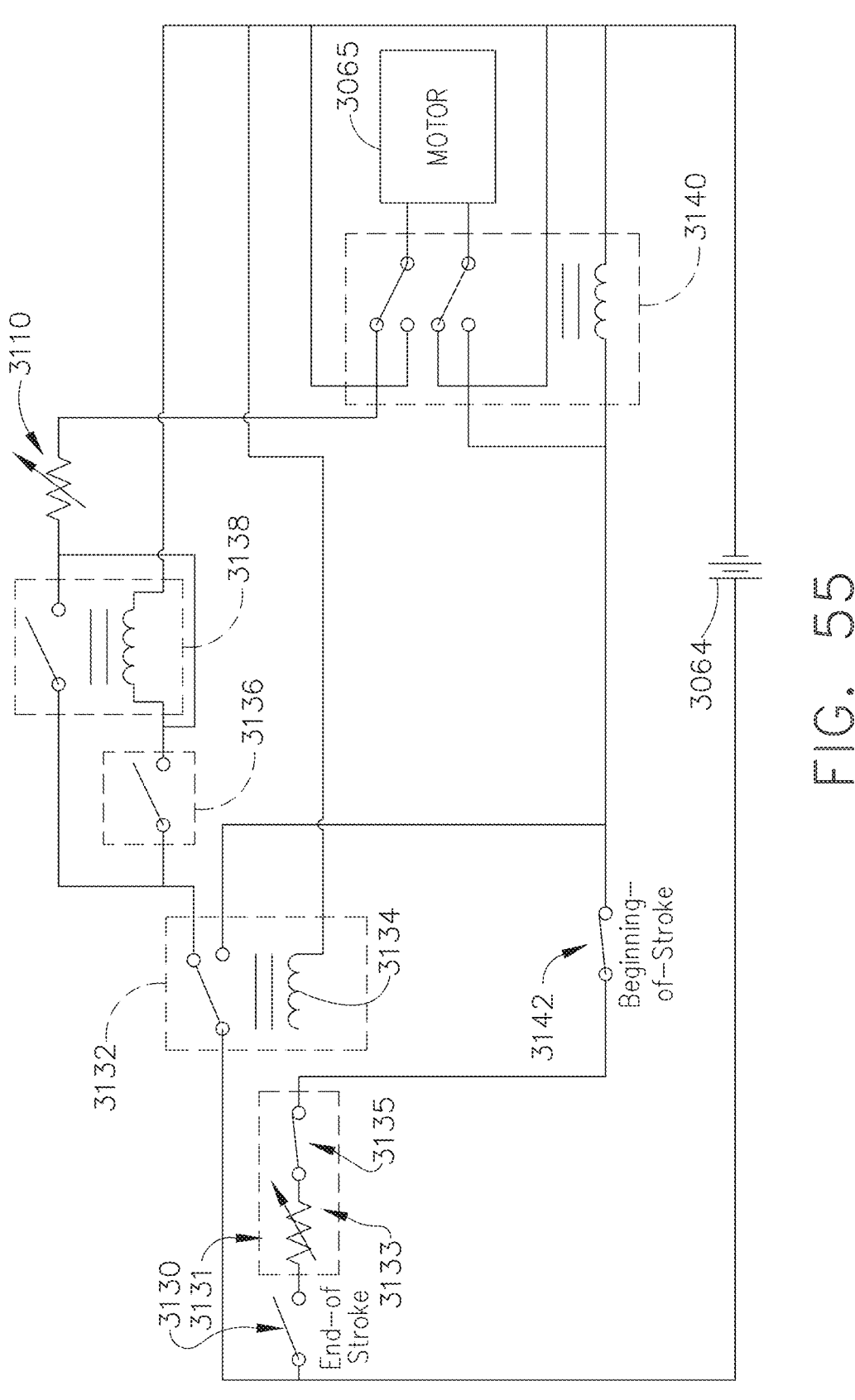

FIGS. 54 and 55 illustrate another embodiment of the present invention including an embodiment of an instrument wherein a retraction trigger is supported on the firing trigger for travel therewith.

Figure 56:
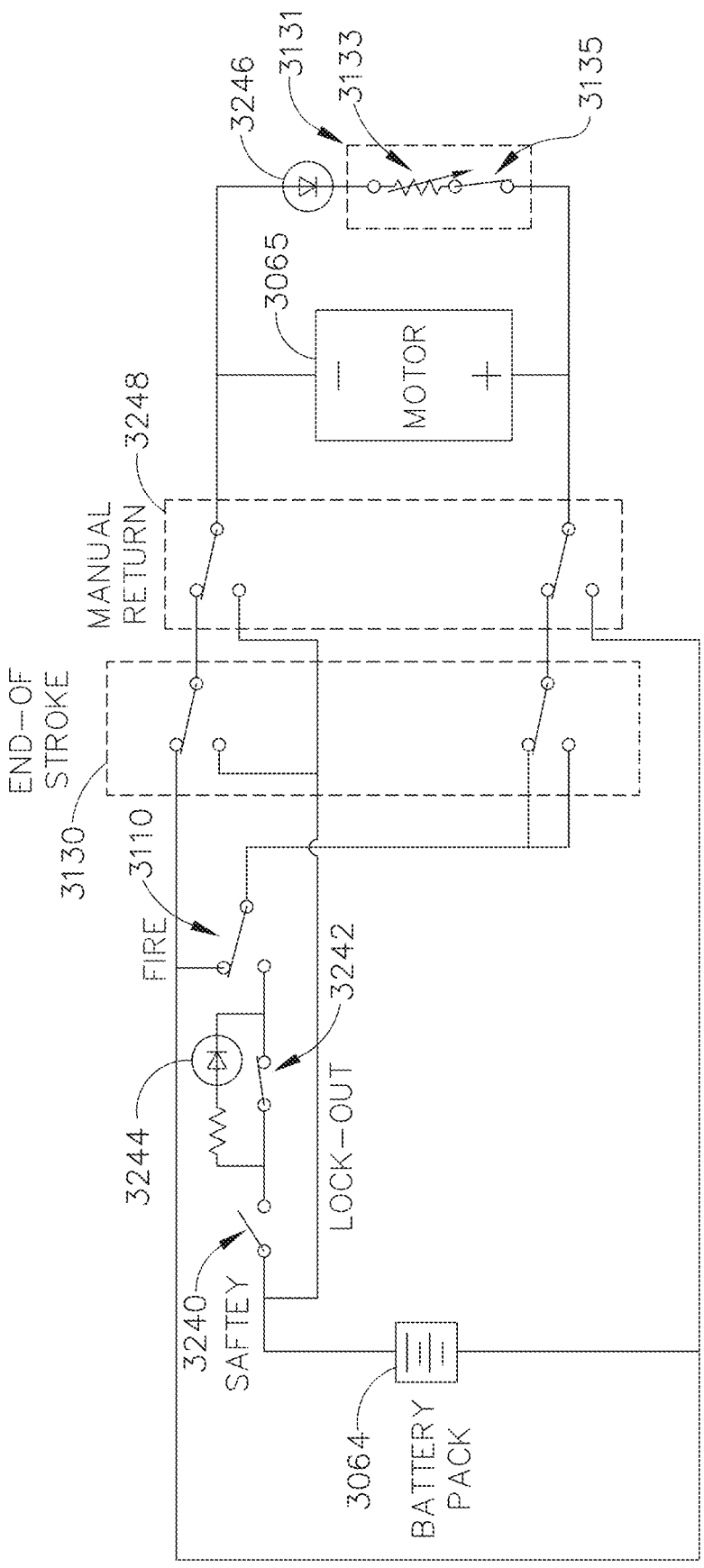

FIG. 56 shows another embodiment of a current control circuit according to various embodiments of the present invention.

FIGS. 57, 57A, 57B and 57C are schematic diagrams of other current control circuits according to various embodiments of the present invention.

Figure 58:
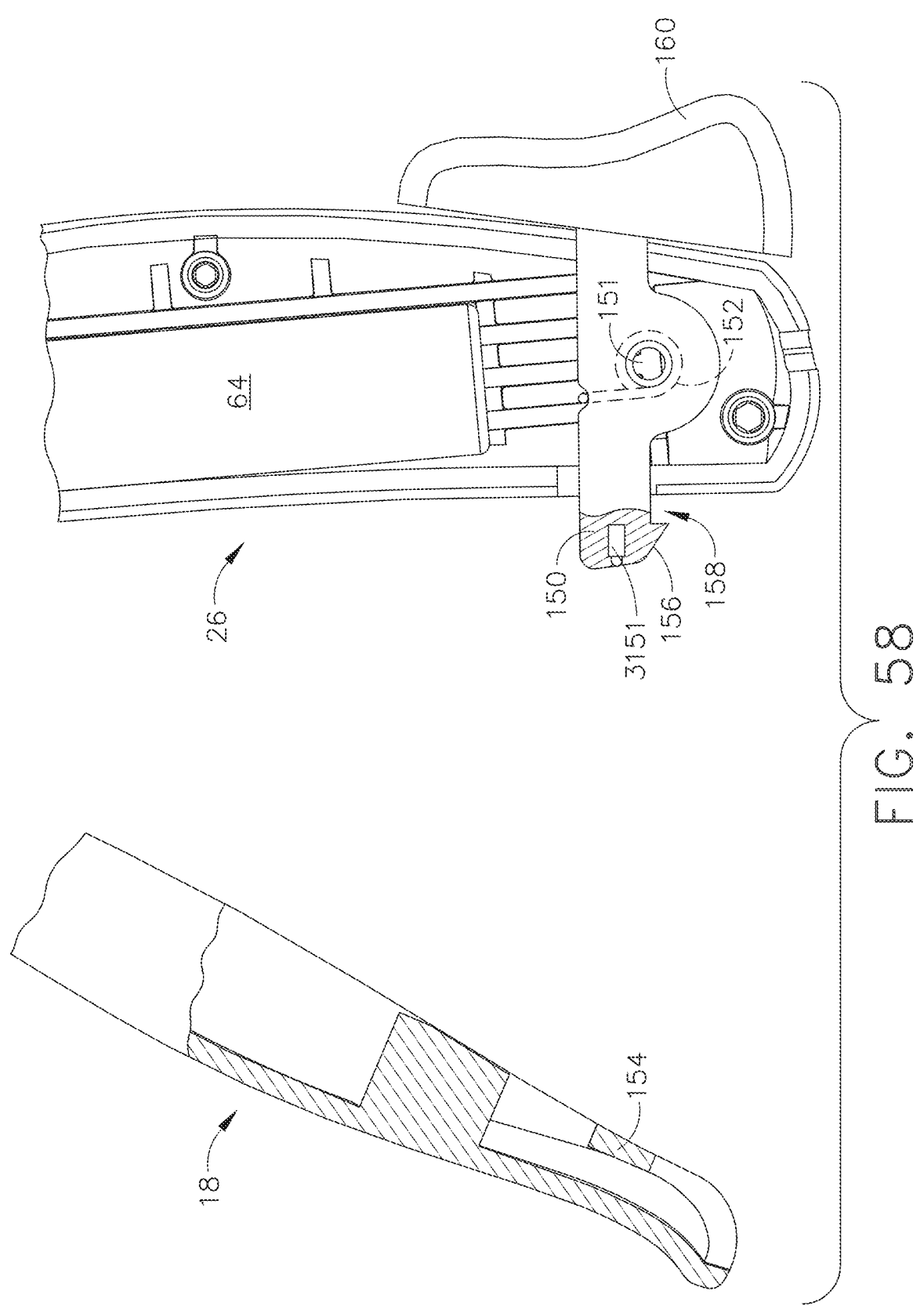
Figure 59:
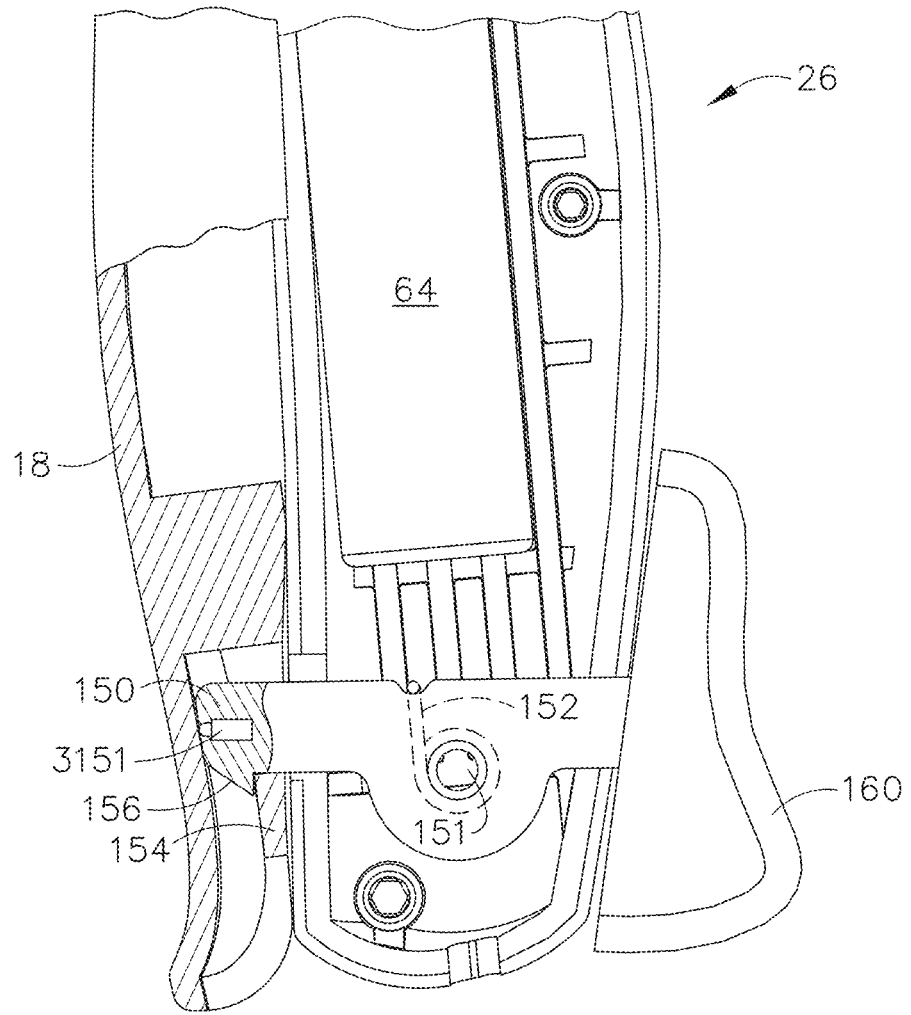

FIGS. 58 and 59 show one embodiment of a way to lock the closure trigger to the pistol grip portion of the handle.

Figure 60:
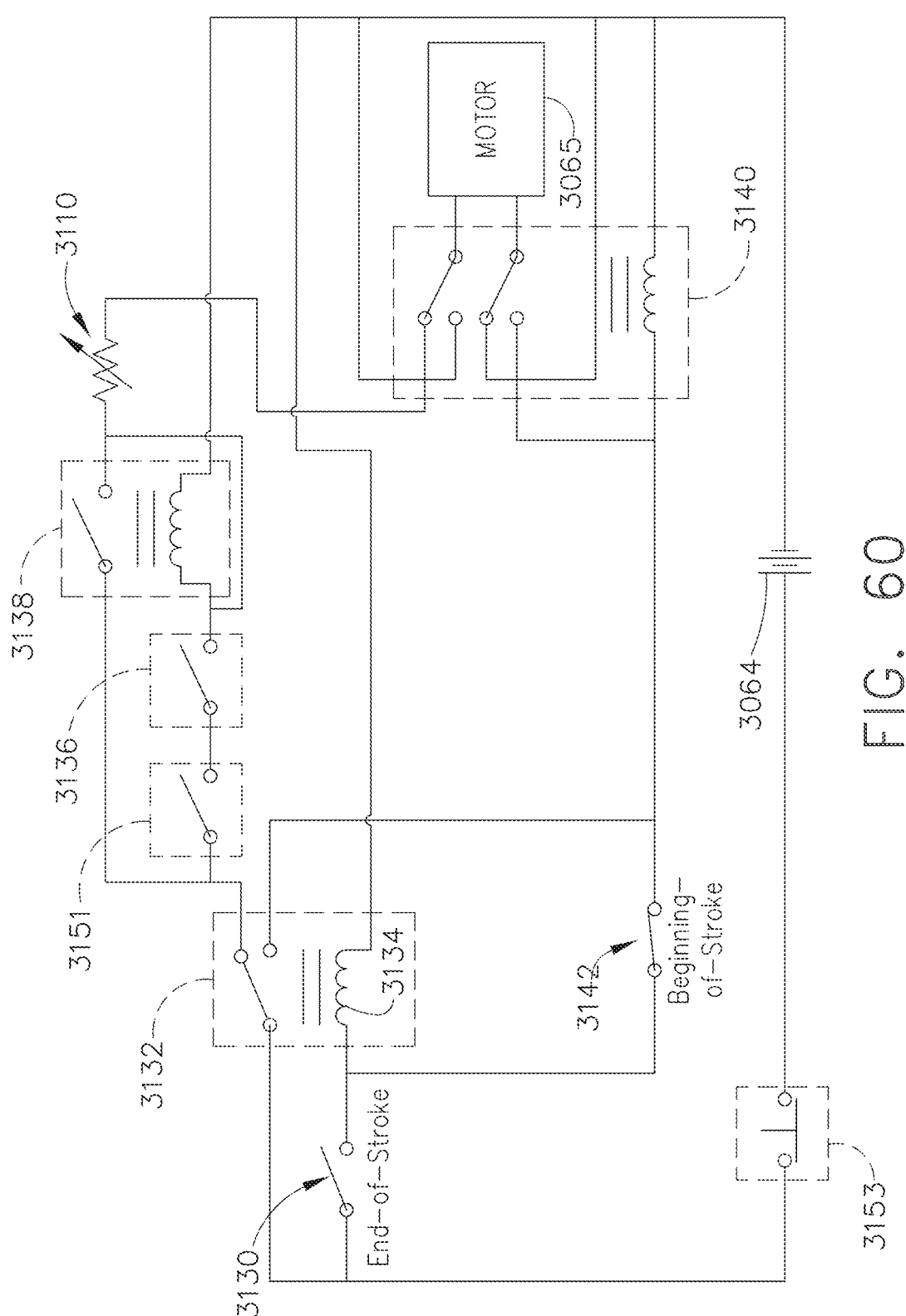

FIG. 60 is a schematic diagram of an electrical circuit of the instrument according to various embodiments of the present invention illustrating the use of the closure lock switch.

Figure 61:
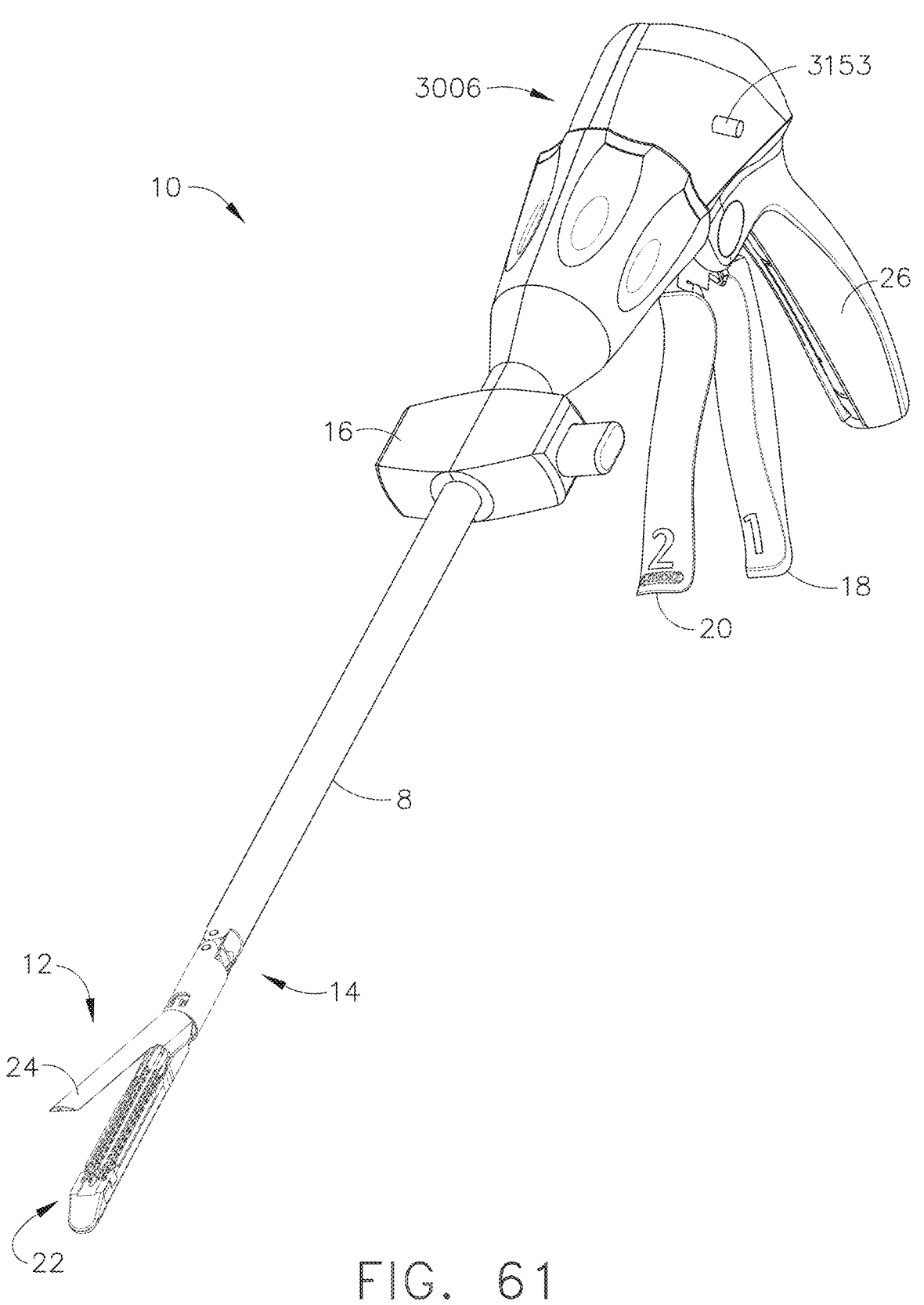

FIG. 61 shows one embodiment of a surgical instrument illustrating an example position for a start switch.

FIGS. 62-65 shown end effector arrangements according to various embodiments.

Figure 66:
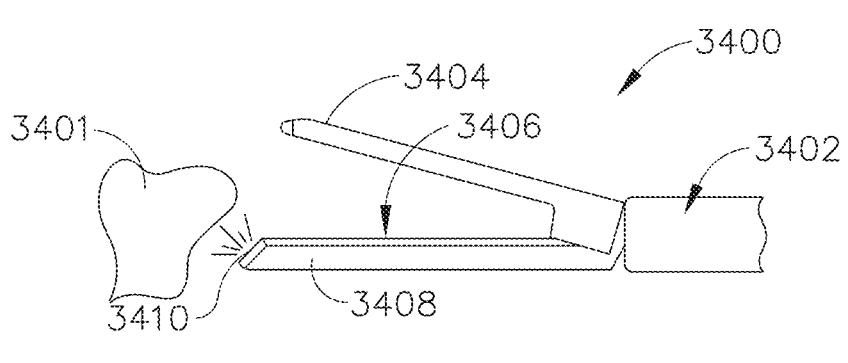
Figure 67:
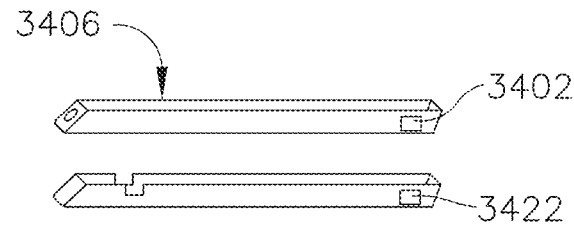

FIGS. 66-67 illustrate in general form, a distal end of a surgical stapler of various embodiments of the present invention which includes an anvil, a cartridge body, and channel.

Figure 68:
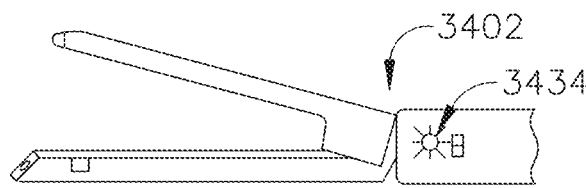

FIG. 68 illustrates the distal end of the surgical stapler of FIGS. 66-67 when an indicator positioned thereon.

Figure 69:
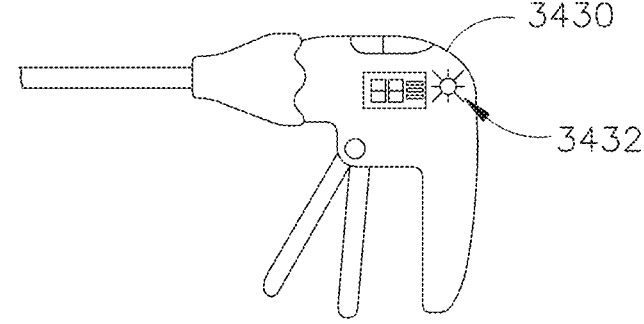

FIG. 69 illustrates the surgical stapler of FIGS. 66-67 with an indicator positioned on a handle thereof.

DETAILED DESCRIPTION

The owner of the subject application also owns the following U.S. Patent Applications that were filed on Jul. 29, 2010 and which are each herein incorporated by reference in their respective entirety:

U.S. patent application Ser. No. 12/846,249, entitled MOTOR DRIVEN SURGICAL FASTENER DEVICE WITH CUTTING MEMBER REVERSING MECHA-NISM, now U.S. Pat. No. 8,453,907; and U.S. patent application Ser. No. 12/846,237, entitled MOTOR DRIVEN SURGICAL FASTENER DEVICE WITH MECHANISMS FOR ADJUSTING A TISSUE GAP WITHIN THE END EFFECTOR, now U.S. Pat. No. 8,444,036.

Figure 1:
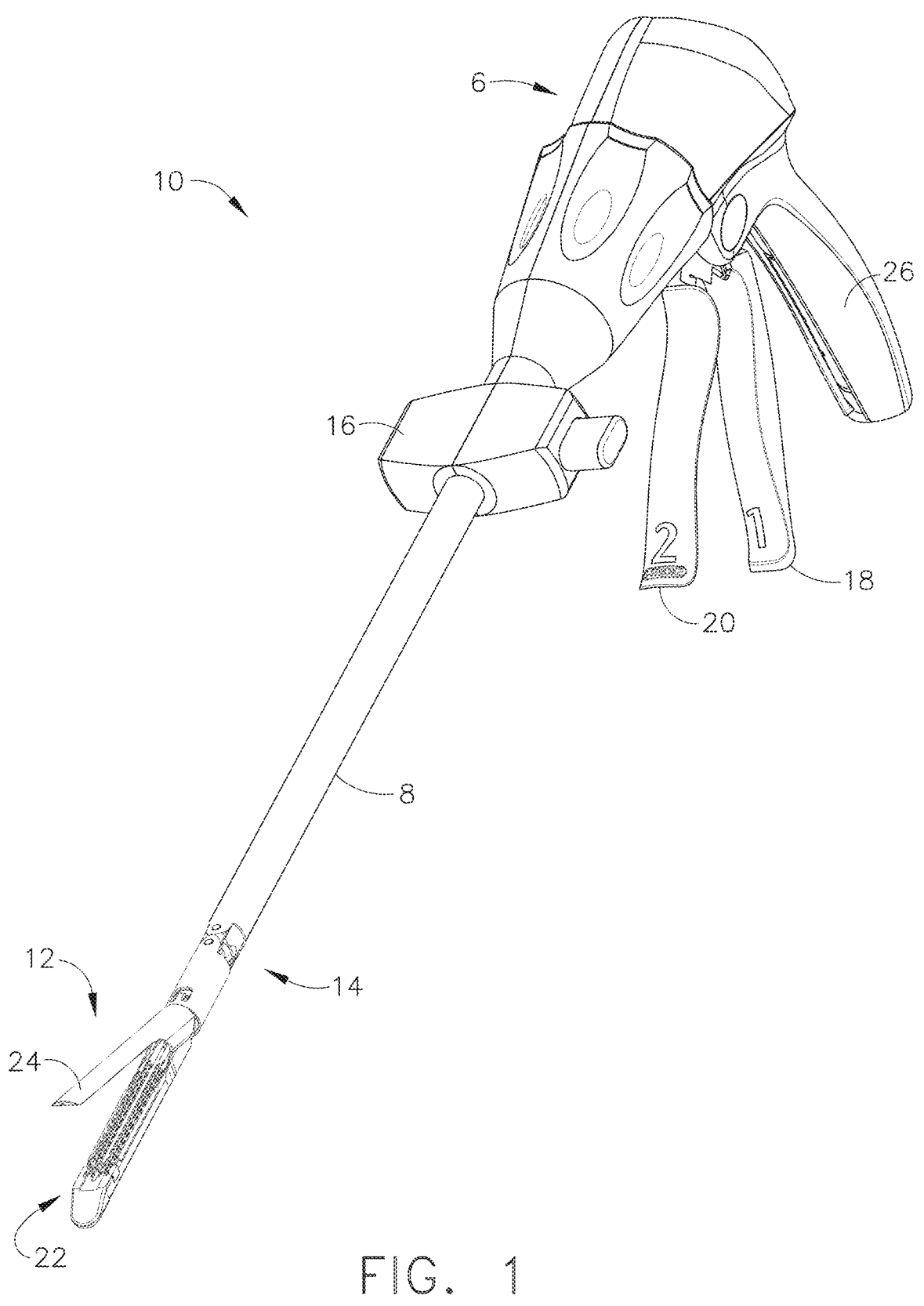
Figure 2:
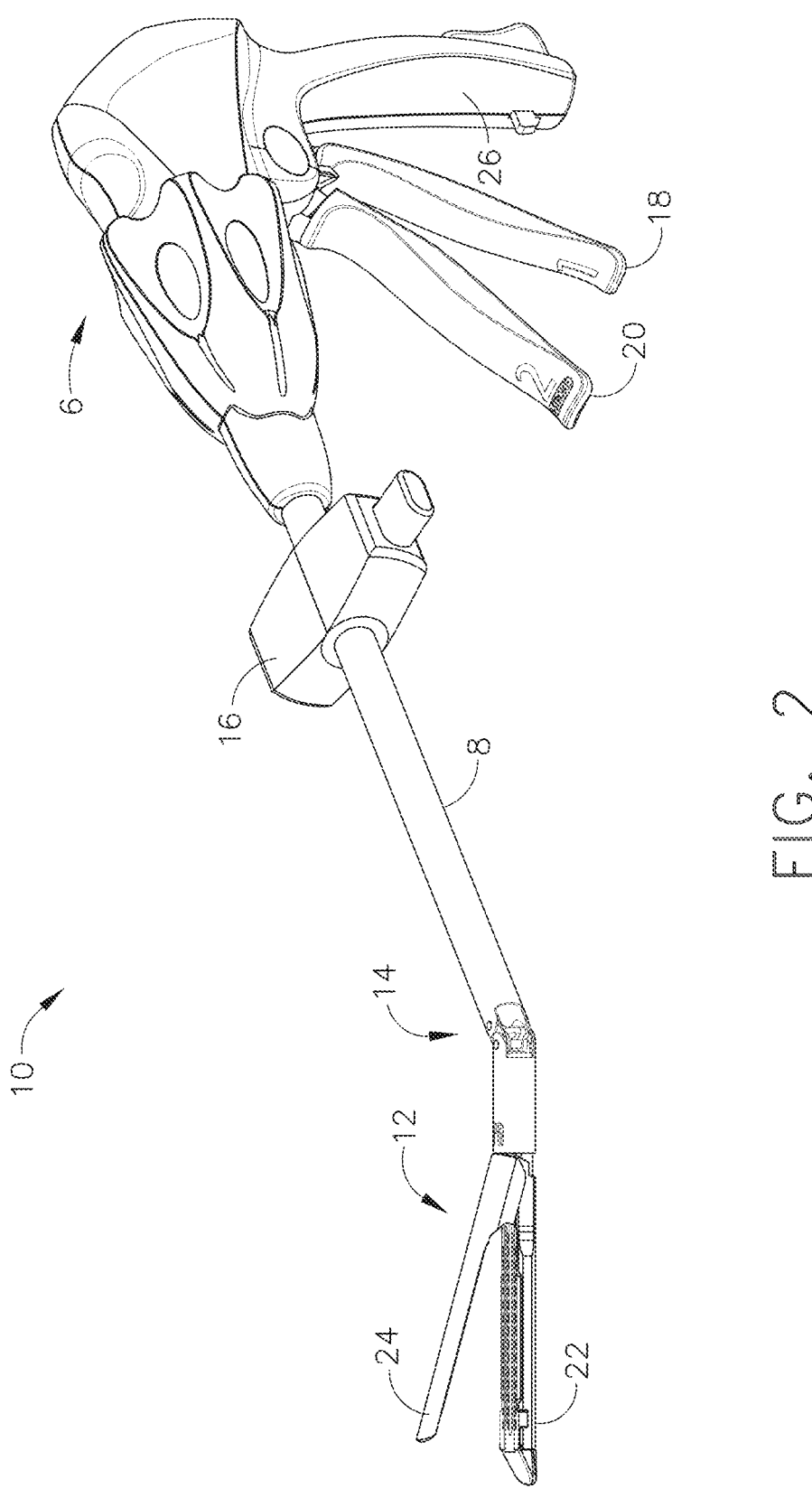

FIGS. 1 and 2 depict a surgical cutting and fastening instrument 10 according to various embodiments of the present invention. The illustrated embodiment is an endoscopic surgical instrument 10 and in general, the embodiments of the instrument 10 described herein are endoscopic surgical cutting and fastening instruments. It should be noted, however, that according to other embodiments of the present invention, the instrument 10 may be a non-endoscopic surgical cutting instrument, such as a laparoscopic instrument.

The surgical instrument 10 depicted in FIGS. 1 and 2 comprises a handle 6, a shaft 8, and an articulating end effector 12 pivotally connected to the shaft 8 at an articulation pivot 14. An articulation control 16 may be provided adjacent to the handle 6 to effect rotation of the end effector 12 about the articulation pivot 14. It will be appreciated that various embodiments may include a non-pivoting end effector, and therefore may not have an articulation pivot 14 or articulation control 16. Also, in the illustrated embodiment, the end effector 12 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by a preferably elongate shaft 8. In one embodiment, a clinician or operator of the instrument 10 may articulate the end effector 12 relative to the shaft 8 by utilizing the articulation control 16, as described in more detail in pending U.S. patent application Ser. No. 11/329,020, filed Jan. 10, 2006, entitled SUR-GICAL INSTRUMENT HAVING AN ARTICULATING END EFFECTOR, by Geoffrey C. Hueil et al., now U.S. Pat. No. 7,670,334 which is incorporated herein by reference in its entirety.

The end effector 12 includes in this example, among other things, a staple channel 22 and a pivotally translatable clamping member, such as an anvil 24, which are maintained at a spacing that assures effective stapling and severing of tissue clamped in the end effector 12. The handle 6 includes a pistol grip 26 toward which a closure trigger 18 is pivotally drawn by the clinician to cause clamping or closing of the anvil 24 towards the staple channel 22 of the end effector 12 to thereby clamp tissue positioned between the anvil 24 and channel 22. The firing trigger 20 is farther outboard of the closure trigger 18. Once the closure trigger 18 is locked in the closure position as further described below, the firing trigger 20 may rotate slightly toward the pistol grip 26 so that it can be reached by the operator using one hand. Then the operator may pivotally draw the firing trigger 20 toward the pistol grip 26 to cause the stapling and severing of clamped tissue in the end effector 12. In other embodiments, different types of clamping members besides the anvil 24 could be used, such as, for example, an opposing jaw, etc.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure, as described more fully below. A release button on the handle 6, when depressed may release the locked closure trigger 18. The release button may be implemented in various forms such as, for example, release button 30 shown in FIGS. 42-43, slide release button 160 shown in FIG. 14, and/or button 172 shown in FIG. 16.

FIGS. 3-6 show embodiments of a rotary-driven end effector 12 and shaft 8 according to various embodiments.

Figure 3:
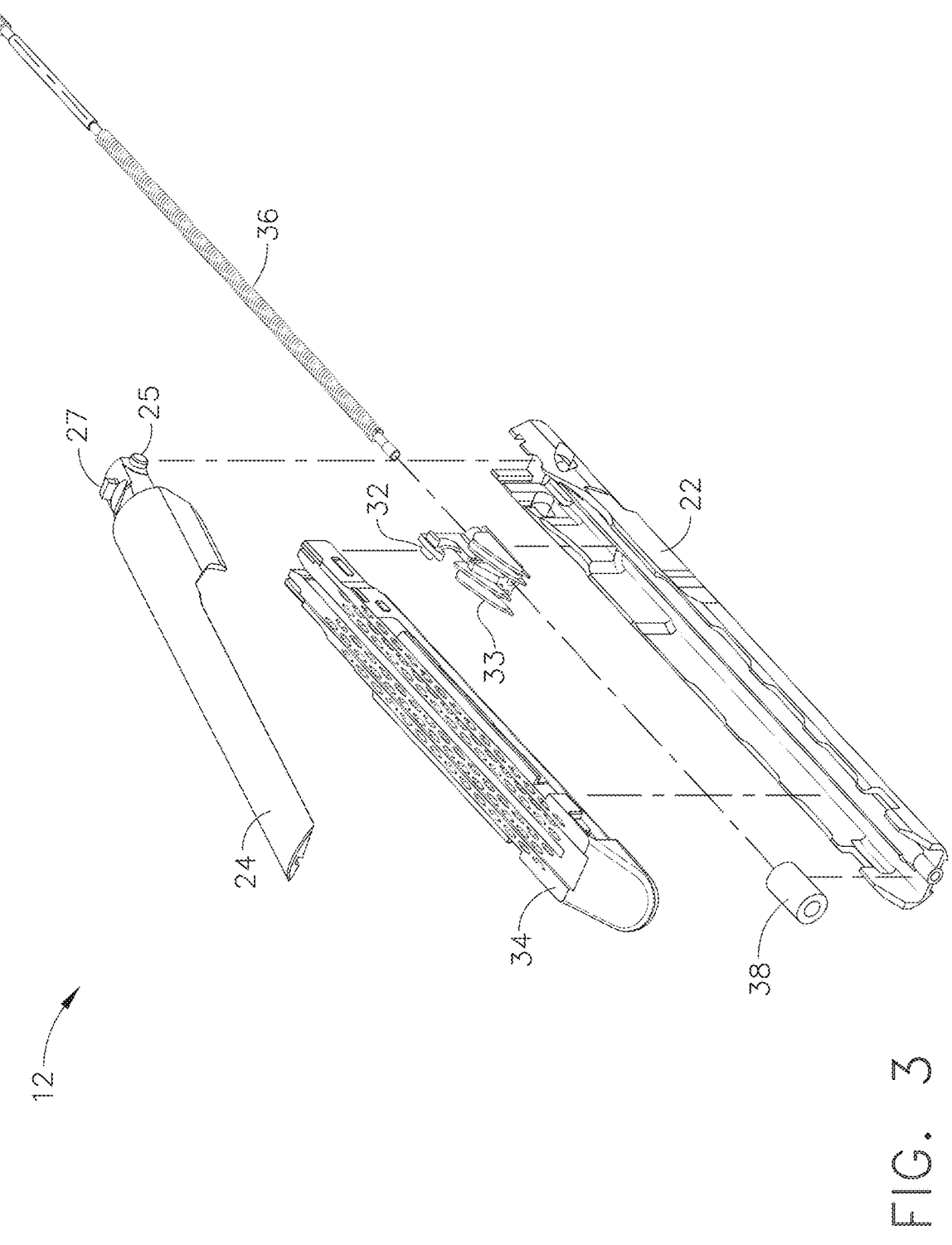
FIGS. 3-5 are exploded views of an end effector and shaft of the instrument according to various embodiments of the present invention.

FIG. 3 is an exploded view of the end effector 12 according to various embodiments. As shown in the illustrated embodiment, the end effector 12 may include, in addition to the previously-mentioned channel 22 and anvil 24, a cutting instrument 32, a sled 33, a staple cartridge 34 that is removably seated in the channel 22, and a helical screw shaft 36. The cutting instrument 32 may be, for example, a knife. The anvil 24 may be pivotably opened and closed at pivot pins 25 connected to the proximate end of the channel 22. The anvil 24 may also include a tab 27 at its proximate end that is inserted into a component of the mechanical closure system (described further below) to open and close the anvil 24. When the closure trigger 18 is actuated, that is, drawn in by a user of the instrument 10, the anvil 24 may pivot about the pivot pins 25 into the clamped or closed position. If clamping of the end effector 12 is satisfactory, the operator may actuate the firing trigger 20, which, as explained in more detail below, causes the knife 32 and sled 33 to travel longitudinally along the channel 22, thereby cutting tissue clamped within the end effector 12. The movement of the sled 33 along the channel 22 causes the staples (not shown) of the staple cartridge 34 to be driven through the severed tissue and against the closed anvil 24, which turns the staples to fasten the severed tissue. In various embodiments, the sled 33 may be an integral component of the cartridge 34. U.S. Pat. No. 6,978,921, entitled SURGICAL STAPLING INSTRUMENT INCORPORATING AN E-BEAM FIRING MECHANISM to Shelton, I V et al., which is incorporated herein by reference in its entirety, provides more details about such two-stroke cutting and fastening instruments. The sled 33 may be part of the cartridge 34, such that when the knife 32 retracts following the cutting operation, the sled 33 does not retract.

It should be noted that although the embodiments of the instrument 10 described herein employ an end effector 12 that staples the severed tissue, in other embodiments different techniques for fastening or sealing the severed tissue may be used. For example, end effectors that use RF energy or adhesives to fasten the severed tissue may also be used. U.S. Pat. No. 5,709,680 entitled ELECTROSURGICAL HEMOSTATIC DEVICE to Yates et al., and U.S. Pat. No. 5,688,270 entitled ELECTROSURGICAL HEMOSTATIC DEVICE WITH RECESSED AND/OR OFFSET ELECTRODES to Yates et al., which are incorporated herein by reference, disclose an endoscopic cutting instrument that uses RF energy to seal the severed tissue. U.S. patent application Ser. No. 11/267,811 to Jerome R. Morgan, et. al, now U.S. Pat. No. 7,673,783 and U.S. patent application Ser. No. 11/267,383 to Frederick E. Shelton, I V, et. al, now U.S. Pat. No. 7,607,557 which are also incorporated herein by reference in their respective entireties disclose cutting instruments that uses adhesives to fasten the severed tissue. Accordingly, although the description herein refers to cutting/stapling operations and the like below, it should be recognized that this is an exemplary embodiment and is not meant to be limiting. Other tissue fastening techniques may also be used.

Figure 4:
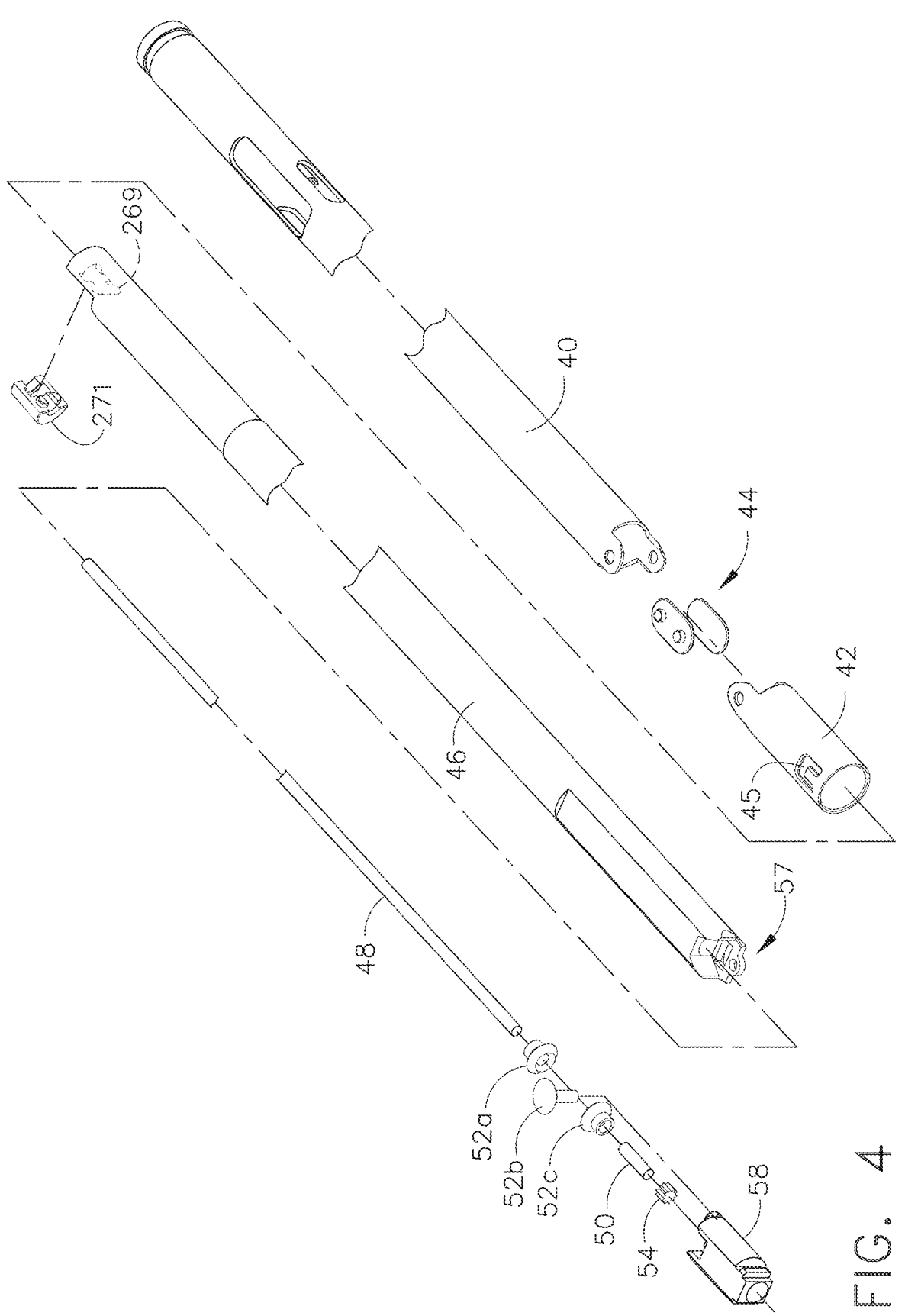
Figure 5:
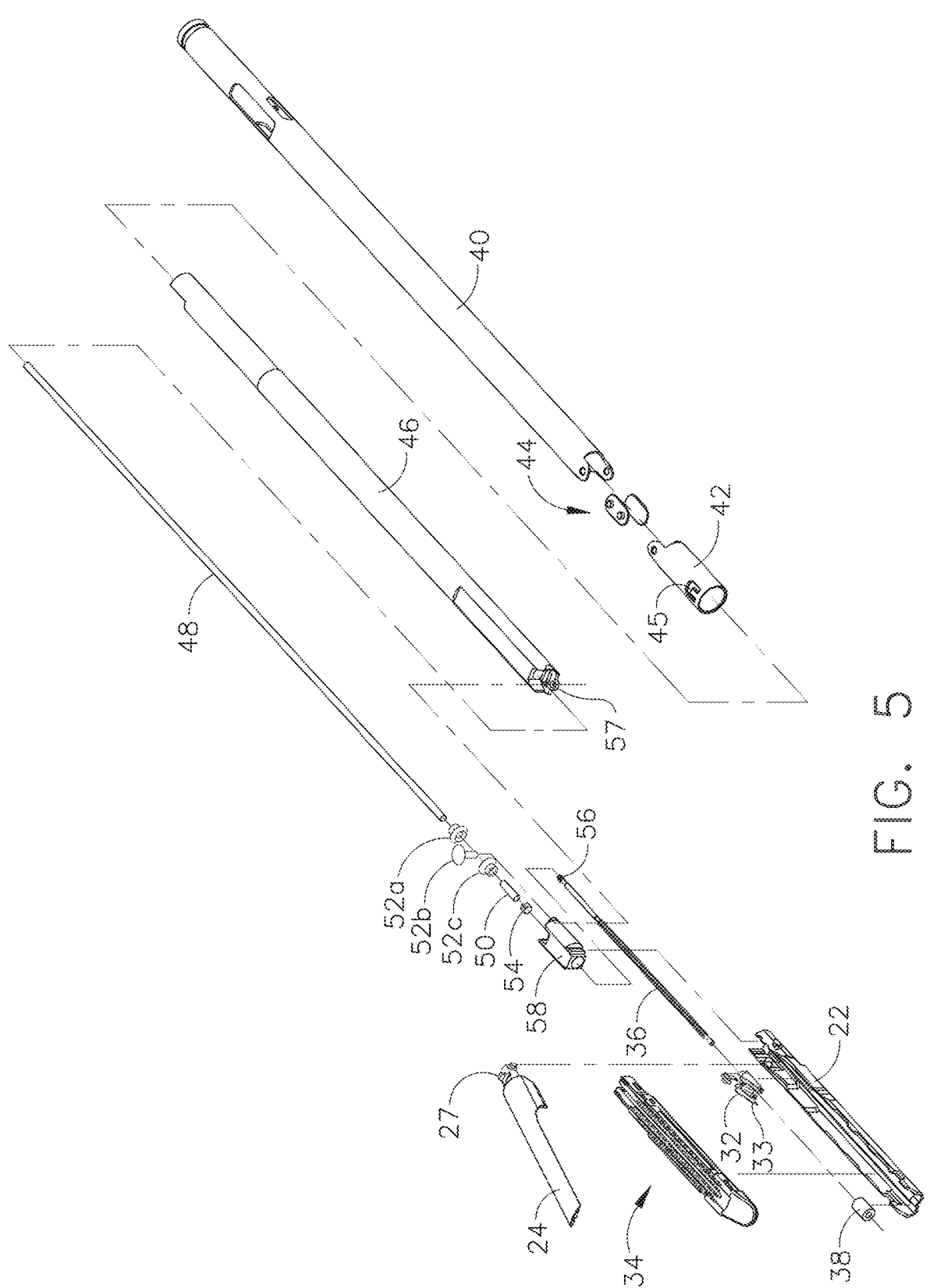
Figure 6:
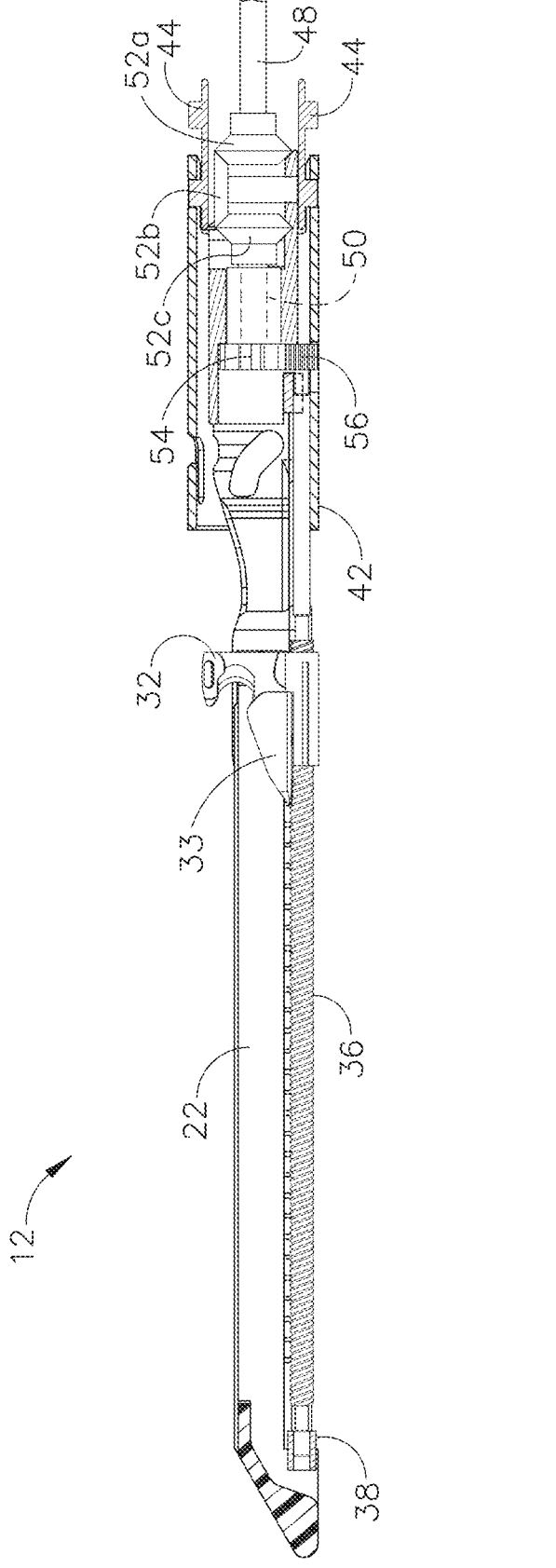
FIG. 6 is a side view of the end effector according to various embodiments of the present invention.
Figure 7:
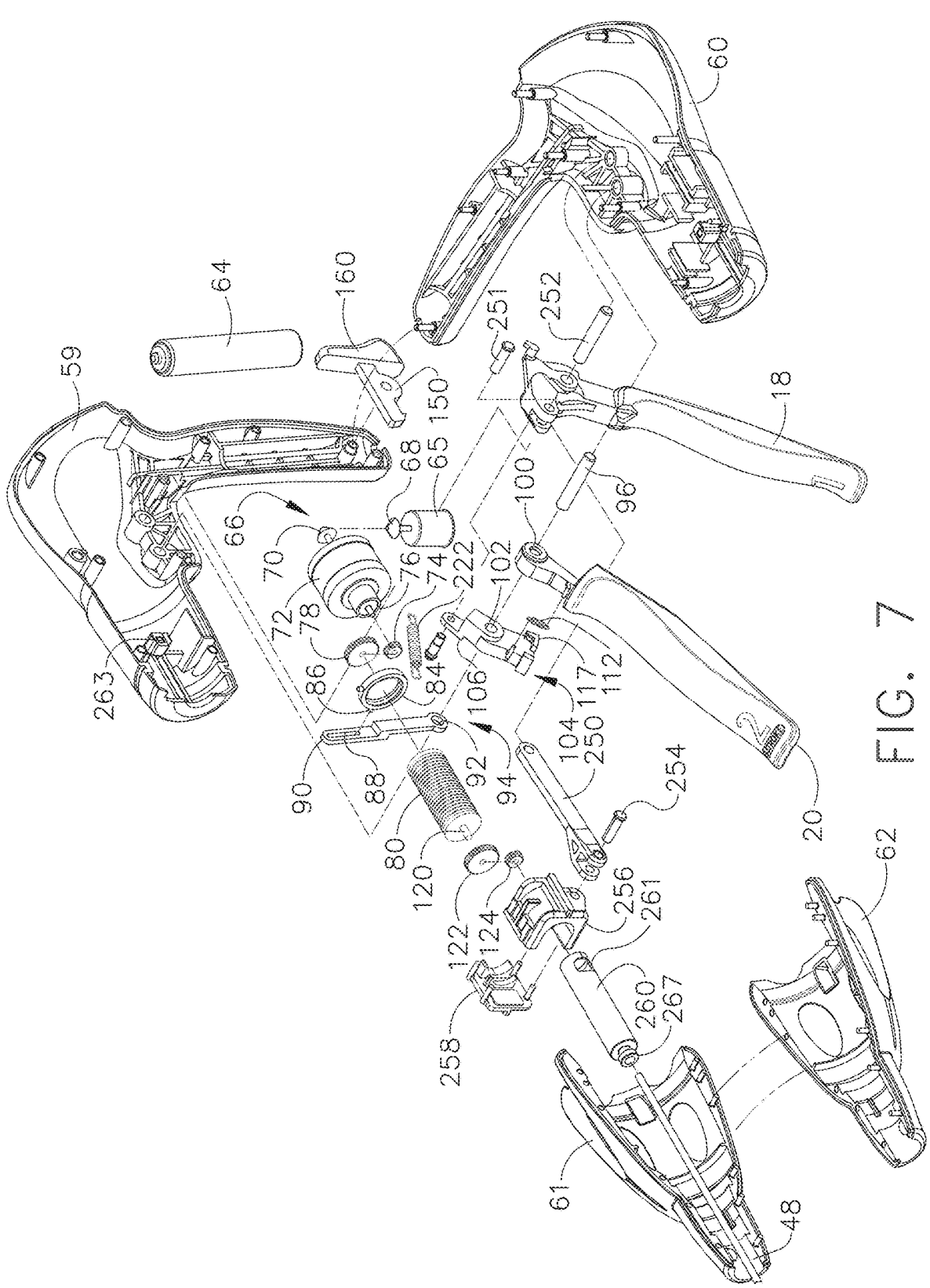
FIG. 7 is an exploded view of the handle of the instrument according to various embodiments of the present invention.

FIGS. 4 and 5 are exploded views and FIG. 6 is a side view of the end effector 12 and shaft 8 according to various embodiments. As shown in the illustrated embodiment, the shaft 8 may include a proximate closure tube 40 and a distal closure tube 42 pivotably linked by a pivot link 44. The distal closure tube 42 includes an opening 45 into which the tab 27 on the anvil 24 is inserted in order to open and close the anvil 24, as further described below. Disposed inside the closure tubes 40, 42 may be a proximate spine tube 46. Disposed inside the proximate spine tube 46 may be a main rotational (or proximate) drive shaft 48 that communicates with a secondary (or distal) drive shaft 50 via a bevel gear assembly 52. The secondary drive shaft 50 is connected to a drive gear 54 that engages a proximate drive gear 56 of the helical screw shaft 36. The vertical bevel gear 52b may sit and pivot in an opening 57 in the distal end of the proximate spine tube 46. A distal spine tube 58 may be used to enclose the secondary drive shaft 50 and the drive gears 54, 56. Collectively, the main drive shaft 48, the secondary drive shaft 50, and the articulation assembly (e.g., the bevel gear assembly 52a-c) are sometimes referred to herein as the "main drive shaft assembly."

A bearing 38, positioned at a distal end of the staple channel 22, receives the helical drive screw 36, allowing the helical drive screw 36 to freely rotate with respect to the channel 22. The helical screw shaft 36 may interface a threaded opening (not shown) of the knife 32 such that rotation of the shaft 36 causes the knife 32 to translate distally or proximately (depending on the direction of the rotation) through the staple channel 22. Accordingly, when the main drive shaft 48 is caused to rotate by actuation of the firing trigger 20 (as explained in more detail below), the bevel gear assembly 52a-c causes the secondary drive shaft 50 to rotate, which in turn, because of the engagement of the drive gears 54, 56, causes the helical screw shaft 36 to rotate, which causes the knife driving member 32 to travel longitudinally along the channel 22 to cut any tissue clamped within the end effector 12. The sled 33 may be made of, for example, plastic, and may have a sloped distal surface. As the sled 33 traverses the channel 22, the sloped forward surface may push up or drive the staples in the staple cartridge through the clamped tissue and against the anvil 24. The anvil 24 turns the staples, thereby stapling the severed tissue. When the knife 32 is retracted, the knife 32 and sled 33 may become disengaged, thereby leaving the sled 33 at the distal end of the channel 22.

As described above, because of the lack of user feedback for the cutting/stapling operation, there is a general lack of acceptance among physicians of motor-driven endocutters where the cutting/stapling operation is actuated by merely pressing a button. In contrast, embodiments of the present invention provide a motor-driven endocutter with user-feedback of the deployment, force and/or position of the cutting instrument 32 in end effector 12.

FIGS. 7-10 illustrate an exemplary embodiment of a motor-driven endocutter, and in particular the handle thereof, that provides user-feedback regarding the deployment and loading force of the cutting instrument 32 in the end effector 12. In addition, the embodiment may use power provided by the user in retracting the firing trigger 20 to power the device (a so-called "power assist" mode). The embodiment may be used with the rotary driven end effector 12 and shaft 8 embodiments described above. As shown in the illustrated embodiment, the handle 6 includes exterior lower side pieces 59, 60 and exterior upper side pieces 61, 62 that fit together to form, in general, the exterior of the handle 6. A battery 64, such as a Li ion battery, may be provided in the pistol grip portion 26 of the handle 6. The battery 64 powers a motor 65 disposed in an upper portion of the pistol grip portion 26 of the handle 6. According to various embodiments, the motor 65 may be a DC brushed driving motor having a maximum rotation of, approximately, 5000 RPM. The motor 65 may drive a 90° bevel gear assembly 66 comprising a first bevel gear 68 and a second bevel gear 70. The bevel gear assembly 66 may drive a planetary gear assembly 72. The planetary gear assembly 72 may include a pinion gear 74 connected to a drive shaft 76.

The pinion gear 74 may drive a mating ring gear 78 that drives a helical gear drum 80 via a drive shaft 82. A ring 84 may be threaded on the helical gear drum 80. Thus, when the motor 65 rotates, the ring 84 is caused to travel along the helical gear drum 80 by means of the interposed bevel gear assembly 66, planetary gear assembly 72 and ring gear 78.

The handle 6 may also include a run motor sensor 110 (see FIG. 10) in communication with the firing trigger 20 to detect when the firing trigger 20 has been drawn in (or "closed") toward the pistol grip portion 26 of the handle 6 by the operator to thereby actuate the cutting/stapling operation by the end effector 12. The sensor 110 may be a proportional sensor such as, for example, a rheostat or variable resistor. When the firing trigger 20 is drawn in, the sensor 110 detects the movement, and sends an electrical signal indicative of the voltage (or power) to be supplied to the motor 65. When the sensor 110 is a variable resistor or the like, the rotation of the motor 65 may be generally proportional to the amount of movement of the firing trigger 20. That is, if the operator only draws or closes the firing trigger 20 in a little bit, the rotation of the motor 65 is relatively low. When the firing trigger 20 is fully drawn in (or in the fully closed position), the rotation of the motor 65 is at its maximum. In other words, the harder the user pulls on the firing trigger 20, the more voltage is applied to the motor 65, causing greater rates of rotation.

The handle 6 may include a middle handle piece 104 adjacent to the upper portion of the firing trigger 20. The handle 6 also may comprise a bias spring 112 connected between posts on the middle handle piece 104 and the firing trigger 20. The bias spring 112 may bias the firing trigger 20 to its fully open position. In that way, when the operator releases the firing trigger 20, the bias spring 112 will pull the firing trigger 20 to its open position, thereby removing actuation of the sensor 110, thereby stopping rotation of the motor 65. Moreover, by virtue of the bias spring 112, any time a user closes the firing trigger 20, the user will experience resistance to the closing operation, thereby providing the user with feedback as to the amount of rotation exerted by the motor 65. Further, the operator could stop retracting the firing trigger 20 to thereby remove force from the sensor 100, to thereby stop the motor 65. As such, the user may stop the deployment of the end effector 12, thereby providing a measure of control of the cutting/fastening operation to the operator.

The distal end of the helical gear drum 80 includes a distal drive shaft 120 that drives a ring gear 122, which mates with a pinion gear 124. The pinion gear 124 is connected to the main drive shaft 48 of the main drive shaft assembly. In that way, rotation of the motor 65 causes the main drive shaft assembly to rotate, which causes actuation of the end effector 12, as described above.

The ring 84 threaded on the helical gear drum 80 may include a post 86 that is disposed within a slot 88 of a slotted arm 90. The slotted arm 90 has an opening 92 its opposite end 94 that receives a pivot pin 96 that is connected between the handle exterior side pieces 59, 60. The pivot pin 96 is also disposed through an opening 100 in the firing trigger 20 and an opening 102 in the middle handle piece 104.

In addition, the handle 6 may include a reverse motor sensor (or end-of-stroke sensor) 130 and a stop motor (or beginning-of-stroke) sensor 142. In various embodiments, the reverse motor sensor 130 may be a limit switch located at the distal end of the helical gear drum 80 such that the ring 84 threaded on the helical gear drum 80 contacts and trips the reverse motor sensor 130 when the ring 84 reaches the distal end of the helical gear drum 80. The reverse motor sensor 130, when activated, sends a signal to the motor 65 to reverse its rotation direction, thereby withdrawing the knife 32 of the end effector 12 following the cutting operation.

The stop motor sensor 142 may be, for example, a normally-closed limit switch. In various embodiments, it may be located at the proximate end of the helical gear drum 80 so that the ring 84 trips the switch 142 when the ring 84 reaches the proximate end of the helical gear drum 80.

In operation, when an operator of the instrument 10 pulls back the firing trigger 20, the sensor 110 detects the deployment of the firing trigger 20 and sends a signal to the motor 65 to cause forward rotation of the motor 65, for example, at a rate proportional to how hard the operator pulls back the firing trigger 20. The forward rotation of the motor 65 in turn causes the ring gear 78 at the distal end of the planetary gear assembly 72 to rotate, thereby causing the helical gear drum 80 to rotate, causing the ring 84 threaded on the helical gear drum 80 to travel distally along the helical gear drum 80. The rotation of the helical gear drum 80 also drives the main drive shaft assembly as described above, which in turn causes deployment of the knife 32 in the end effector 12. That is, the knife 32 and sled 33 are caused to traverse the channel 22 longitudinally, thereby cutting tissue clamped in the end effector 12. Also, the stapling operation of the end effector 12 is caused to happen in embodiments where a stapling-type end effector 12 is used.

By the time the cutting/stapling operation of the end effector 12 is complete, the ring 84 on the helical gear drum 80 will have reached the distal end of the helical gear drum 80, thereby causing the reverse motor sensor 130 to be tripped, which sends a signal to the motor 65 to cause the motor 65 to reverse its rotation. This in turn causes the knife 32 to retract, and also causes the ring 84 on the helical gear drum 80 to move back to the proximate end of the helical gear drum 80.

Figure 8:
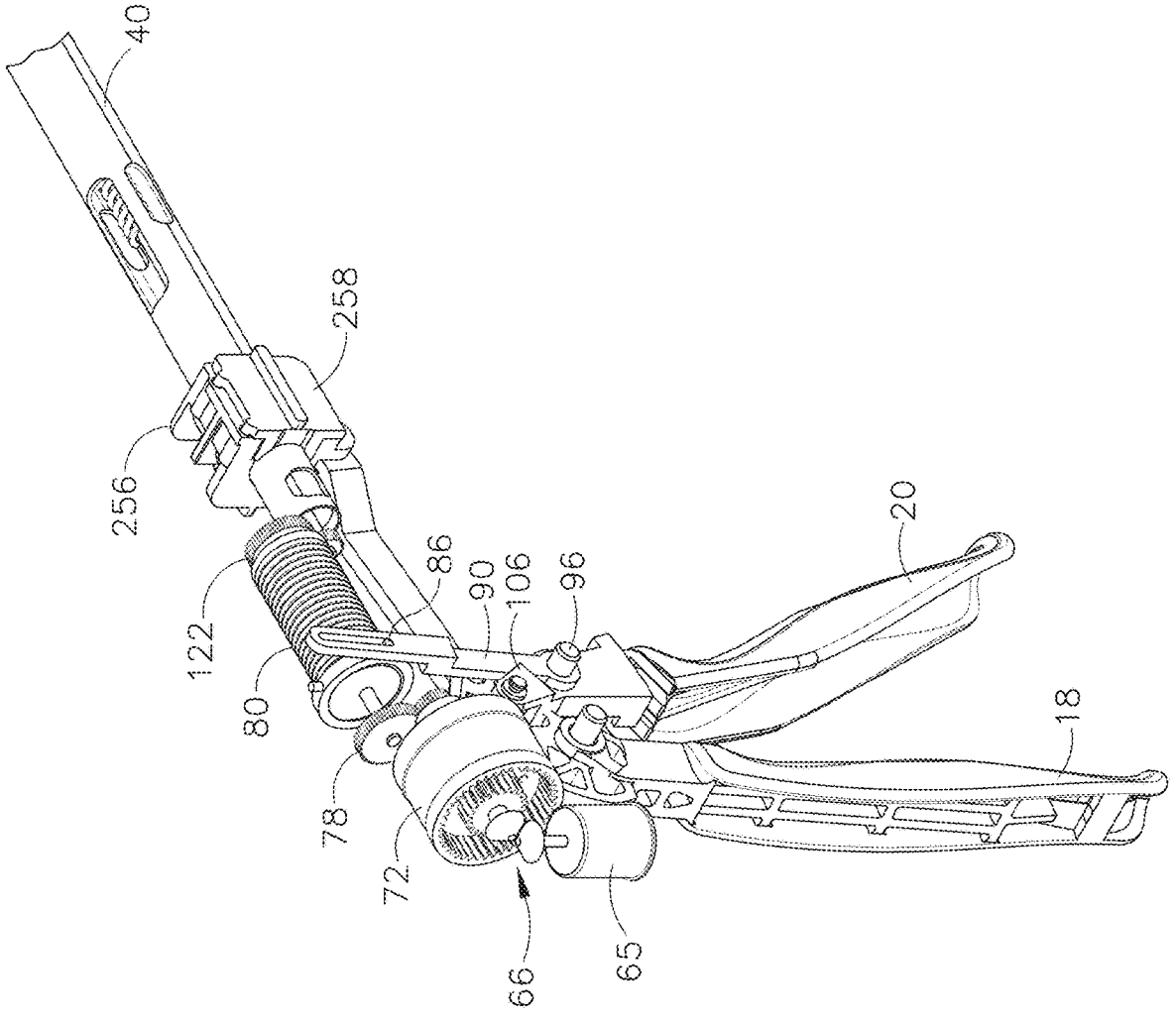
FIGS. 8 and 9 are partial perspective views of the handle according to various embodiments of the present invention.
Figure 9:
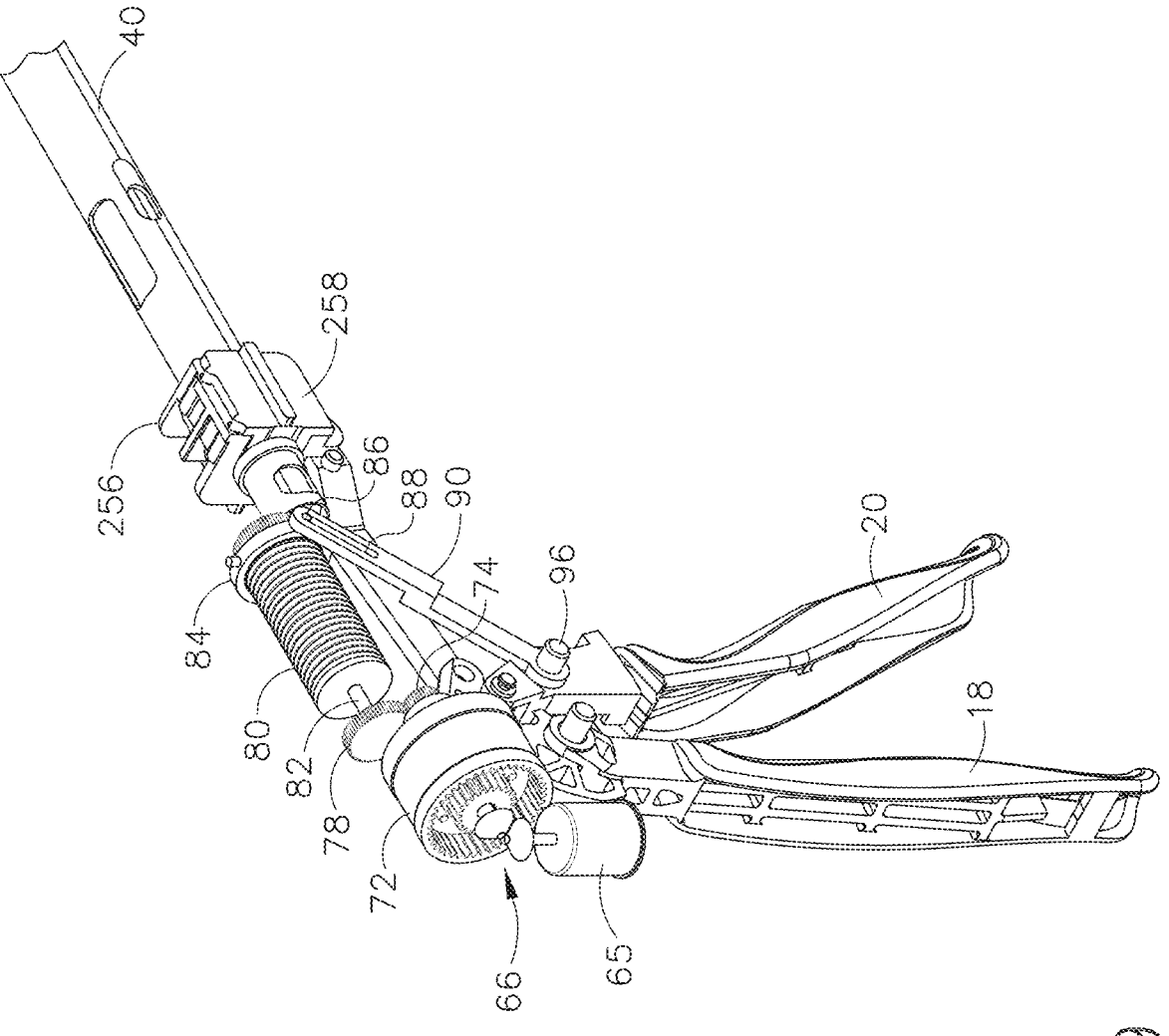

The middle handle piece 104 includes a backside shoulder 106 that engages the slotted arm 90 as best shown in FIGS. 8 and 9. The middle handle piece 104 also has a forward motion stop 107 that engages the firing trigger 20. The movement of the slotted arm 90 is controlled, as explained above, by rotation of the motor 65. When the slotted arm 90 rotates counter clockwise as the ring 84 travels from the proximate end of the helical gear drum 80 to the distal end, the middle handle piece 104 will be free to rotate counter clockwise. Thus, as the user draws in the firing trigger 20, the firing trigger 20 will engage the forward motion stop 107 of the middle handle piece 104, causing the middle handle piece 104 to rotate counter clockwise. Due to the backside shoulder 106 engaging the slotted arm 90, however, the middle handle piece 104 will only be able to rotate counter clockwise as far as the slotted arm 90 permits. In that way, if the motor 65 should stop rotating for some reason, the slotted arm 90 will stop rotating, and the user will not be able to further draw in the firing trigger 20 because the middle handle piece 104 will not be free to rotate counter clockwise due to the slotted arm 90.

Figure 10:
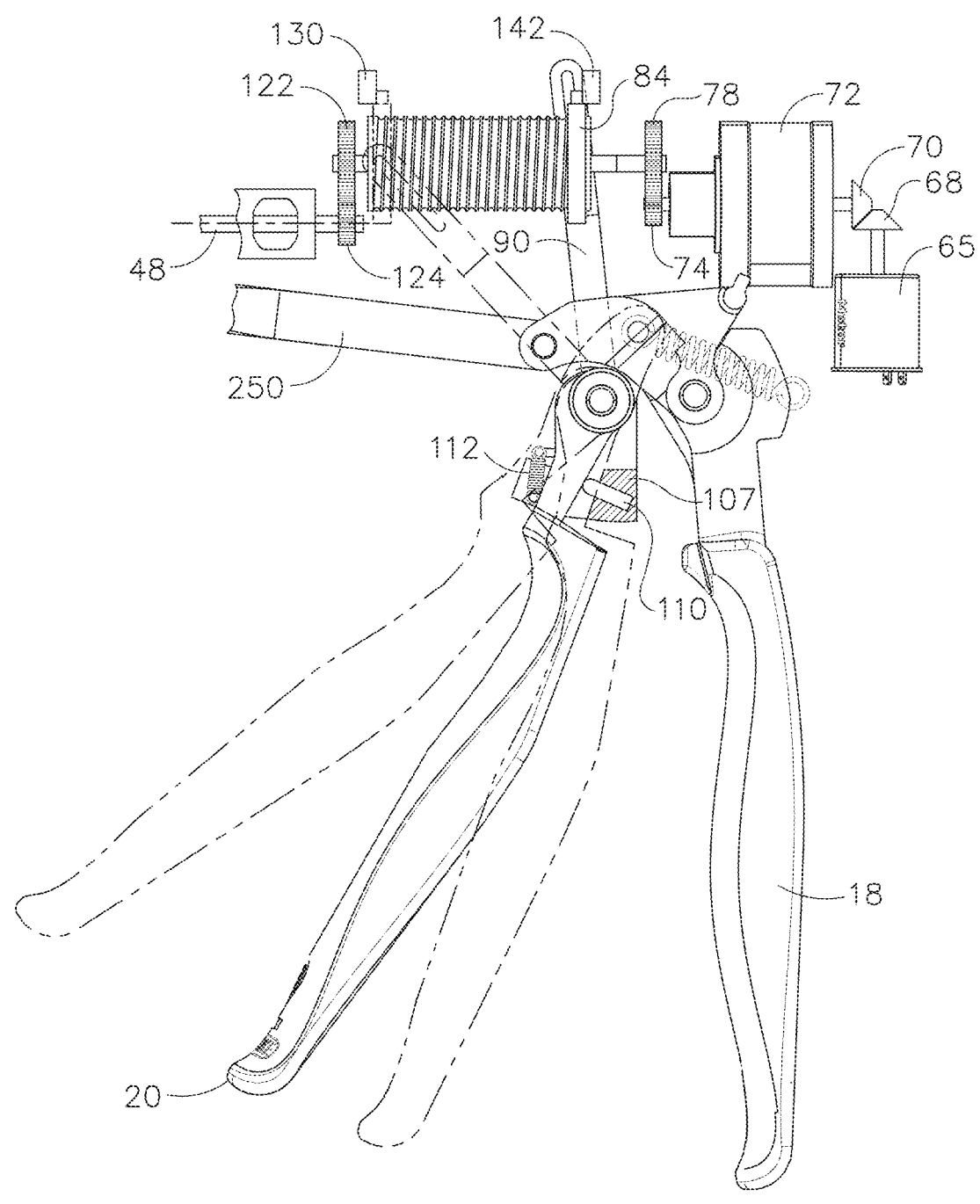
FIG. 10 is a side view of the handle according to various embodiments of the present invention.
Figure 10A:
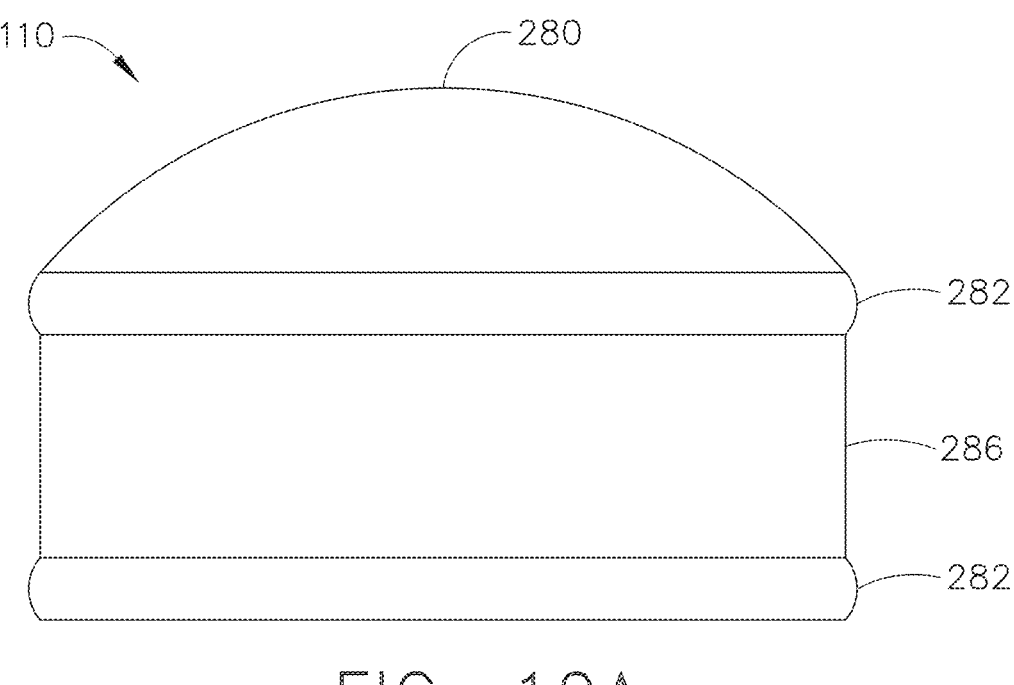
FIGS. 10A and 10B illustrate a proportional sensor that may be used according to various embodiments of the present invention.
Figure 10B:
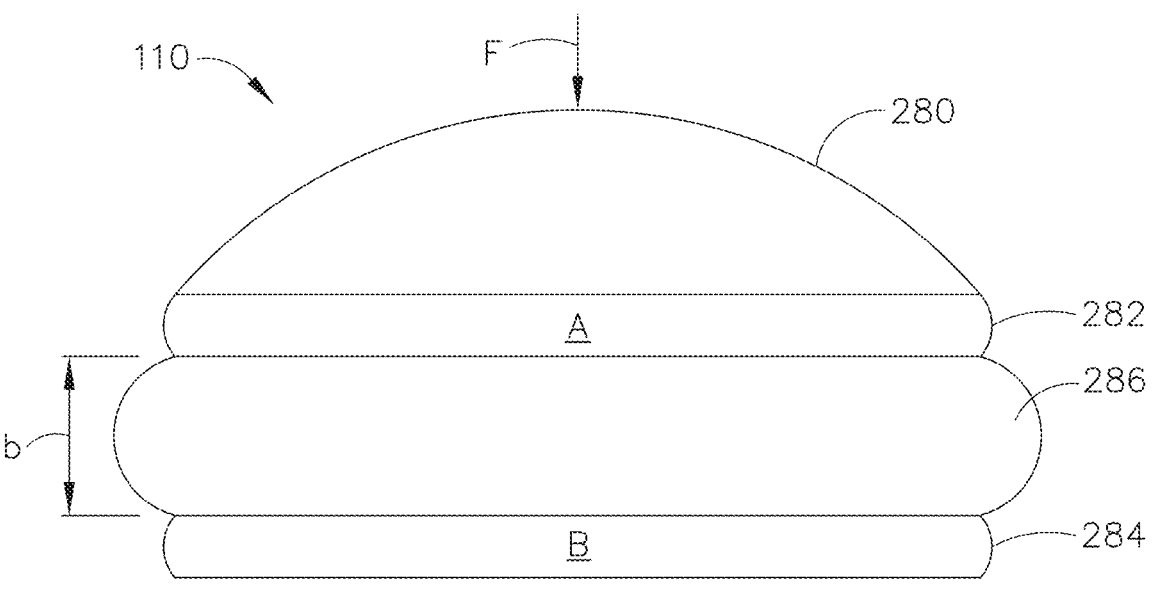

FIGS. 10A and 10B illustrate two states of a variable sensor that may be used as the run motor sensor 110 according to various embodiments of the present invention. The sensor 110 may include a face portion 280, a first electrode (A) 282, a second electrode (B) 284, and a compressible dielectric material 286 between the electrodes 282, 284, such as, for example, an electroactive polymer (EAP). The sensor 110 may be positioned such that the face portion 280 contacts the firing trigger 20 when retracted. Accordingly, when the firing trigger 20 is retracted, the dielectric material 286 is compressed, as shown in FIG. 10B, such that the electrodes 282, 284 are closer together. Since the distance "b" between the electrodes 282, 284 is directly related to the impedance between the electrodes 282, 284, the greater the distance the more impedance, and the closer the distance the less impedance. In that way, the amount that the dielectric 286 is compressed due to retraction of the firing trigger 20 is proportional to the impedance between the electrodes 282, 284, which can be used to proportionally control the motor 65.

Components of an exemplary closure system for closing (or clamping) the anvil 24 of the end effector 12 by retracting the closure trigger 18 are also shown in FIGS. 7-10. In the illustrated embodiment, the closure system includes a yoke 250 connected to the closure trigger 18 by a pivot pin 251 inserted through aligned openings in both the closure trigger 18 and the yoke 250. A pivot pin 252, about which the closure trigger 18 pivots, is inserted through another opening in the closure trigger 18 which is offset from where the pin 251 is inserted through the closure trigger 18. Thus, retraction of the closure trigger 18 causes the upper part of the closure trigger 18, to which the yoke 250 is attached via the pin 251, to rotate counterclockwise. The distal end of the yoke 250 is connected, via a pin 254, to a first closure bracket 256. The first closure bracket 256 connects to a second closure bracket 258. Collectively, the closure brackets 256, 258 define an opening in which the proximate end of the proximate closure tube 40 (see FIG. 4) is seated and held such that longitudinal movement of the closure brackets 256, 258 causes longitudinal motion by the proximate closure tube 40. The instrument 10 also includes a closure rod 260 disposed inside the proximate closure tube 40. The closure rod 260 may include a window 261 into which a post 263 on one of the handle exterior pieces, such as exterior lower side piece 59 in the illustrated embodiment, is disposed to fixedly connect the closure rod 260 to the handle 6. In that way, the proximate closure tube 40 is capable of moving longitudinally relative to the closure rod 260. The closure rod 260 may also include a distal collar 267 that fits into a cavity 269 in proximate spine tube 46 and is retained therein by a cap 271 (see FIG. 4).

In operation, when the yoke 250 rotates due to retraction of the closure trigger 18, the closure brackets 256, 258 cause the proximate closure tube 40 to move distally (i.e., away from the handle end of the instrument 10), which causes the distal closure tube 42 to move distally, which causes the anvil 24 to rotate about the pivot pins 25 into the clamped or closed position. When the closure trigger 18 is unlocked from the locked position, the proximate closure tube 40 is caused to slide proximately, which causes the distal closure tube 42 to slide proximately, which, by virtue of the tab 27 being inserted in the window 45 of the distal closure tube 42, causes the anvil 24 to pivot about the pivot pins 25 into the open or unclamped position. In that way, by retracting and locking the closure trigger 18, an operator may clamp tissue between the anvil 24 and channel 22, and may unclamp the tissue following the cutting/stapling operation by unlocking the closure trigger 20 from the locked position.

Figure 11:
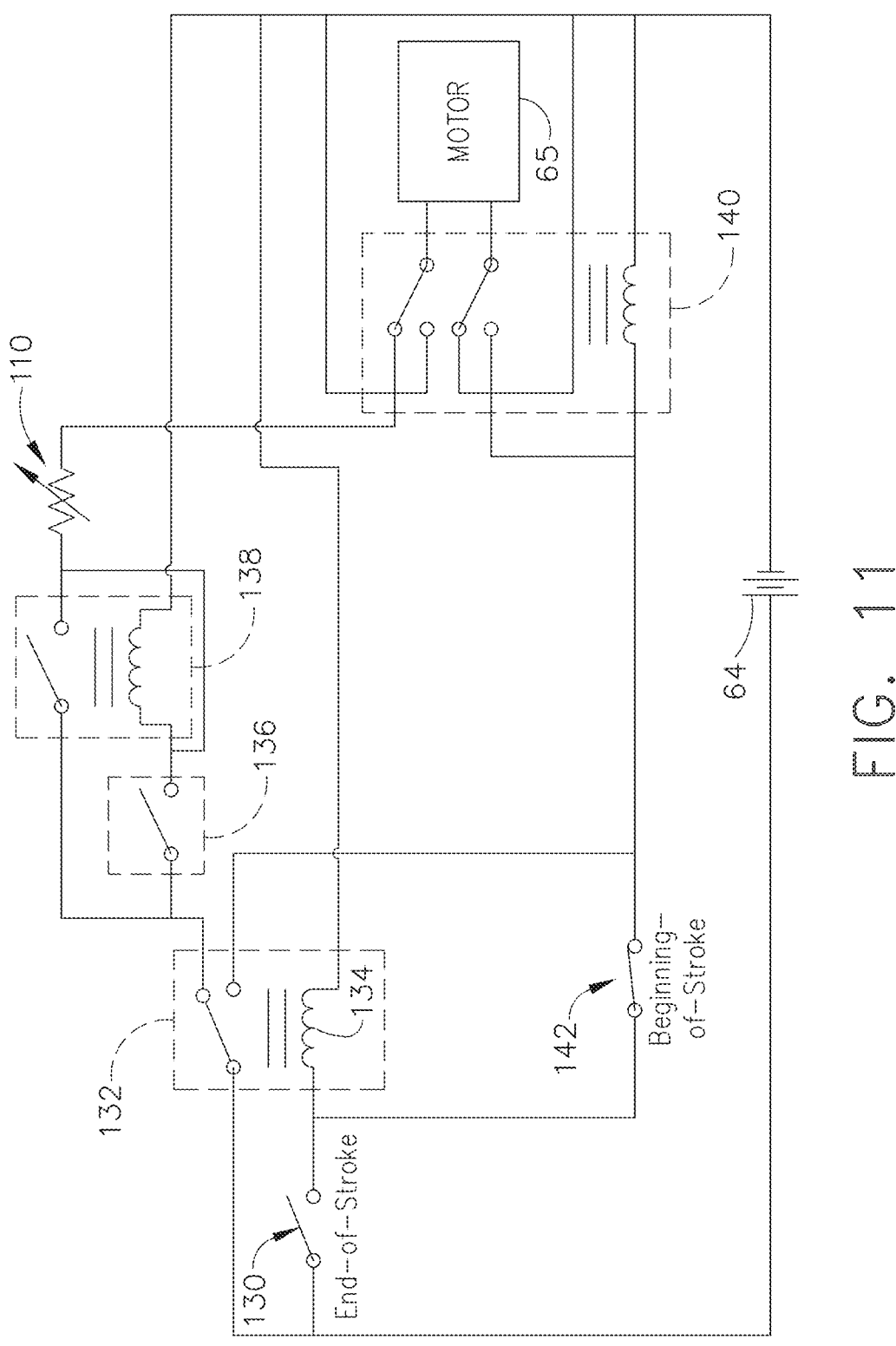
FIG. 11 is a schematic diagram of a circuit that may be used in the instrument according to various embodiments of the present invention.

FIG. 11 is a schematic diagram of an electrical circuit of the instrument 10 according to various embodiments of the present invention. When an operator initially pulls in the firing trigger 20 after locking the closure trigger 18, the sensor 110 is activated, allowing current to flow therethrough. If the normally-open reverse motor sensor switch 130 is open (meaning the end of the end effector stroke has not been reached), current will flow to a single pole, double throw relay 132. Since the reverse motor sensor switch 130 is not closed, the inductor 134 of the relay 132 will not be energized, so the relay 132 will be in its non-energized state. The circuit also includes a cartridge lockout sensor 136. If the end effector 12 includes a staple cartridge 34, the sensor 136 will be in the closed state, allowing current to flow. Otherwise, if the end effector 12 does not include a staple cartridge 34, the sensor 136 will be open, thereby preventing the battery 64 from powering the motor 65.

When the staple cartridge 34 is present, the sensor 136 is closed, which energizes a single pole, single throw relay 138. When the relay 138 is energized, current flows through the relay 136, through the variable resistor sensor 110, and to the motor 65 via a double pole, double throw relay 140, thereby powering the motor 65 and allowing it to rotate in the forward direction.

When the end effector 12 reaches the end of its stroke, the reverse motor sensor 130 will be activated, thereby closing the switch 130 and energizing the relay 134. This causes the relay 134 to assume its energized state (not shown in FIG. 13), which causes current to bypass the cartridge lockout sensor 136 and variable resistor 110, and instead causes current to flow to both the normally-closed double pole, double throw relay 140 and back to the motor 65, but in a manner, via the relay 140, that causes the motor 65 to reverse its rotational direction.

Because the stop motor sensor switch 142 is normally-closed, current will flow back to the relay 134 to keep it closed until the switch 142 opens. When the knife 32 is fully retracted, the stop motor sensor switch 142 is activated, causing the switch 142 to open, thereby removing power from the motor 65.

In other embodiments, rather than a proportional-type sensor 110, an on-off type sensor could be used. In such embodiments, the rate of rotation of the motor 65 would not be proportional to the force applied by the operator. Rather, the motor 65 would generally rotate at a constant rate. But the operator would still experience force feedback because the firing trigger 20 is geared into the gear drive train.

Figure 11A:
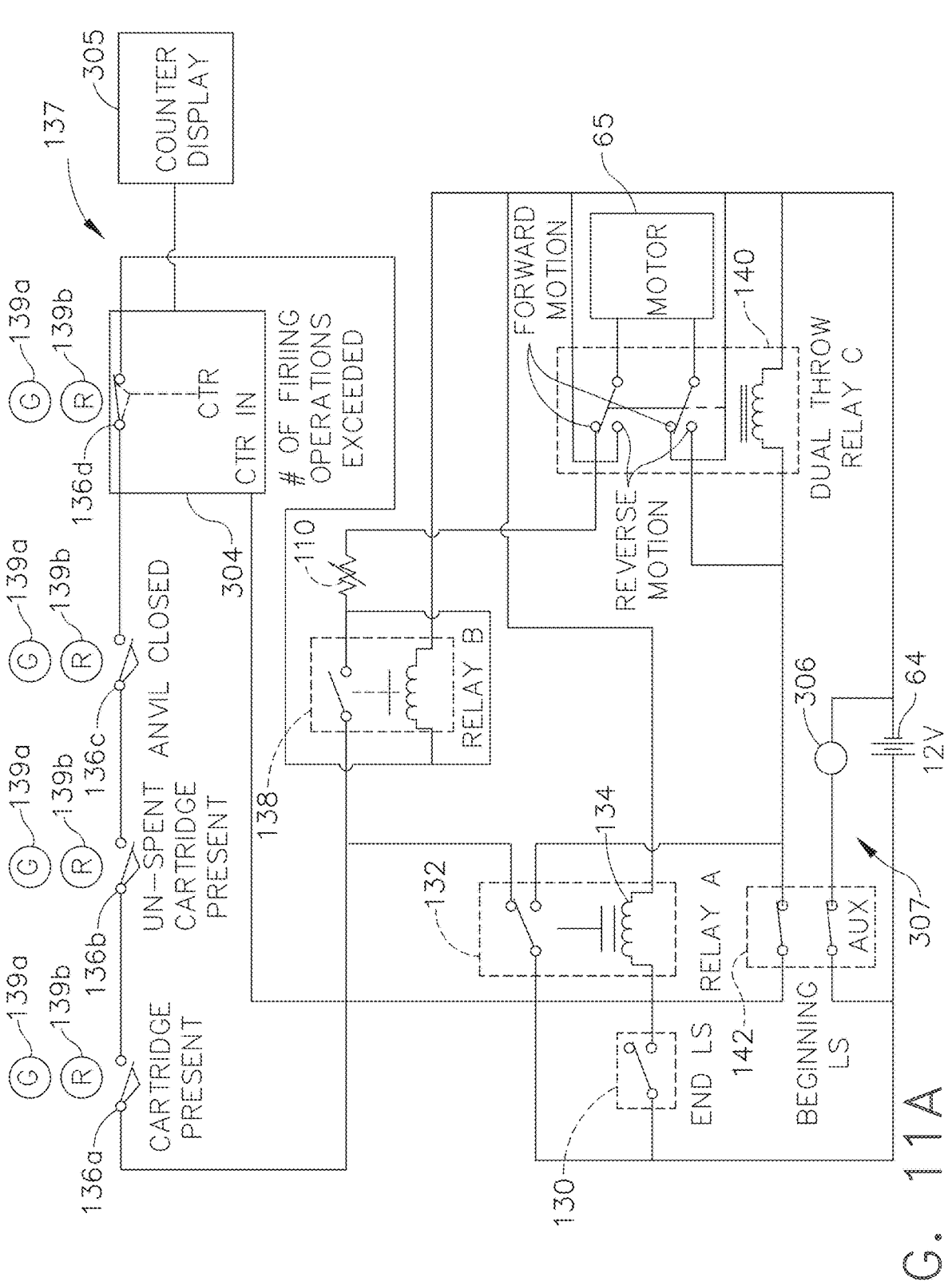
FIG. 11A is a schematic diagram of another circuit that may be used in the instrument according to various embodiments of the present invention.

FIG. 11A is a schematic diagram of another electrical circuit of the instrument 10 according to various embodiments of the present invention. This electrical circuit includes lockout sensor switches 136a-d collectively defining an interlock circuit 137 through which current from the relay 132, when de-energized, must pass in order for electrical operation of the motor 65 to be initiated. Each lockout sensor switch 136a-d is configured to maintain an open (i.e., non-conductive) switch state or a closed (i.e., conductive) switch state responsive to the presence or absence, respectively, of a corresponding condition. Any of the corresponding conditions, if present when the instrument 10 is fired, may result in an unsatisfactory cutting and stapling operation and/or damage to the instrument 10. Conditions to which the lockout sensor switches 136a-d may respond include, for example, the absence of the staple cartridge 34 in the channel 22, the presence of a spent (e.g., previously fired) staple cartridge 34 in the channel 22, and an open (or otherwise insufficiently closed) position of the anvil 24 with respect to the channel 22. Other conditions to which the lockout sensor switches 136a-d may respond, such as component wear, may be inferred based upon an accumulated number of firing operations produced by the instrument 10. Accordingly, if any of these conditions exists, the corresponding lockout sensor switches 136a-d maintain an open switch state, thus preventing passage of the current necessary to initiate operation of the motor 65. Passage of current by the lockout sensors 136a-d is allowed only after all of the conditions have been remedied. It will be appreciated that the above-described conditions are provided by way of example only, and that additional lockout sensor switches for responding to other conditions detrimental to operation of the instrument 10 may be provided. It will similarly be appreciated that for embodiments in which one or more of the above-described conditions may not exist or are of no concern, the number of lockout sensor switches may be fewer than that depicted.

As shown in FIG. 11A, the lockout sensor switch 136a may be implemented using a normally-open switch configuration such that a closed switch state is maintained when the staple cartridge 34 is in a position corresponding to its proper receipt by the channel 22. When the staple cartridge 34 is not installed in the channel 22, or is installed improperly (e.g., mis-aligned), the lockout sensor switch 136a maintains an open switch state.

Lockout sensor switch 136b may be implemented using a normally-open switch configuration such that a closed switch state is maintained only when an unspent staple cartridge 34 (i.e., a staple cartridge 34 having a sled 33 in the unfired position) is present in the channel 22. The presence of a spent staple cartridge 34 in the channel 22 causes the lockout sensor switch 136b to maintain an open switch state.

Lockout sensor switch 136c may be implemented using a normally-open switch configuration such that a closed switch state is maintained when the anvil 24 is in a closed position with respect to the channel 22. As discussed in further detail below, the lockout sensor switch 136c may be controlled in accordance with a time delay feature wherein a closed switch state is maintained only after the anvil 24 is in the closed position for a pre-determined period of time.

Lockout sensor switch 136d may be implemented using a normally-closed switch configuration such that a closed switch state is maintained only when an accumulated number of firings produced by the instrument 10 is less than a pre-determined number. As discussed in further detail below, the lockout sensor switch 136d may be in communication with a counter 304 configured for maintaining a count representative of the accumulated number of firing operations performed by the instrument, comparing the count to the pre-determined number, and controlling the switch state of the lockout sensor switch 136d based upon the comparison.

According to various embodiments, the interlock circuit 137 may comprise one or more indicators visible to the user of the instrument 10 for displaying a status of at least one of the lockout sensor switches 136a-c. As shown in FIG. 11A, for example, each lockout sensor switch 136a-d may have a green LED 139a and a red LED 139b associated therewith. The interlock circuit 137 may be configured such that the LEDs 139a,b are energized when the corresponding lockout sensor switch 136a-d is maintained in the closed and open switch states, respectively. It will be appreciated that the lockout sensor switches 136a-d may comprise one or more auxiliary switch contacts (not shown) having a switch configuration suitable for operating the LEDs 139a,b in the manner described above.

Figures 50A, 50B:
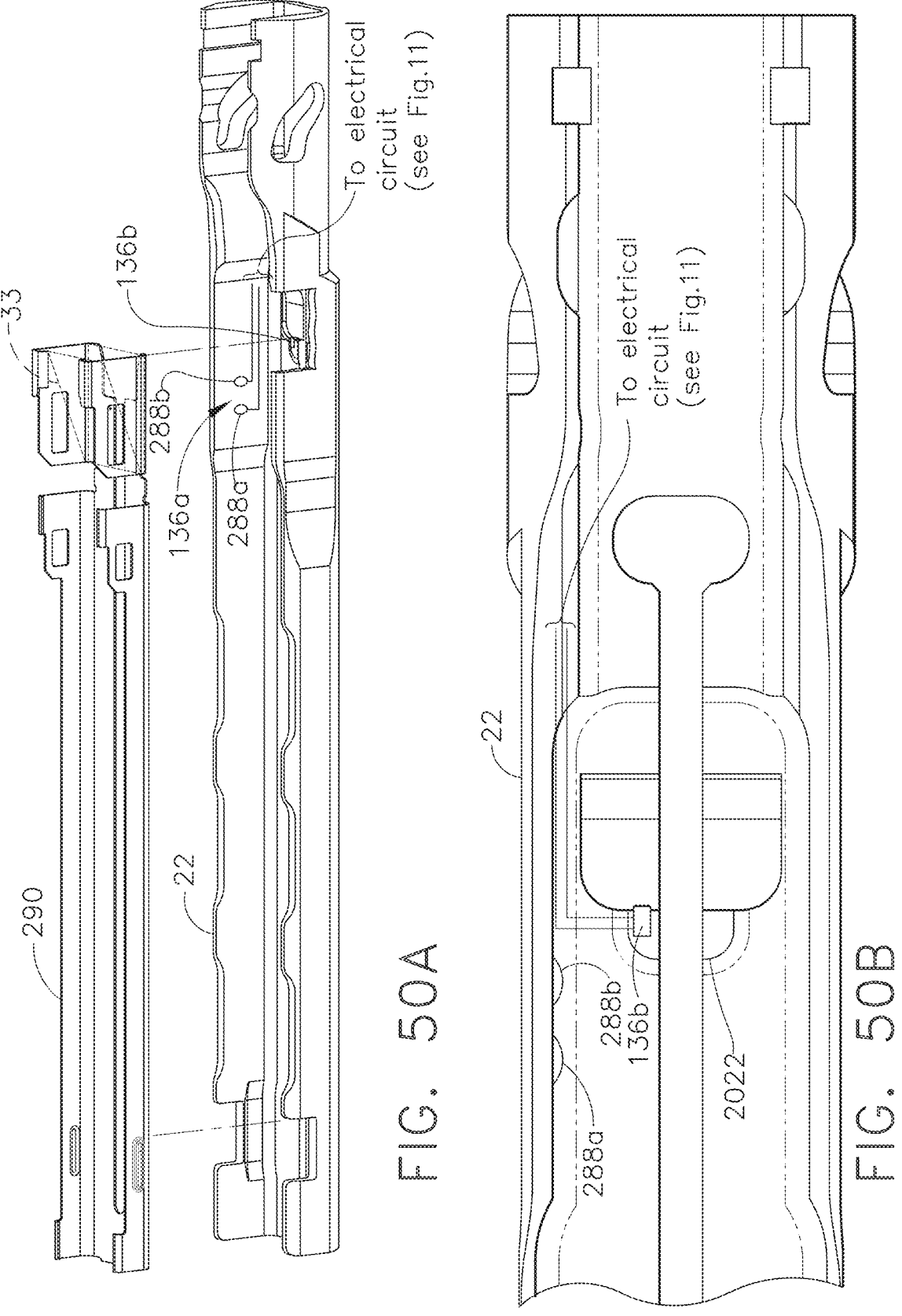
FIG. 50A illustrates an exploded view of the staple channel and portions of a staple cartridge of the instrument showing various sensors according to various embodiments of the present invention.
FIG. 50B illustrates a top down view of the staple channel of the instrument showing various sensors according to various embodiments of the present invention.

FIGS. 50A-51C illustrate mounting arrangements and configurations of the lockout sensor switches 136a-d of the interlock circuit 137 according to various embodiments of the present invention. As shown in FIG. 50A, the lockout sensor switch 136a may comprise a first switch contact 288a and a second switch contact 288b disposed upon an inner wall of the channel 22 and electrically isolated therefrom. The respective positions of the first and second switch contacts 288a,b are such that when the staple cartridge 34 is in a position corresponding to its proper receipt by the channel 22, a conductive or semi-conductive portion 290 of the staple cartridge 34 (exemplified as a metal tray portion of the staple cartridge 34) contacts the first and second switch contacts 288a,b to establish a conductive path therebetween.

As best seen in FIG. 50B, each switch contact 288a,b may comprise a rounded profile for minimizing mechanical resistance to the staple cartridge 34 when received by the channel 22 and for enabling affirmative electrical contact with the conductive portion 290 thereof. The conductive portion 290 thus operates to maintain the lockout sensor switch 136a in a closed switch state. Although the switch contacts 288a,b are shown adjacently positioned on a sidewall portion of the channel 22, it will be appreciated that each switch contact 288a,b may generally be located at any location within the channel 22 where suitable electrical contact with the conductive member 290 is possible. It will further be appreciated that the lockout sensor switch 136a may alternatively be implemented using a conventional contact-actuated limit switch. According to such embodiments, the limit switch may be positioned such that staple cartridge 34, when received by the channel 22, mechanically actuates the limit switch such that a closed switch state is maintained. It will further be appreciated that the lockout sensor switch 136a may also be implemented using a conventional non-contact actuated limit switch, such as, for example, a magnetic reed limit switch or a Hall effect proximity switch. According to such embodiments, the staple cartridge 34 may comprise a magnet suitable for causing the lockout sensor switch 136a to maintain a closed switch state when the staple cartridge 34 is installed.

As best seen in FIG. 50B, the lockout sensor switch 136b may be mounted on an interior bottom surface of the channel 22. According to various embodiments and as shown, the lockout sensor switch 136b may be implemented using a contact-actuated limit switch of a conventional design that is suitable for detecting linear movement. Orientation of the lockout sensor switch 136b may be such that an actuated portion thereof extends upwardly from the bottom interior surface of the channel 22. The position of the lockout sensor switch 136b on the bottom surface of the channel 22 is such that when an unspent staple cartridge 34 is installed, a bottom portion of the sled 33 mechanically actuates the lockout sensor switch 136b and causes a closed switch state to be maintained thereby. Accordingly, the presence of an unspent staple cartridge 34 (i.e., a staple cartridge having a sled 33 in the unfired position) enables the passage of current through the lockout sensor switch 136b. It will be appreciated the lockout sensor switch 136b may instead be implemented using a non-contact actuated switch (e.g., a magnetic reed limit switch or a Hall effect proximity switch). For such implementations, the sled 33 may comprise a magnetized portion, for example, that actuates the lockout sensor switch 136b when the sled 33 is present in the un-fired position.

As shown in FIG. 51A, the lockout sensor switch 136c is positioned adjacent a distal end of one of the pivot recesses 296 defined by the proximal end of the channel 22 for engaging a corresponding pivot point 25 of the anvil 24. According to various embodiments and as shown, the lockout sensor switch 136c may be implemented using a contact-actuated limit switch of a conventional design that is suitable for detecting linear movement. It will be appreciated, however, that a non-contact-actuated limit switch may be used instead. Orientation of the lockout sensor switch 136c may be such that an actuated portion thereof extends slightly over the distal end of the corresponding pivot recess 296. When the anvil 24 is in an open position with respect to the channel 22 (as shown in FIG. 51A), the pivot point 25 is positioned at the proximal end of the pivot recess 296. Closure of the anvil 24 causes the pivot point 25 to move to the distal end of the pivot recess 296. The resulting contact of the pivot point 25 with the actuated portion of the lockout sensor switch 136c causes the lockout sensor switch 136c to maintain a closed switch state, thus enabling the passage of current therethrough.

According to other embodiments and as shown in FIG. 51B, the lockout sensor switch 136c may instead be configured to maintain a closed switch state responsive to an electrical signal. The electrical signal may be, for example, an analog signal generated by a force sensor 298 disposed on a bottom inner surface of the channel 22 that represents a magnitude of the clamping force applied by the anvil 24. The closed position of the anvil 24 may thus be inferred if the analog signal is sufficiently large in magnitude. Accordingly, the analog signal may be received by a comparator circuit 141 configured to determine if the magnitude exceeds a pre-determined threshold stored therein. If the threshold is exceeded, indicating closure of the anvil 24, the comparator circuit 141 causes the lockout sensor switch 136c to maintain a closed switch state, thus enabling the passage of current therethrough. If the magnitude of the analog signal is less than the pre-determined threshold, indicating that the anvil 24 is not sufficiently closed, the comparator circuit 141 causes the lockout sensor switch 136c to maintain an open switch state, thus preventing the passage of current therethrough. Although shown separately, it will be appreciated that the comparator circuit 141 may be integral with the lockout sensor switch 136c so as to form a common device. It will further be appreciated that the pre-defined threshold stored by the comparator circuit 141 may be adjusted as necessary to reflect the force indicative of closure of the anvil 24 for different cutting and stapling operations.

In certain instances, it may be necessary or otherwise desirable to delay commencement of a firing operation for a period of time subsequent to closure of the anvil 24. For example, the introduction of a delay between the clamping and firing operations may serve to improve the stabilization of clamped tissue. Accordingly, with reference to FIG. 51C, embodiments of the present invention may comprise a timer 300 having a pre-set time delay (e.g., 12 seconds) and configured for controlling the switch state of the lockout sensor switch 136c in accordance with a time-based position of the anvil 24. Although shown separately, it will be appreciated that the timer 300 may be integral with the lockout sensor switch 136c so as to form a common device (e.g., an on-delay timer). Preferably, the timer 300 is implemented as an electronic device, although it will be appreciated that a mechanical timer may be used instead. A normally-open limit switch 302 configured in a manner identical to that of FIG. 51A may be connected to the timer 300 such that timing is initiated when the anvil 24 is in a closed position with respect to the channel 22. Upon expiration of the pre-set time delay, the timer 300 causes the lockout sensor switch 136c to maintain a closed switch state, thus enabling the passage of current therethrough. The timer 300 may be reset in response to the transition of the limit switch 302 to an open switch state (i.e., when the anvil 24 is in the open position). It will be appreciated that the pre-set time delay of the timer 300 may be selectively adjusted (e.g., using an integral potentiometer adjustment) as required.

Referring again to FIG. 11A, the electrical circuit may comprise a counter 304 configured to maintain a count representative of the accumulated number of firing operations performed by the instrument 10 and, based on the count, to control the switch state of the lockout sensor switch 136d. Although shown separately, it will be appreciated that counter 304 may be integral with the lockout sensor switch 136d so as to form a common device. Preferably, the counter 304 is implemented as an electronic device having an input for incrementing the maintained count based upon the transition of a discrete electrical signal provided thereto. It will be appreciated that a mechanical counter configured for maintaining the count based upon a mechanical input (e.g., retraction of the firing trigger 20) may be used instead. When implemented as an electronic device, any discrete signal present in the electrical circuit that transitions once for each firing operation may be utilized for the counter 304 input. As shown in FIG. 11A, for example, the discrete electrical signal resulting from actuation of the end-of-stroke sensor 130 may be utilized. The counter 304 may control the switch state of lockout sensor switch 136d such that a closed switch state is maintained when the maintained count is less than a pre-determined number stored within the counter 304. When the maintained count is equal to the pre-determined number, the counter 304 causes the lockout sensor switch 136d to maintain an open switch state, thus preventing the passage of current therethrough. It will be appreciated that the pre-determined number stored by the counter 304 may be selectively adjusted as required. According to various embodiments, the counter 304 may be in communication with a display 305, such as an LCD display, integral to the instrument 10 for indicating to a user either the maintained count or the difference between the pre-determined number and the maintained count.

When the lockout sensor switches 136a-d collectively maintain a closed switch state, a single pole, single throw relay 138 is energized. When the relay 138 is energized, current flows through the relay 138, through the variable resistor sensor 110, and to the motor 65 via a double pole, double throw relay 140, thereby powering the motor 65 and allowing it to rotate in the forward direction. Because the output of the relay 138, once energized, maintains the relay 138 in an energized state until relay 132 is energized, the interlock circuit 137 will not function to prevent operation of the motor 165 once initiated, even if one or more of the interlock sensor switches 136a-d subsequently maintains an open switch state. In other embodiments, however, it may be necessary or otherwise desirable to connect the interlock circuit 137 and the relay 138 such that one or more the lockout sensor switches 136a-d must maintain a closed switch state in order to sustain operation of the motor 165 once initiated.

Rotation of the motor in the forward direction causes the ring 84 to move distally and thereby de-actuate the stop motor sensor switch 142. Because the switch 142 is normally-closed, solenoid 306 is energized. The solenoid 306 may be a conventional push-type solenoid that, when energized, causes a plunger (not shown) to be axially extended. As discussed below in connection with FIGS. 14-22, extension of the plunger may operate to retain the closure trigger 18 in the retracted position, thus preventing the anvil 24 from opening while a firing operation is in progress (i.e., while the switch 142 is not actuated). Upon de-energization of the solenoid 306, the plunger is retracted such that manual release of the closure trigger 18 is possible.

When the end effector 12 reaches the end of its stroke, the reverse motor sensor 130 will be activated, thereby closing the switch 130 and energizing the relay 132. This causes the relay 132 to assume its energized state, which causes current to bypass the interlock circuit 137 and variable resistor 110, and instead causes current to flow to both the normally-closed double pole, double throw relay 140 and back to the motor 65, but in a manner, via the relay 140, that causes the motor 65 to reverse its rotational direction.

Because the stop motor sensor switch 142 is normally-closed, current will flow back to the relay 132 to keep it energized until the switch 142 opens. When the knife 32 is fully retracted, the stop motor sensor switch 142 is activated, causing the switch 142 to open, thereby removing power from the motor 65 and de-energizing the solenoid 306.

In other embodiments, rather than a proportional-type sensor 110, an on-off type sensor could be used. In such embodiments, the rate of rotation of the motor 65 would not be proportional to the force applied by the operator. Rather, the motor 65 would generally rotate at a constant rate. But the operator would still experience force feedback because the firing trigger 20 is geared into the gear drive train.

Figure 12:
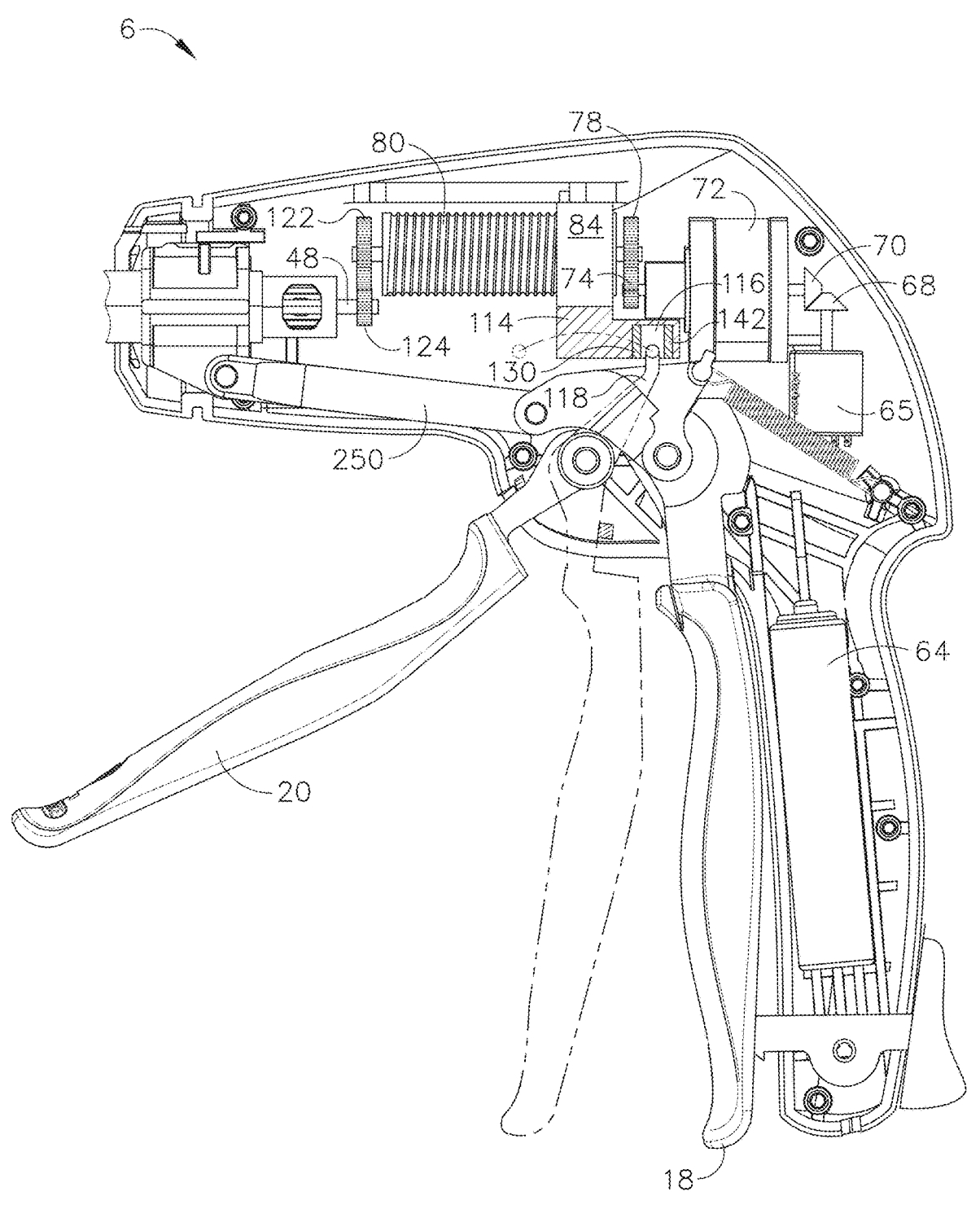
FIGS. 12-13 are side views of the handle according to other embodiments of the present invention.

FIG. 12 is a side-view of the handle 6 of a power-assist motorized endocutter according to another embodiment. The embodiment of FIG. 12 is similar to that of FIGS. 7-10 except that in the embodiment of FIG. 12, there is no slotted arm connected to the ring 84 threaded on the helical gear drum 80. Instead, in the embodiment of FIG. 12, the ring 84 includes a sensor portion 114 that moves with the ring 84 as the ring 84 advances down (and back) on the helical gear drum 80. The sensor portion 114 includes a notch 116. The reverse motor sensor 130 may be located at the distal end of the notch 116 and the stop motor sensor 142 may be located at the proximate end of the notch 116. As the ring 84 moves down the helical gear drum 80 (and back), the sensor portion 114 moves with it. Further, as shown in FIG. 12, the middle piece 104 may have an arm 118 that extends into the notch 12.

In operation, as an operator of the instrument 10 retracts in the firing trigger 20 toward the pistol grip 26, the run motor sensor 110 detects the motion and sends a signal to power the motor 65, which causes, among other things, the helical gear drum 80 to rotate. As the helical gear drum 80 rotates, the ring 84 threaded on the helical gear drum 80 advances (or retracts, depending on the rotation). Also, due to the pulling in of the firing trigger 20, the middle piece 104 is caused to rotate counter clockwise with the firing trigger 20 due to the forward motion stop 107 that engages the firing trigger 20. The counter clockwise rotation of the middle piece 104 cause the arm 118 to rotate counter clockwise with the sensor portion 114 of the ring 84 such that the arm 118 stays disposed in the notch 116. When the ring 84 reaches the distal end of the helical gear drum 80, the arm 118 will contact and thereby trip the reverse motor sensor 130. Similarly, when the ring 84 reaches the proximate end of the helical gear drum 80, the arm will contact and thereby trip the stop motor sensor 142. Such actions may reverse and stop the motor 65, respectively as described above.

Figure 13:
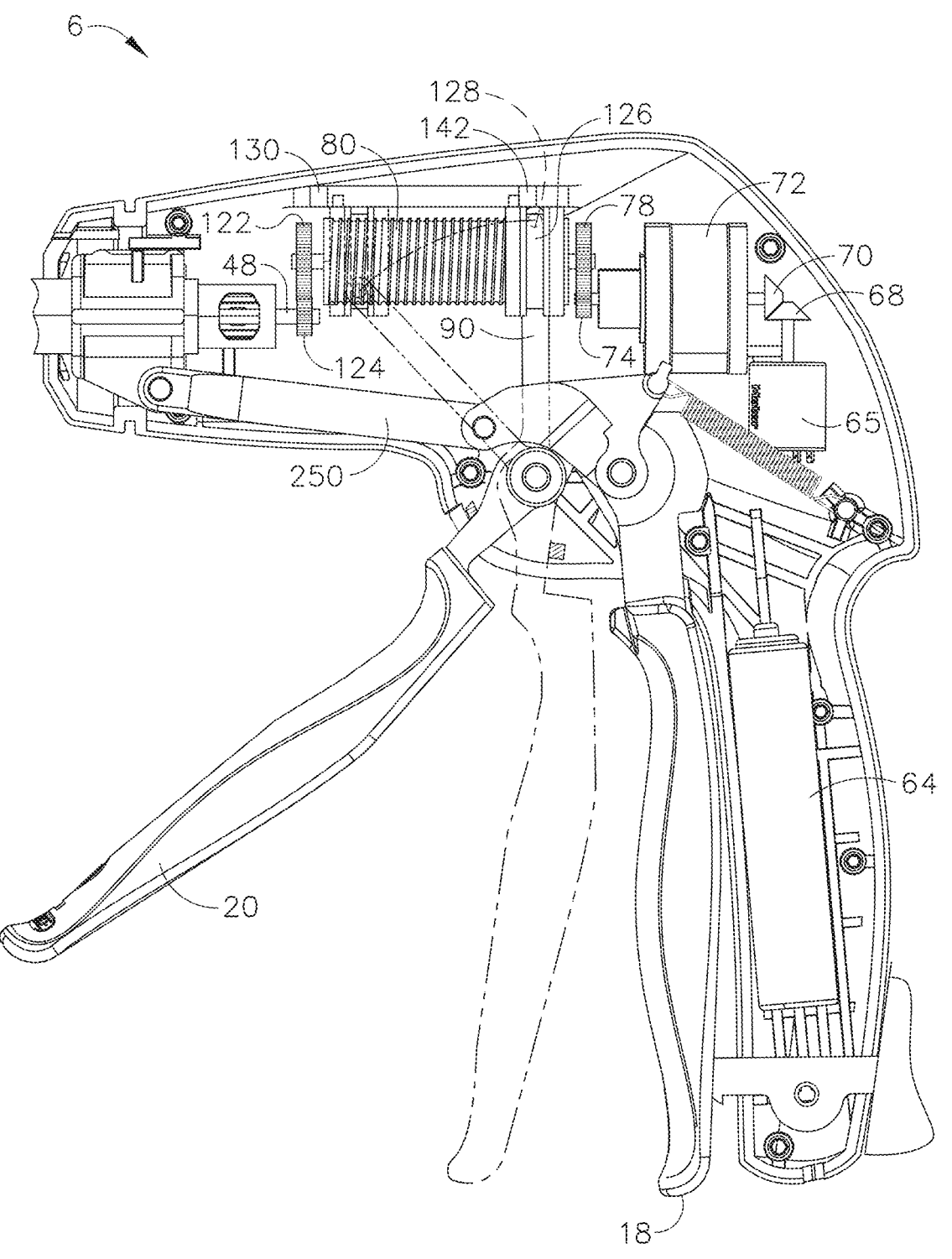

FIG. 13 is a side-view of the handle 6 of a power-assist motorized endocutter according to another embodiment. The embodiment of FIG. 13 is similar to that of FIGS. 7-10 except that in the embodiment of FIG. 13, there is no slot in the arm 90. Instead, the ring 84 threaded on the helical gear drum 80 includes a vertical channel 126. Instead of a slot, the arm 90 includes a post 128 that is disposed in the channel 126. As the helical gear drum 80 rotates, the ring 84 threaded on the helical gear drum 80 advances (or retracts, depending on the rotation). The arm 90 rotates counter clockwise as the ring 84 advances due to the post 128 being disposed in the channel 126, as shown in FIG. 13.

Figure 14:
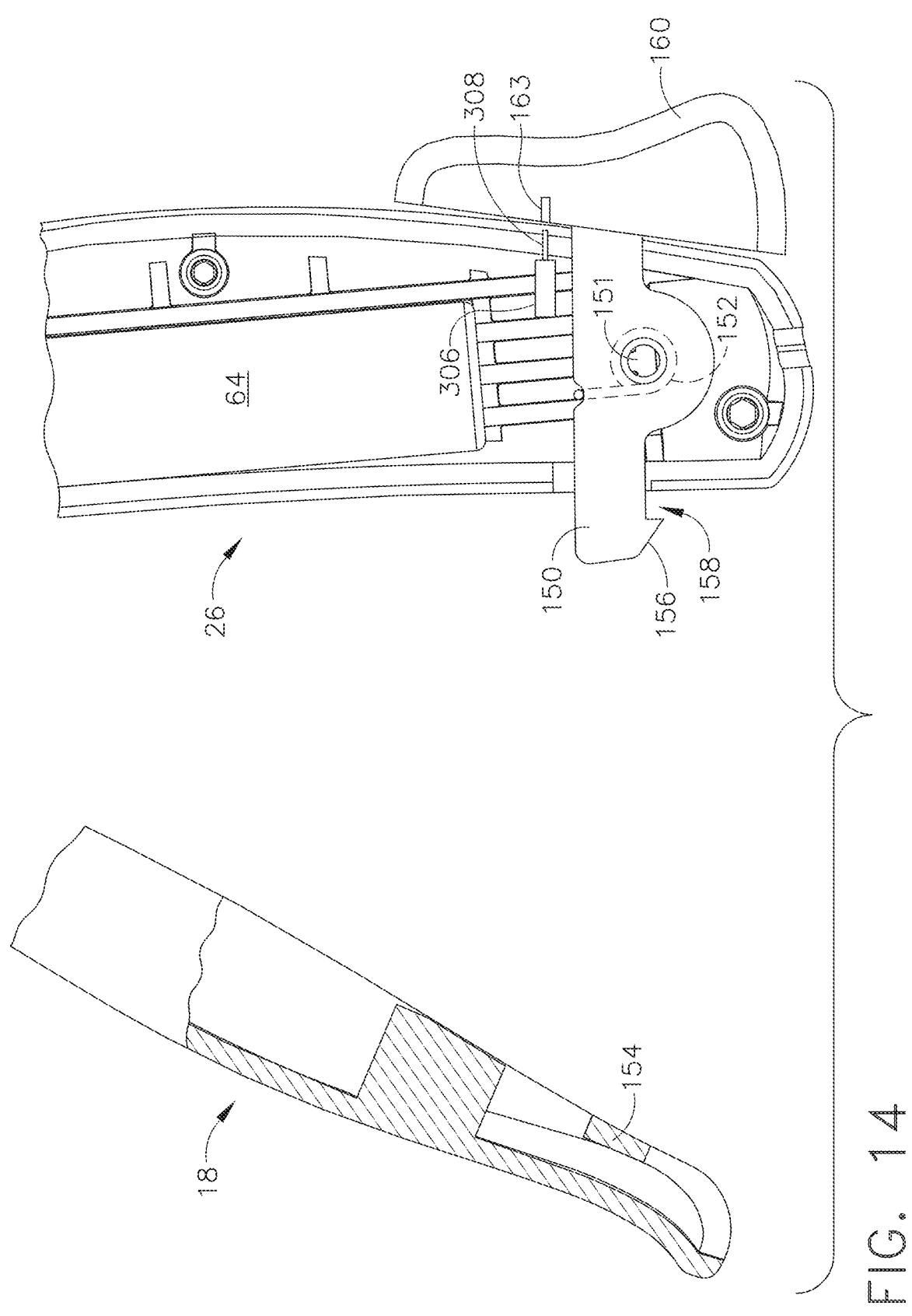
FIGS. 14-22 illustrate different mechanisms for locking the closure trigger according to various embodiments of the present invention.
Figure 15:
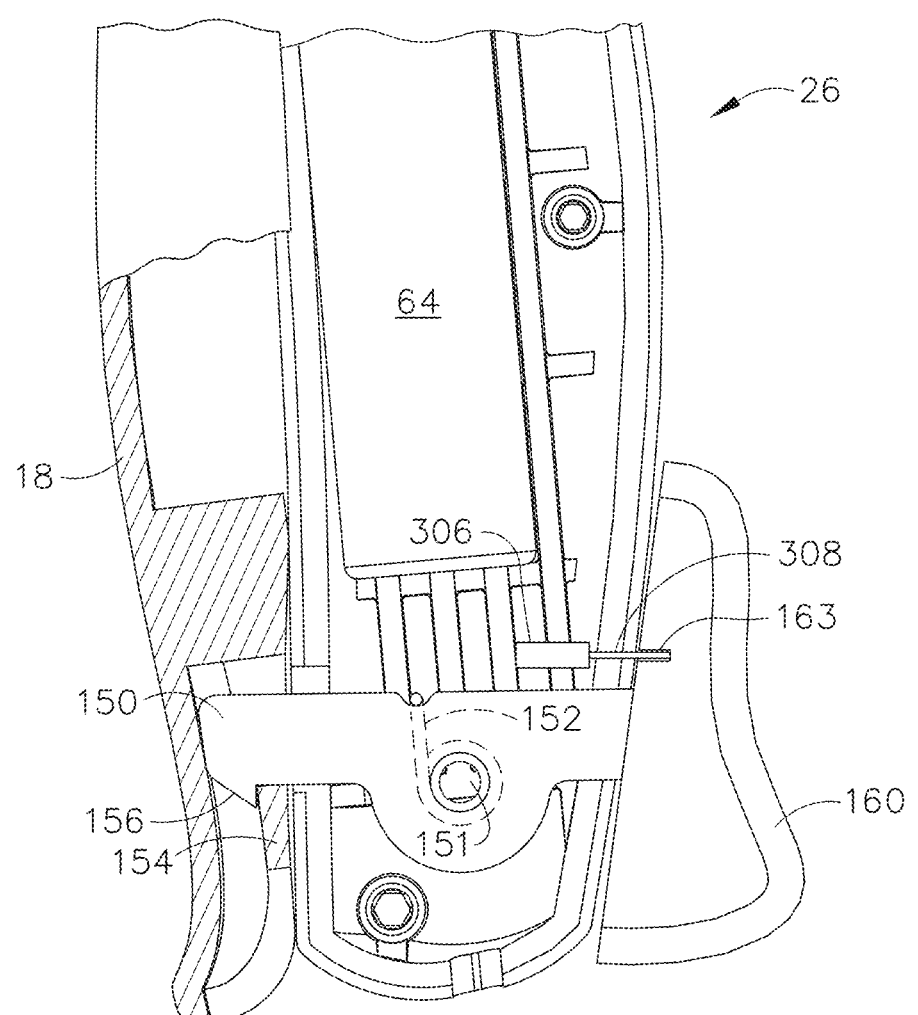

As mentioned above, in using a two-stroke motorized instrument, the operator first pulls back and locks the closure trigger 18. FIGS. 14 and 15 show one embodiment of a way to lock the closure trigger 18 to the pistol grip portion 26 of the handle 6. In the illustrated embodiment, the pistol grip portion 26 includes a hook 150 that is biased to rotate CCW about a pivot point 151 by a torsion spring 152. Also, the closure trigger 18 includes a closure bar 154. As the operator draws in the closure trigger 18, the closure bar 154 engages a sloped portion 156 of the hook 150, thereby rotating the hook 150 upward (or CW in FIGS. 14-15) until the closure bar 154 completely passes the sloped portion 156 into a recessed notch 158 of the hook 150, which locks the closure trigger 18 in place. The operator may release the closure trigger 18 by pushing down on a slide button release 160 on the back or opposite side of the pistol grip portion 26. Pushing down the slide button release 160 rotates the hook 150 CW such that the closure bar 154 is released from the recessed notch 158. In order to prevent the anvil 24 from inadvertently being opened while a firing operation is in progress, the solenoid 306 may be positioned within the pistol grip 26 such that the plunger 308 of the solenoid 306, when energized, is received into a corresponding opening 163 of the slide button release 160. Accordingly, the slide button release 160 is locked in place such that manipulation of the slide button release 160 is prevented until the plunger 308 is retracted from the opening 163 at the conclusion of the firing operation.

Figure 16:
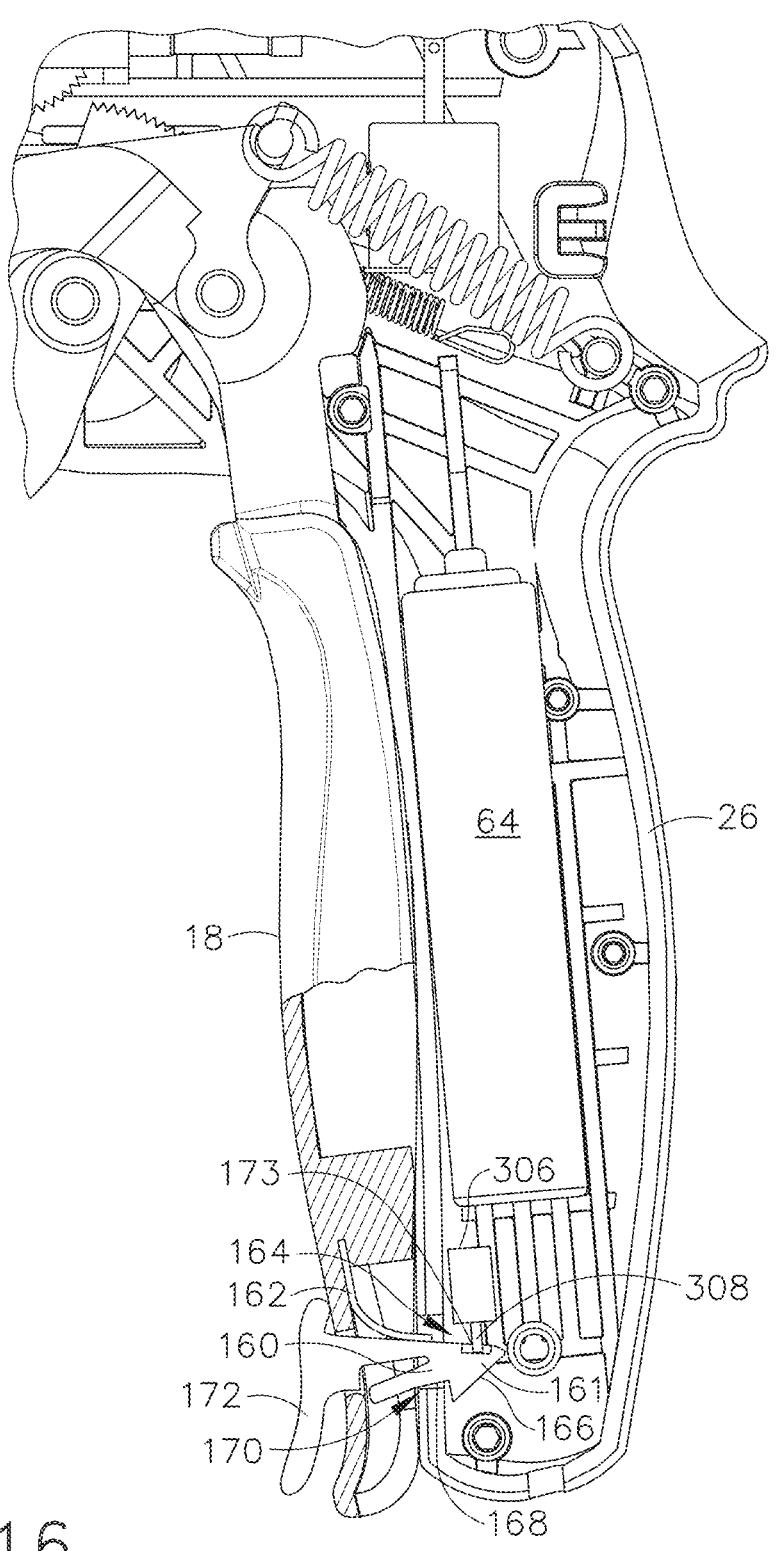

FIG. 16 shows another closure trigger locking mechanism according to various embodiments. In the embodiment of FIG. 16, the closure trigger 18 includes a wedge 160 having an arrow-head portion 161. The arrow-head portion 161 is biased downward (or clockwise) by a leaf spring 162. The wedge 160 and leaf spring 162 may be made from, for example, molded plastic. When the closure trigger 18 is retracted, the arrow-head portion 161 is inserted through an opening 164 in the pistol grip portion 26 of the handle 6. A lower chamfered surface 166 of the arrow-head portion 161 engages a lower sidewall 168 of the opening 164, forcing the arrow-head portion 161 to rotate counter clockwise. Eventually the lower chamfered surface 166 fully passes the lower sidewall 168, removing the counter clockwise force on the arrow-head portion 161, causing the lower sidewall 168 to slip into a locked position in a notch 170 behind the arrow-head portion 161.

To unlock the closure trigger 18, a user presses down on a button 172 on the opposite side of the closure trigger 18, causing the arrow-head portion 161 to rotate CCW and allowing the arrow-head portion 161 to slide out of the opening 164. In order to prevent the anvil 24 from inadvertently being opened while a firing operation is in progress, the solenoid 306 may be positioned within the pistol grip 26 such that the plunger 308 of the solenoid 306, when energized, is received into a corresponding opening 173 defined by the arrow-head portion 161. When received into the opening 173, the plunger 308 operates to prevent CCW rotation of the arrow-head portion 161. Accordingly, inadvertent manipulation of the button 172 by the user is prevented by the user until the plunger 308 is retracted from the opening 173 at the conclusion of the firing operation.

Figure 17:
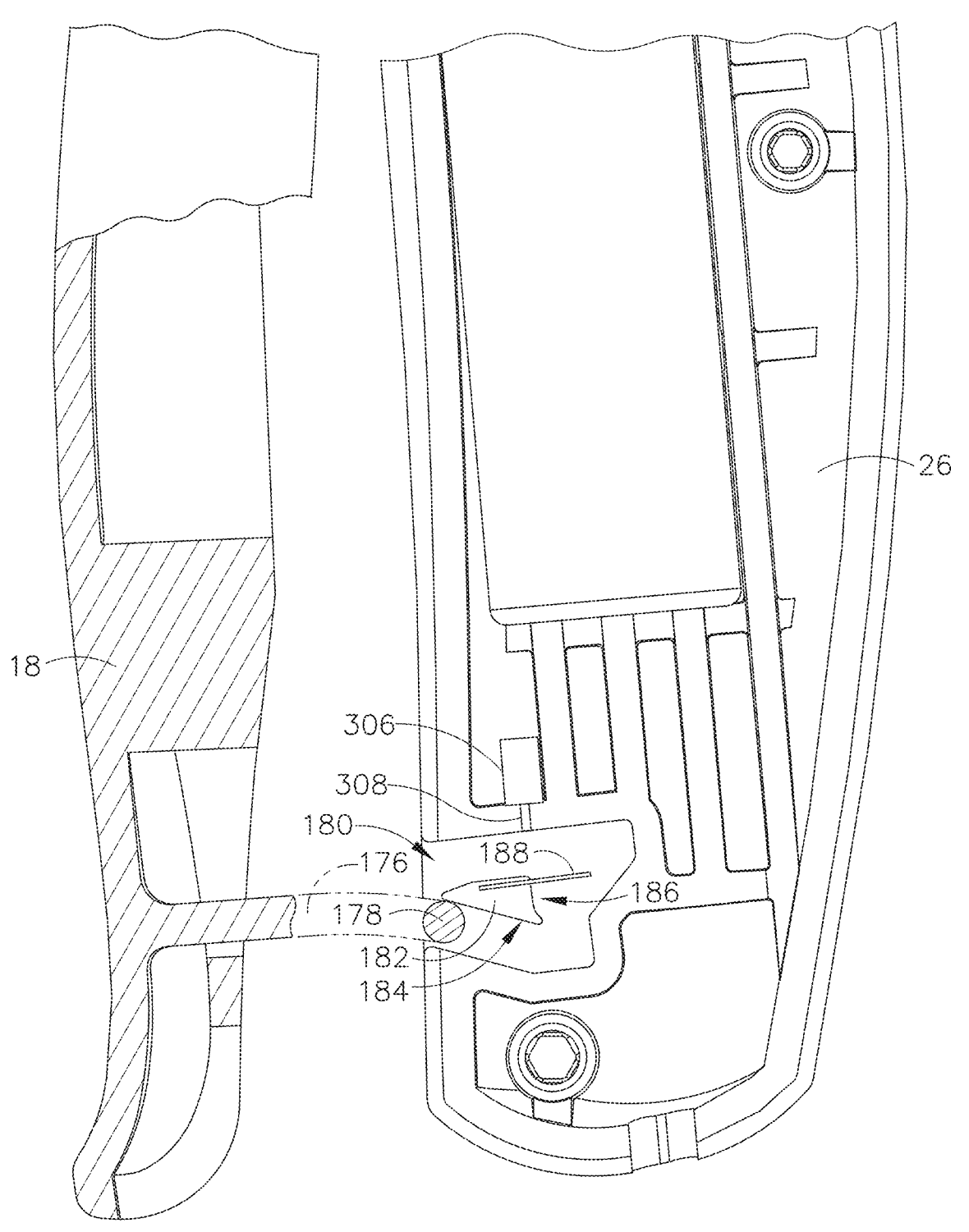
Figure 18:
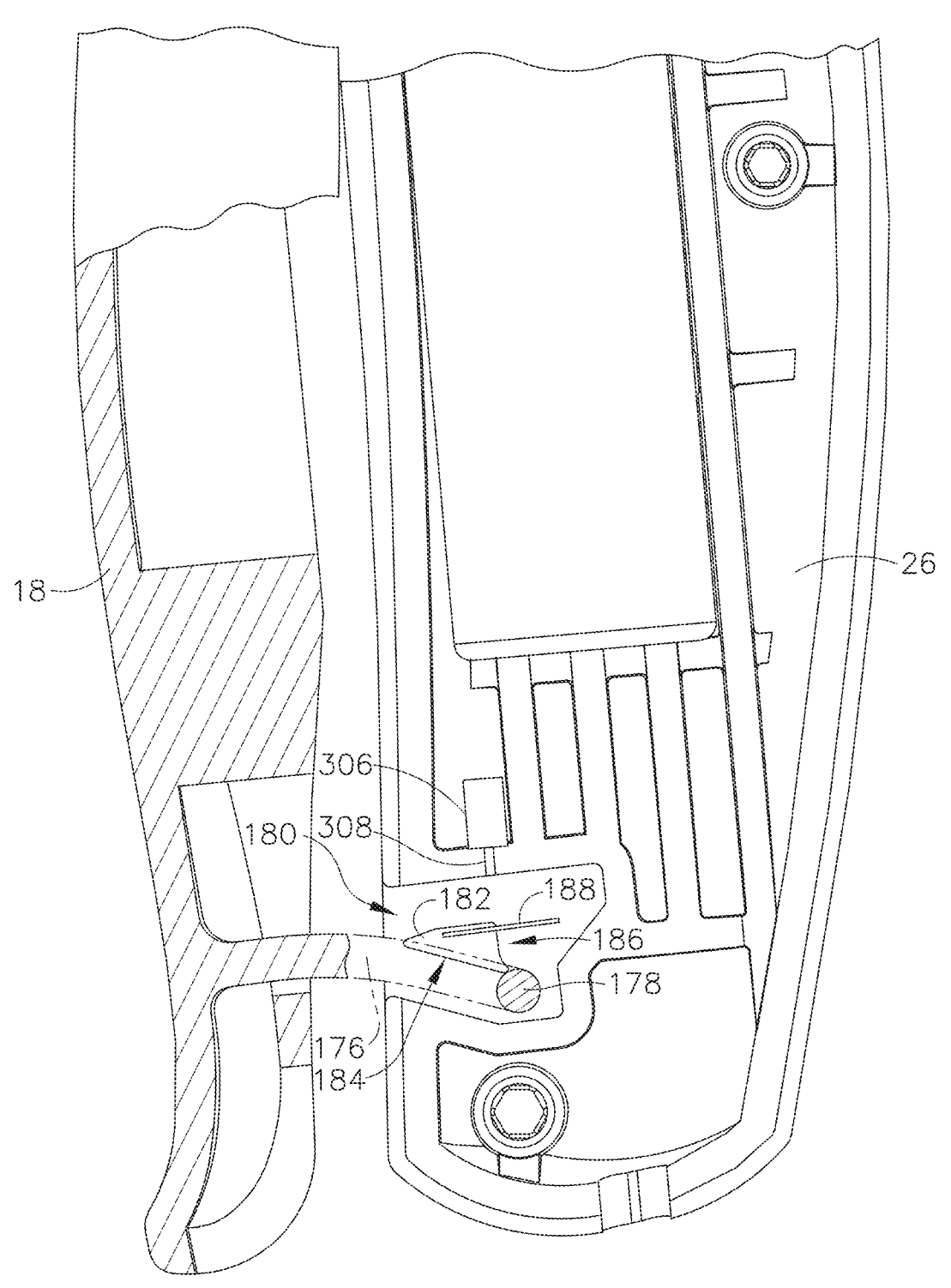
Figure 19:
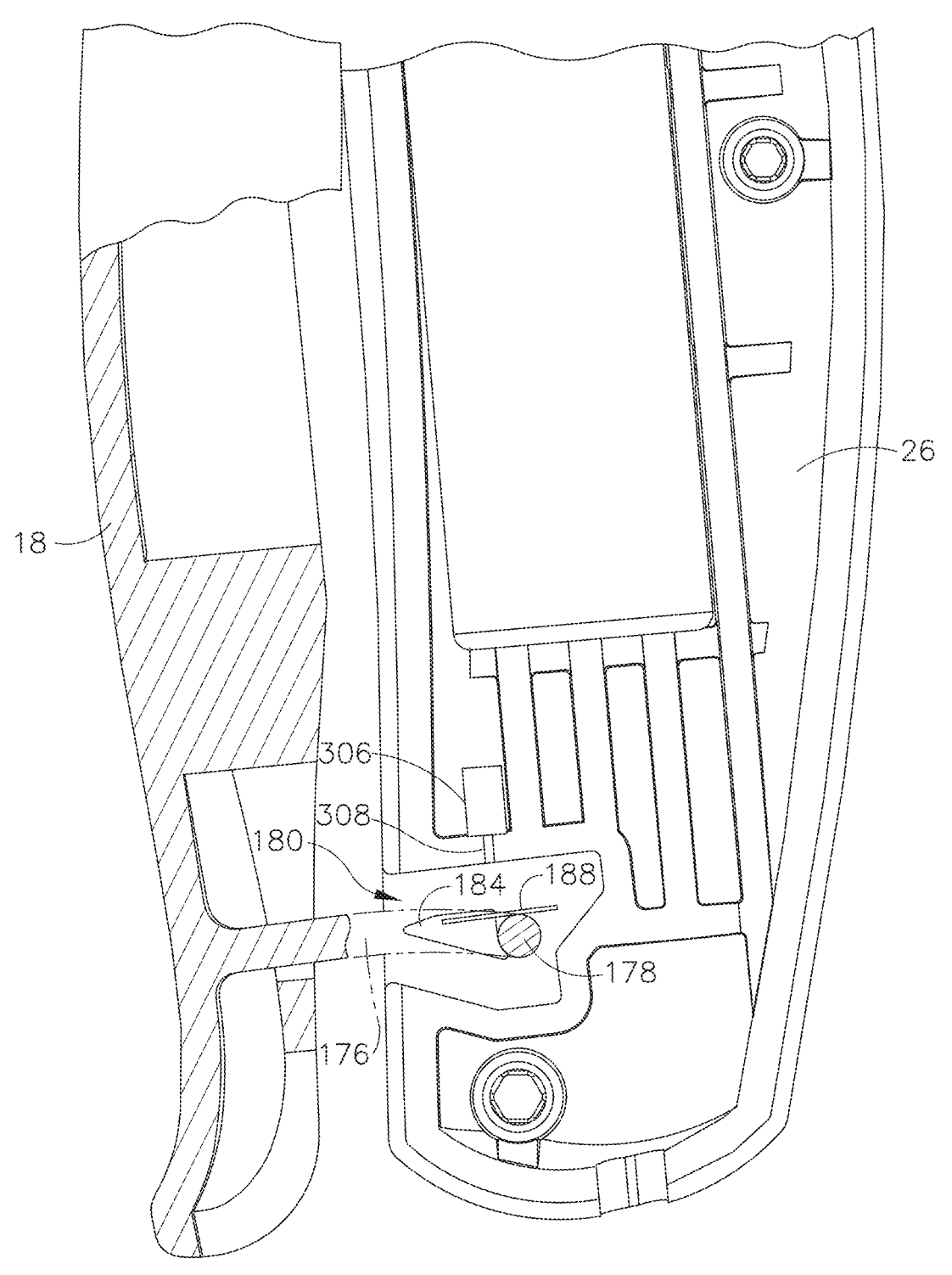

FIGS. 17-22 show a closure trigger locking mechanism according to another embodiment. As shown in this embodiment, the closure trigger 18 includes a flexible longitudinal arm 176 that includes a lateral pin 178 extending therefrom. The arm 176 and pin 178 may be made from molded plastic, for example. The pistol grip portion 26 of the handle 6 includes an opening 180 with a laterally extending wedge 182 disposed therein. When the closure trigger 18 is retracted, the pin 178 engages the wedge 182, and the pin 178 is forced downward (i.e., the arm 176 is rotated clockwise) by the lower surface 184 of the wedge 182, as shown in FIGS. 17 and 18. When the pin 178 fully passes the lower surface 184, the clockwise force on the arm 176 is removed, and the pin 178 is rotated counter clockwise such that the pin 178 comes to rest in a notch 186 behind the wedge 182, as shown in FIG. 19, thereby locking the closure trigger 18. The pin 178 is further held in place in the locked position by a flexible stop 188 extending from the wedge 184.

Figure 20:
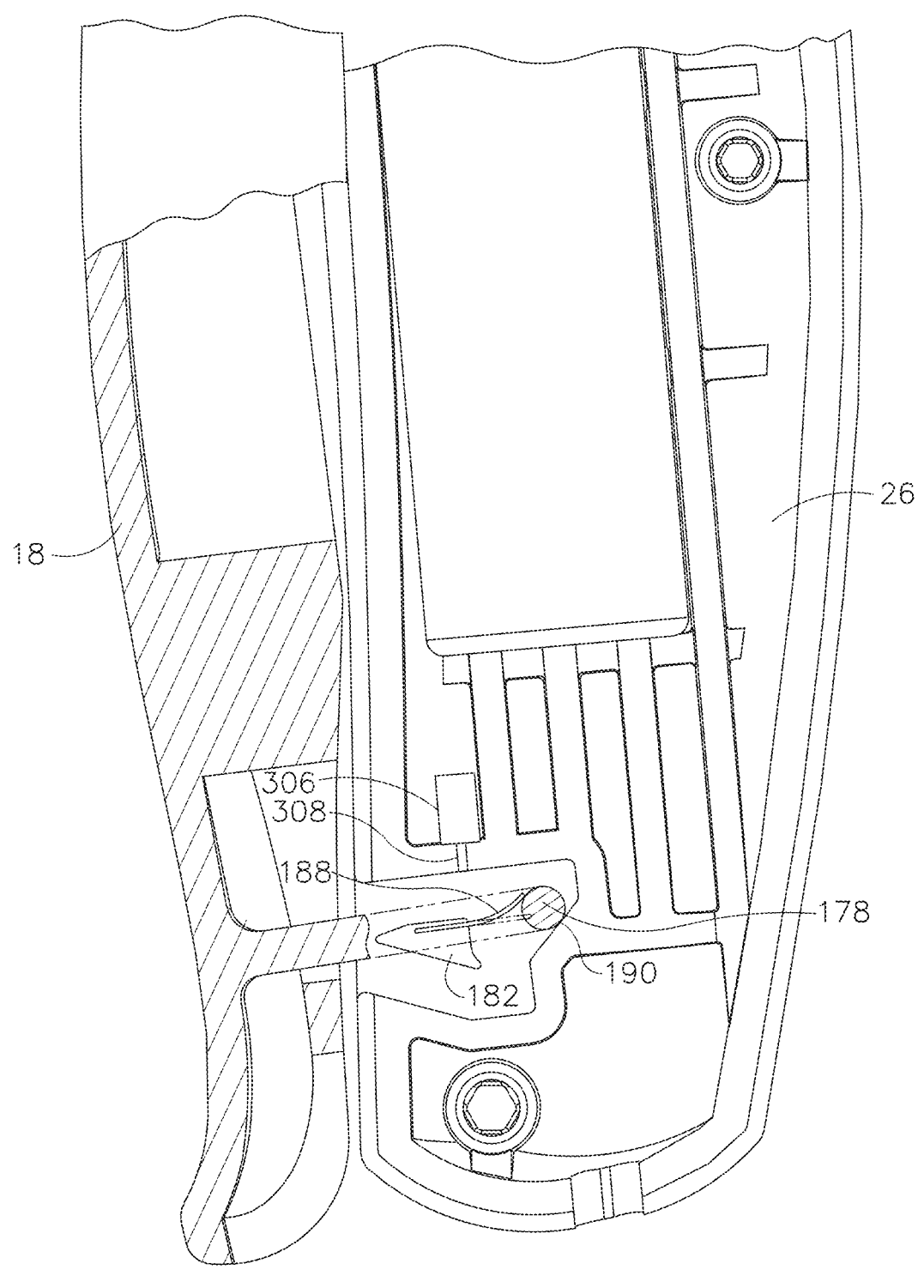
Figure 21:
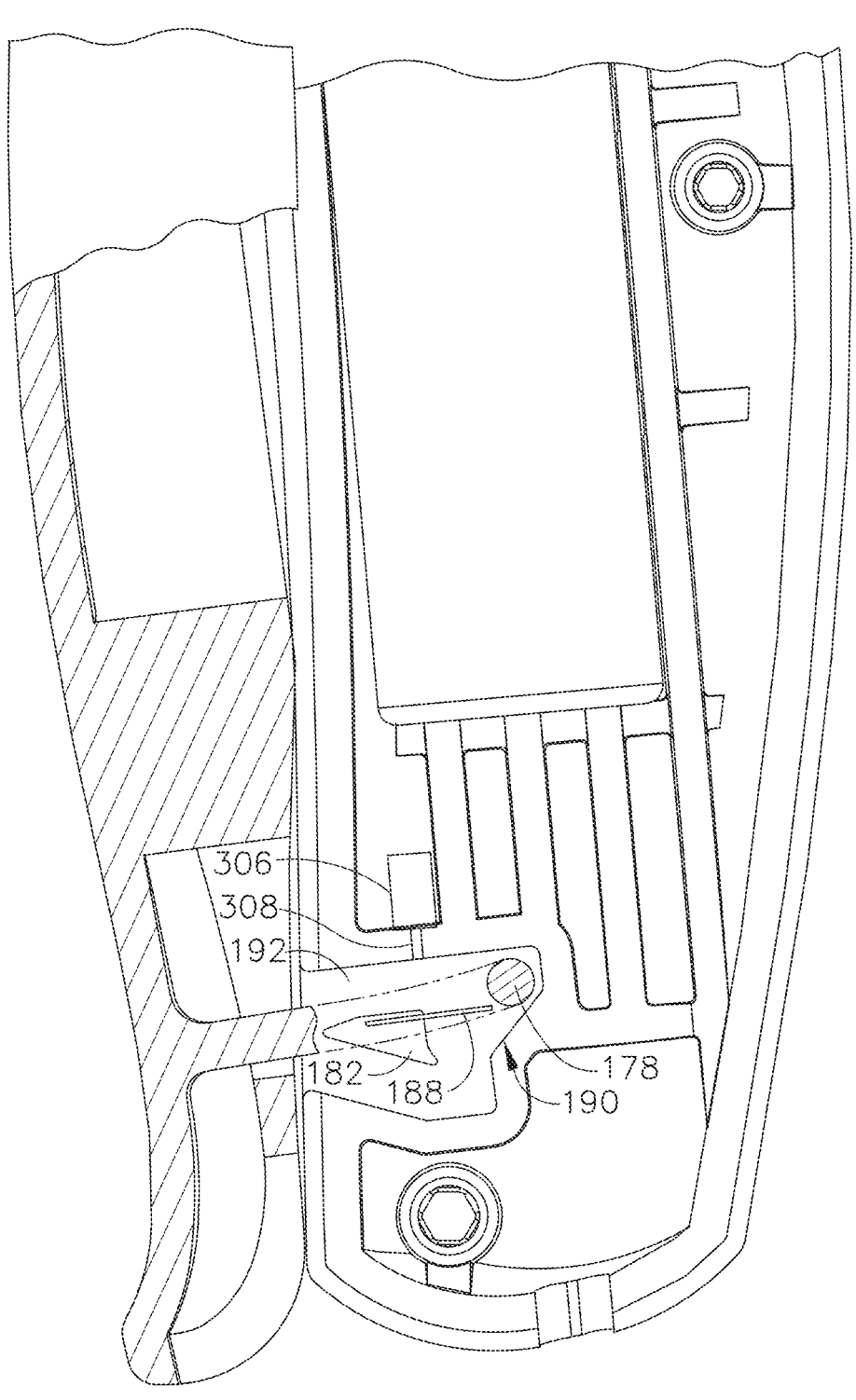
Figure 22:
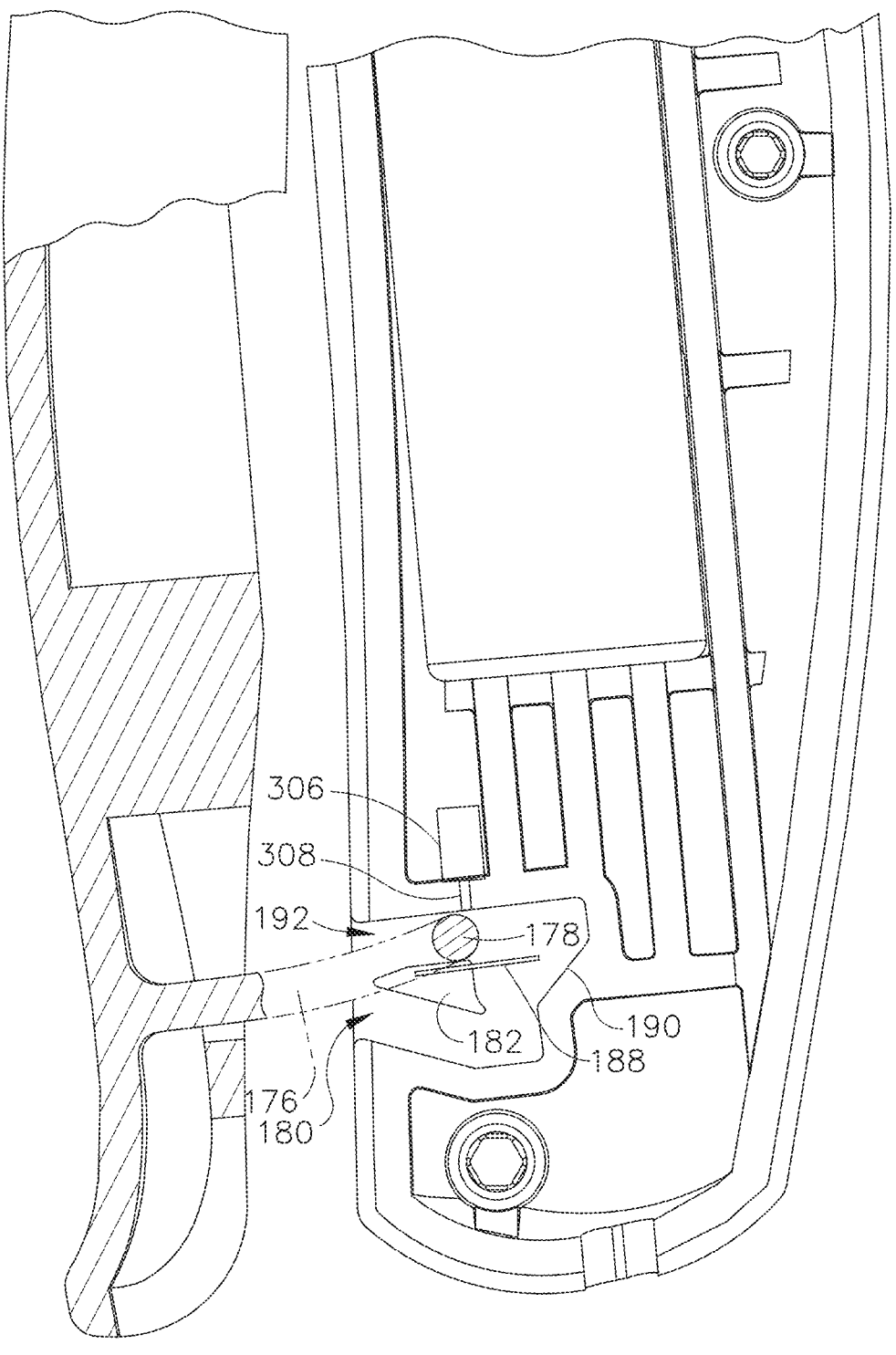

To unlock the closure trigger 18, the operator may further squeeze the closure trigger 18, causing the pin 178 to engage a sloped backwall 190 of the opening 180, forcing the pin 178 upward past the flexible stop 188, as shown in FIGS. 20 and 21. The pin 178 is then free to travel out an upper channel 192 in the opening 180 such that the closure trigger 18 is no longer locked to the pistol grip portion 26, as shown in FIG. 22. In order to prevent the anvil 24 from inadvertently being opened while a firing operation is in progress, the solenoid 306 may be positioned within the pistol grip 26 such that the plunger 308 of the solenoid 306, when energized, is received into the upper channel 192. When received into the upper channel 192, the plunger 308 operates to prevent passage of the pin 178 therethrough. Accordingly, unlocking the closure trigger 18 is prevented until the plunger 308 is retracted from the upper channel 192 at the conclusion of the firing operation.

Figures 23A, 23B:
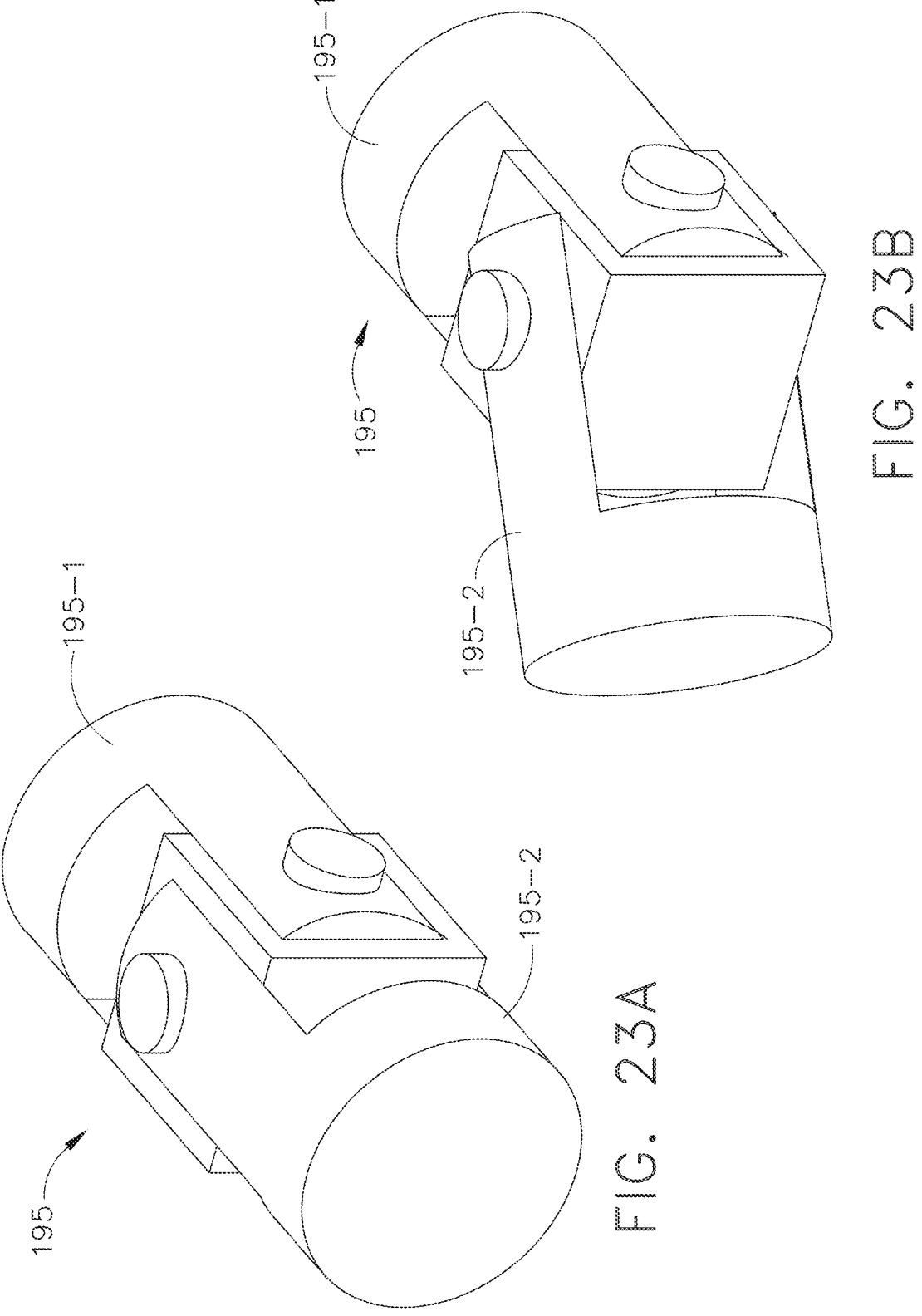
FIGS. 23A and 23B show a universal joint ("u-joint") that may be employed at the articulation point of the instrument according to various embodiments of the present invention.
Figure 24A:
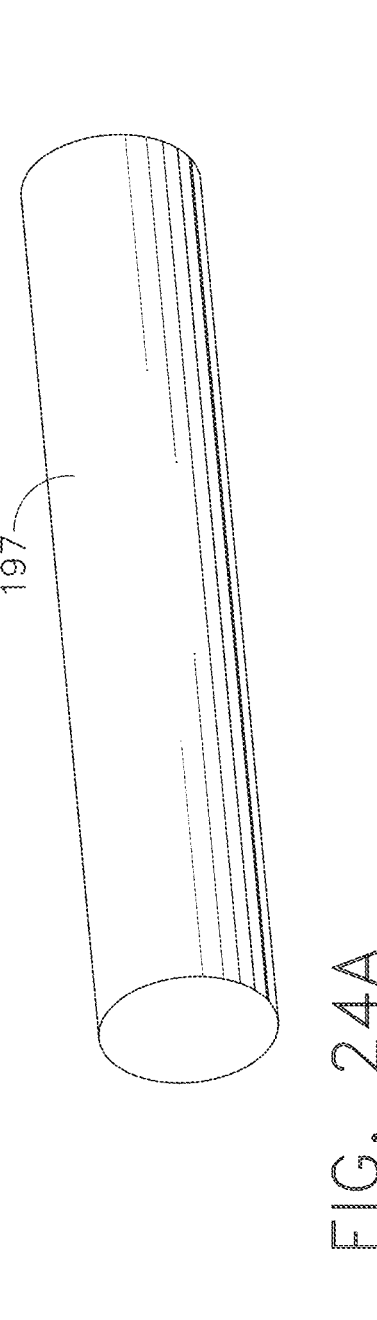
FIGS. 24A and 24B show a torsion cable that may be employed at the articulation point of the instrument according to various embodiments of the present invention.
Figure 24B:
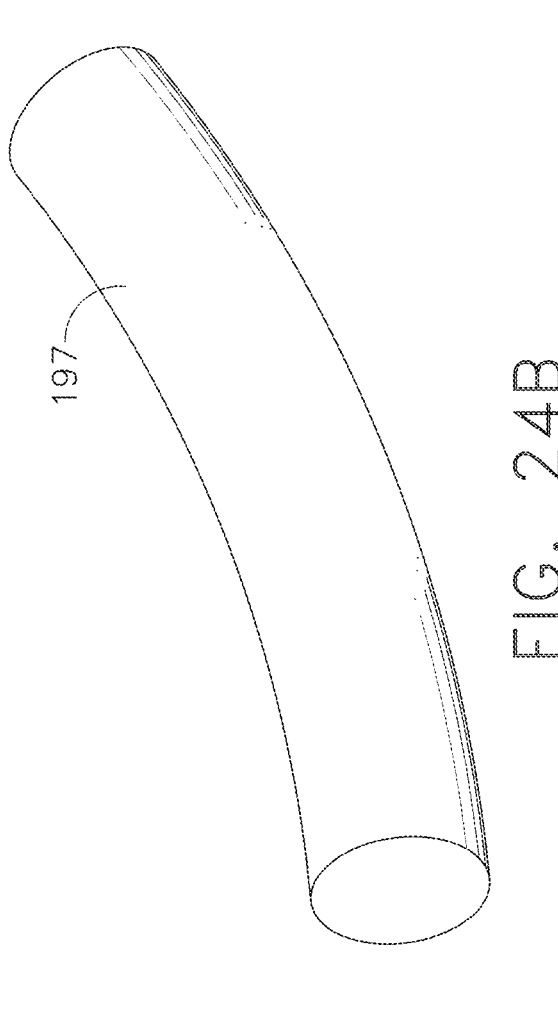
Figure 25:
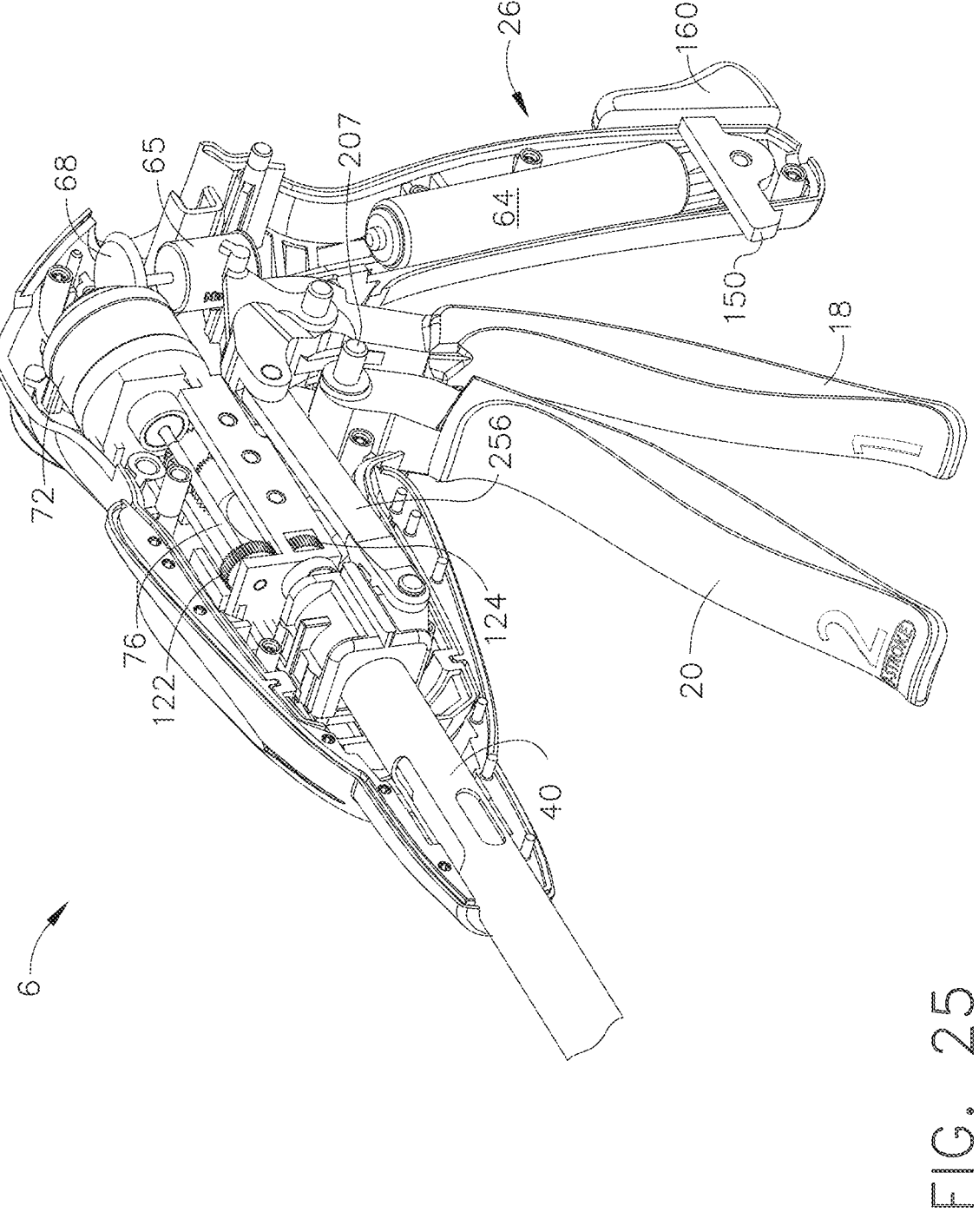
FIGS. 25-31 illustrate a surgical cutting and fastening instrument with power assist according to another embodiment of the present invention.
Figure 26:
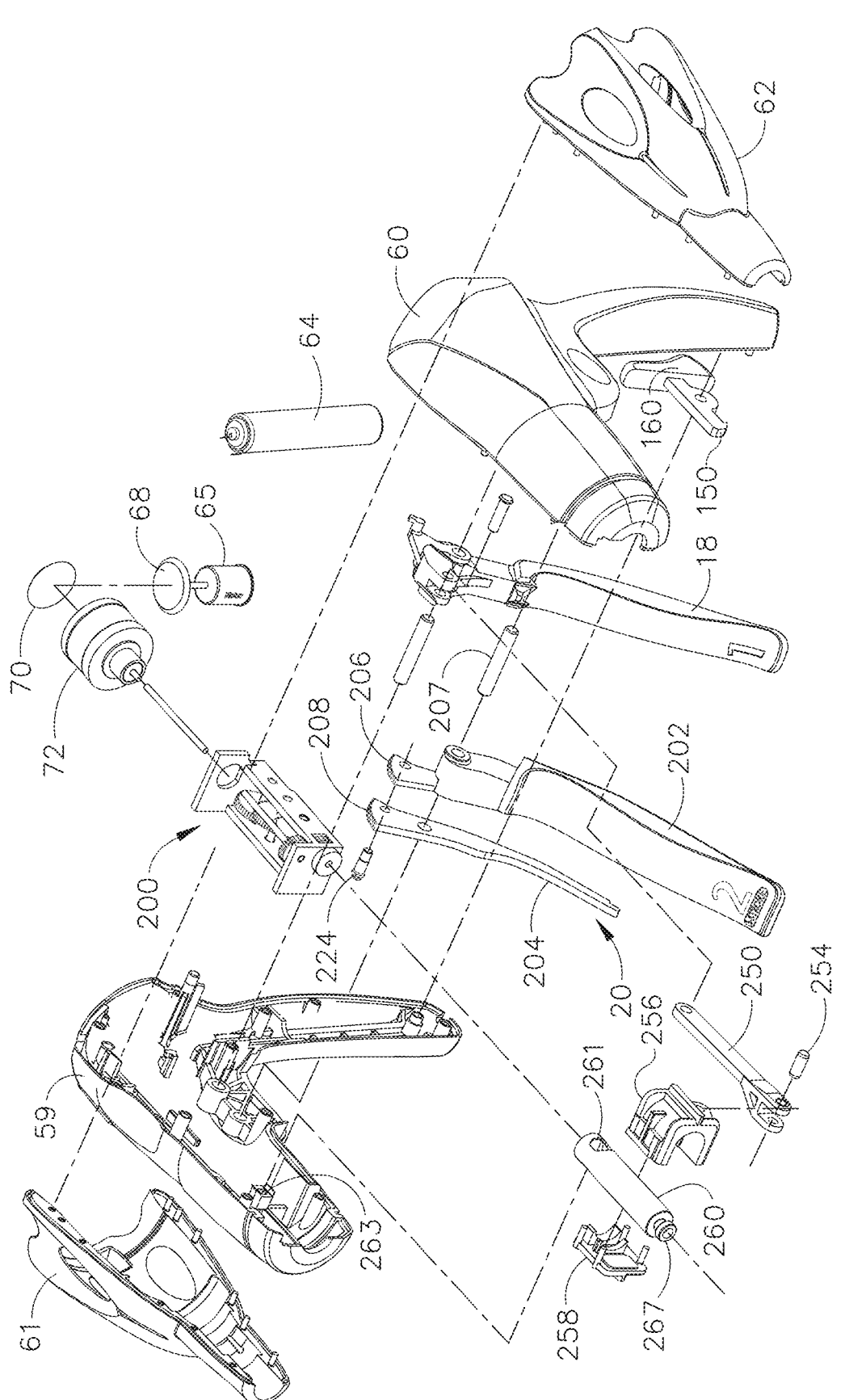
Figure 27:
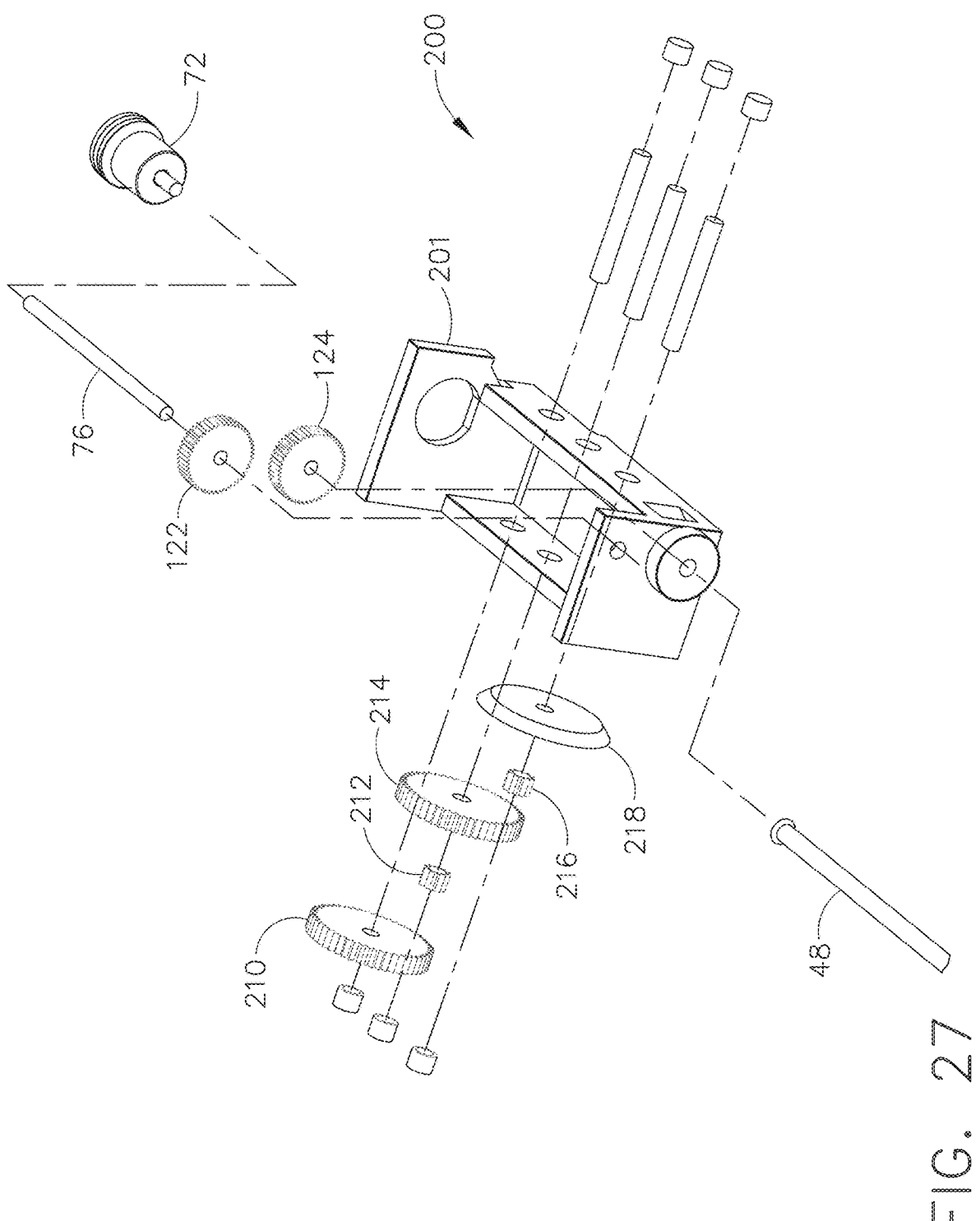
Figure 28:
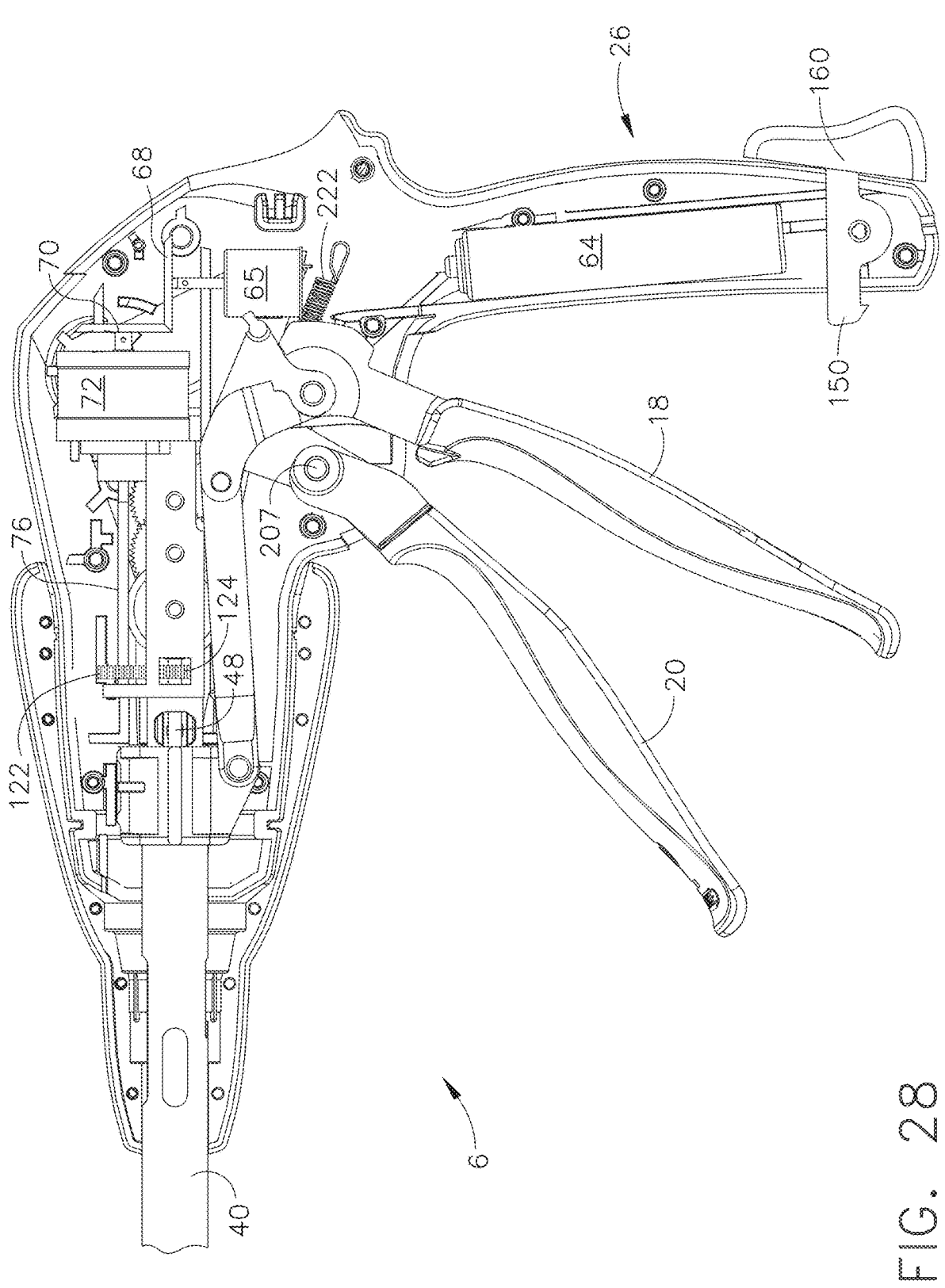
Figure 29:
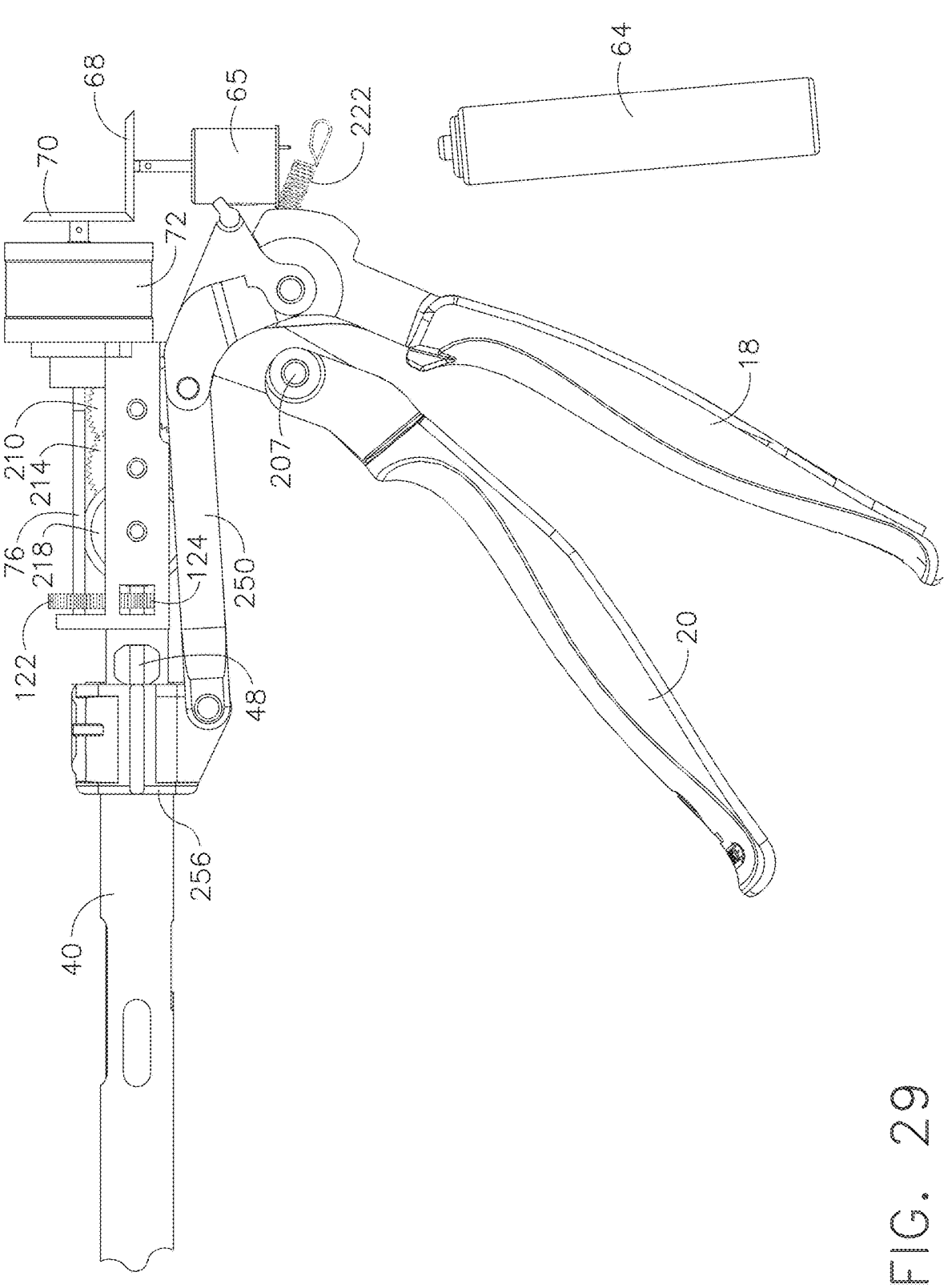
Figure 30:
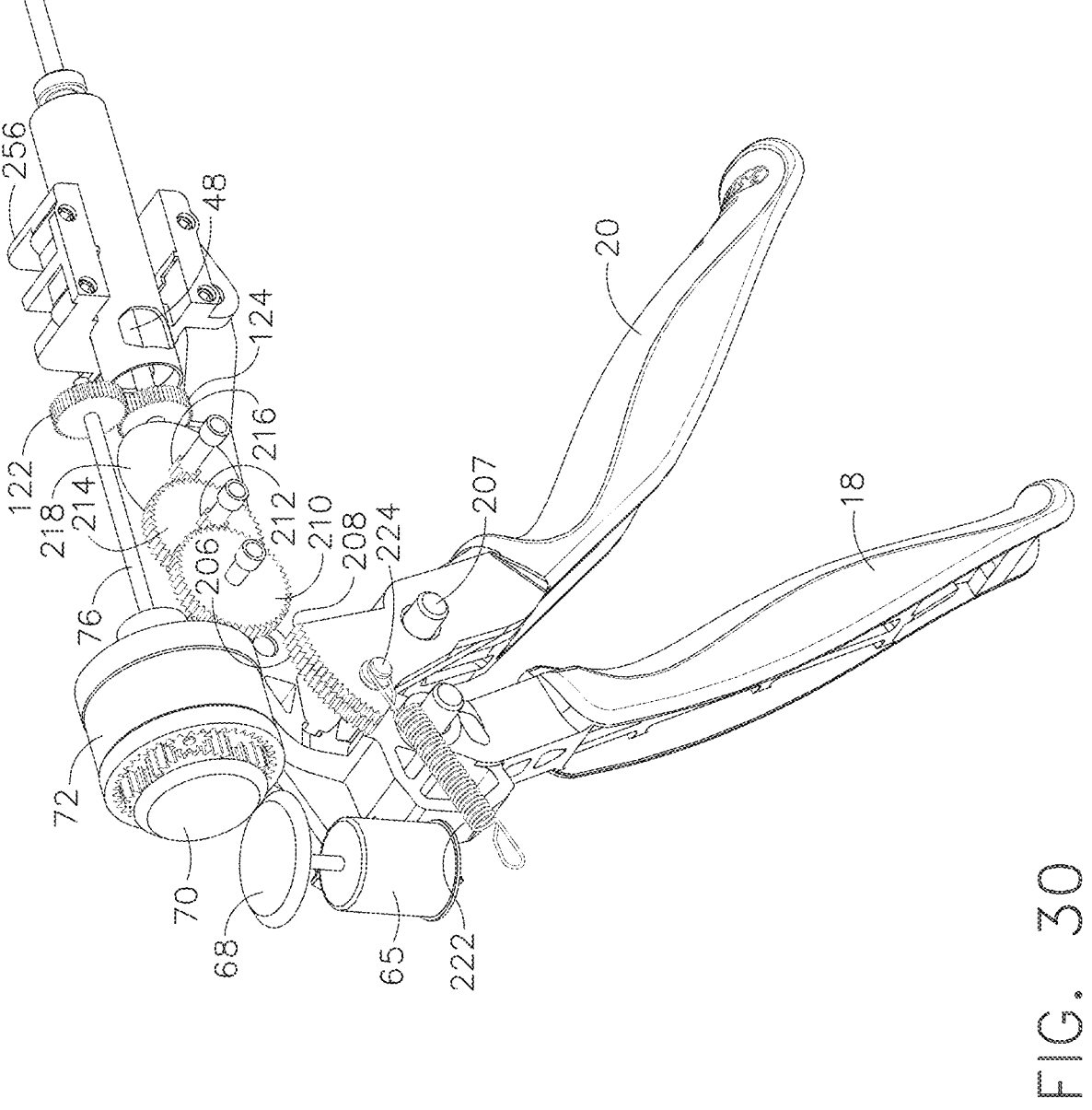
Figure 31:
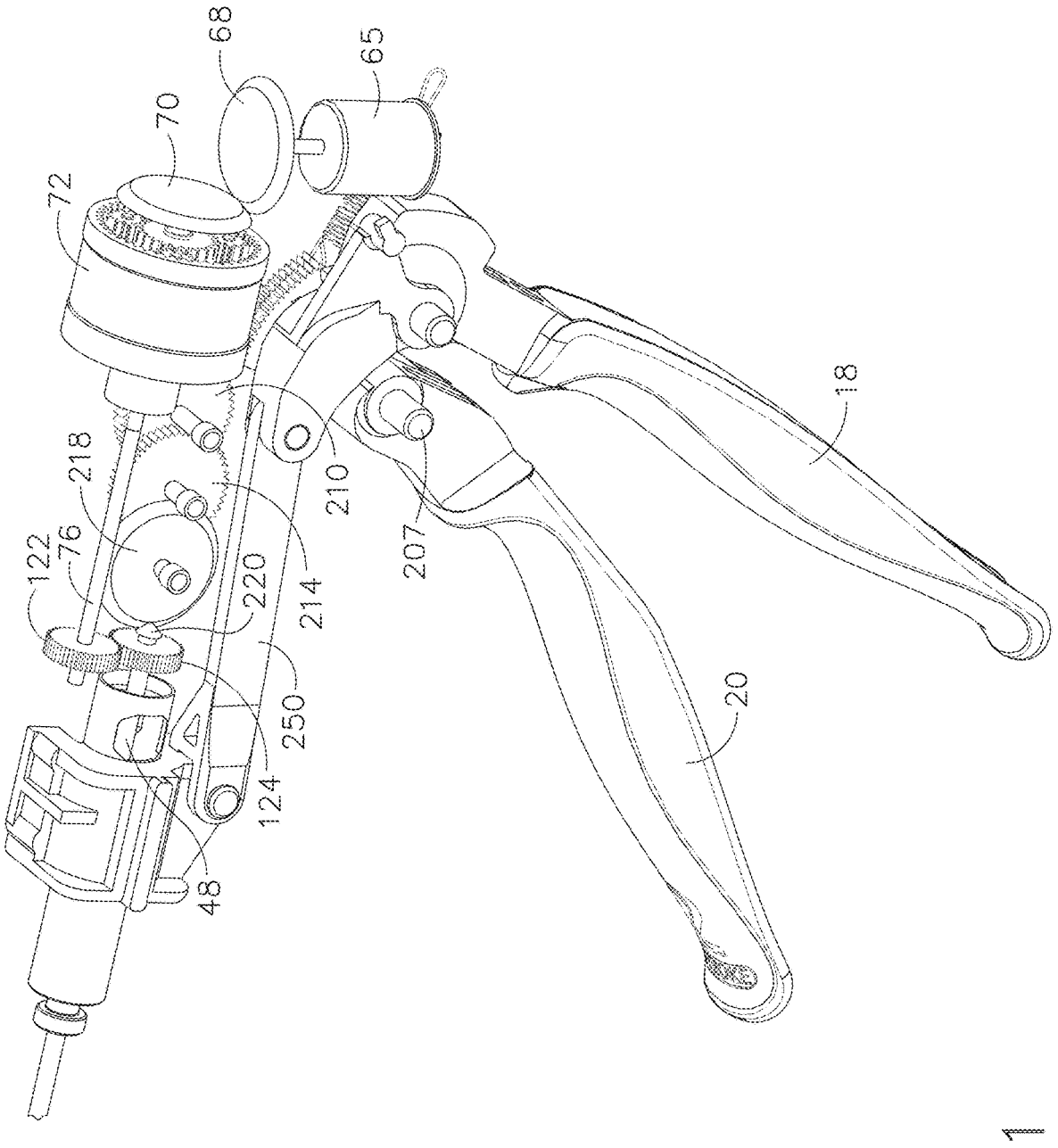

FIGS. 23A-B show a universal joint ("u-joint") 195. The second piece 195-2 of the u-joint 195 rotates in a horizontal plane in which the first piece 195-1 lies. FIG. 23A shows the u-joint 195 in a linear (180°) orientation and FIG. 23B shows the u-joint 195 at approximately a 150° orientation. The u-joint 195 may be used instead of the bevel gears 52a-c (see FIG. 4, for example) at the articulation point 14 of the main drive shaft assembly to articulate the end effector 12. FIGS. 24A-B show a torsion cable 197 that may be used in lieu of both the bevel gears 52a-c and the u-joint 195 to realize articulation of the end effector 12.

FIGS. 25-31 illustrate another embodiment of a motorized, two-stroke surgical cutting and fastening instrument 10 with power assist according to another embodiment of the present invention. The embodiment of FIGS. 25-31 is similar to that of FIGS. 6-10 except that instead of the helical gear drum 80, the embodiment of FIGS. 23-28 includes an alternative gear drive assembly. The embodiment of FIGS. 25-31 includes a gear box assembly 200 including a number of gears disposed in a frame 201, wherein the gears are connected between the planetary gear 72 and the pinion gear 124 at the proximal end of the drive shaft 48. As explained further below, the gear box assembly 200 provides feedback to the user via the firing trigger 20 regarding the deployment and loading force of the end effector 12. Also, the user may provide power to the system via the gear box assembly 200 to assist the deployment of the end effector 12. In that sense, like the embodiments described above, the embodiment of FIGS. 23-32 is another power assist motorized instrument 10 that provides feedback to the user regarding the loading force experienced by the instrument.

In the illustrated embodiment, the firing trigger 20 includes two pieces: a main body portion 202 and a stiffening portion 204. The main body portion 202 may be made of plastic, for example, and the stiffening portion 204 may be made out of a more rigid material, such as metal. In the illustrated embodiment, the stiffening portion 204 is adjacent to the main body portion 202, but according to other embodiments, the stiffening portion 204 could be disposed inside the main body portion 202. A pivot pin 207 may be inserted through openings in the firing trigger pieces 202, 204 and may be the point about which the firing trigger 20 rotates. In addition, a spring 222 may bias the firing trigger 20 to rotate in a counter clockwise direction. The spring 222 may have a distal end connected to a pin 224 that is connected to the pieces 202, 204 of the firing trigger 20. The proximate end of the spring 222 may be connected to one of the handle exterior lower side pieces 59, 60.

In the illustrated embodiment, both the main body portion 202 and the stiffening portion 204 includes gear portions 206, 208 (respectively) at their upper end portions. The gear portions 206, 208 engage a gear in the gear box assembly 200, as explained below, to drive the main drive shaft assembly and to provide feedback to the user regarding the deployment of the end effector 12.

The gear box assembly 200 may include as shown, in the illustrated embodiment, six (6) gears. A first gear 210 of the gear box assembly 200 engages the gear portions 206, 208 of the firing trigger 20. In addition, the first gear 210 engages a smaller second gear 212, the smaller second gear 212 being coaxial with a large third gear 214. The third gear 214 engages a smaller fourth gear 216, the smaller fourth gear being coaxial with a fifth gear 218. The fifth gear 218 is a 90° bevel gear that engages a mating 90° bevel gear 220 (best shown in FIG. 31) that is connected to the pinion gear 124 that drives the main drive shaft 48.

In operation, when the user retracts the firing trigger 20, a run motor sensor (not shown) is activated, which may provide a signal to the motor 65 to rotate at a rate proportional to the extent or force with which the operator is retracting the firing trigger 20. This causes the motor 65 to rotate at a speed proportional to the signal from the sensor. The sensor is not shown for this embodiment, but it could be similar to the run motor sensor 110 described above. The sensor could be located in the handle 6 such that it is depressed when the firing trigger 20 is retracted. Also, instead of a proportional-type sensor, an on/off type sensor may be used.

Rotation of the motor 65 causes the bevel gears 68, 70 to rotate, which causes the planetary gear 72 to rotate, which causes, via the drive shaft 76, the ring gear 122 to rotate. The ring gear 122 meshes with the pinion gear 124, which is connected to the main drive shaft 48. Thus, rotation of the pinion gear 124 drives the main drive shaft 48, which causes actuation of the cutting/stapling operation of the end effector 12.

Forward rotation of the pinion gear 124 in turn causes the bevel gear 220 to rotate, which causes, by way of the rest of the gears of the gear box assembly 200, the first gear 210 to rotate. The first gear 210 engages the gear portions 206, 208 of the firing trigger 20, thereby causing the firing trigger 20 to rotate counter clockwise when the motor 65 provides forward drive for the end effector 12 (and to rotate counter clockwise when the motor 65 rotates in reverse to retract the end effector 12). In that way, the user experiences feedback regarding loading force and deployment of the end effector 12 by way of the user's grip on the firing trigger 20. Thus, when the user retracts the firing trigger 20, the operator will experience a resistance related to the load force experienced by the end effector 12. Similarly, when the operator releases the firing trigger 20 after the cutting/stapling operation so that it can return to its original position, the user will experience a clockwise rotation force from the firing trigger 20 that is generally proportional to the reverse speed of the motor 65.

It should also be noted that in this embodiment the user can apply force (either in lieu of or in addition to the force from the motor 65) to actuate the main drive shaft assembly (and hence the cutting/stapling operation of the end effector 12) through retracting the firing trigger 20. That is, retracting the firing trigger 20 causes the gear portions 206, 208 to rotate counter clockwise, which causes the gears of the gear box assembly 200 to rotate, thereby causing the pinion gear 124 to rotate, which causes the main drive shaft 48 to rotate.

Although not shown in FIGS. 25-31, the instrument 10 may further include reverse motor and stop motor sensors. As described above, the reverse motor and stop motor sensors may detect, respectively, the end of the cutting stroke (full deployment of the knife 32) and the end of retraction operation (full retraction of the knife 32). A similar circuit to that described above in connection with FIG. 11 may be used to appropriately power the motor 65.

FIGS. 32-36 illustrate a two-stroke, motorized surgical cutting and fastening instrument 10 with power assist according to another embodiment. The embodiment of FIGS. 32-36 is similar to that of FIGS. 25-31 except that in the embodiment of FIGS. 32-36, the firing trigger 20 includes a lower portion 228 and an upper portion 230. Both portions 228, 230 are connected to and pivot about a pivot pin 207 that is disposed through each portion 228, 230. The upper portion 230 includes a gear portion 232 that engages the first gear 210 of the gear box assembly 200. The spring 222 is connected to the upper portion 230 such that the upper portion is biased to rotate in the clockwise direction. The upper portion 230 may also include a lower arm 234 that contacts an upper surface of the lower portion 228 of the firing trigger 20 such that when the upper portion 230 is caused to rotate clockwise the lower portion 228 also rotates clockwise, and when the lower portion 228 rotates counter clockwise the upper portion 230 also rotates counter clockwise. Similarly, the lower portion 228 includes a rotational stop 238 that engages a shoulder of the upper portion 230. In that way, when the upper portion 230 is caused to rotate counter clockwise the lower portion 228 also rotates counter clockwise, and when the lower portion 228 rotates clockwise the upper portion 230 also rotates clockwise.

The illustrated embodiment also includes the run motor sensor 110 that communicates a signal to the motor 65 that, in various embodiments, may cause the motor 65 to rotate at a speed proportional to the force applied by the operator when retracting the firing trigger 20. The sensor 110 may be, for example, a rheostat or some other variable resistance sensor, as explained herein. In addition, the instrument 10 may include reverse motor sensor 130 that is tripped or switched when contacted by a front face 242 of the upper portion 230 of the firing trigger 20. When activated, the reverse motor sensor 130 sends a signal to the motor 65 to reverse direction. Also, the instrument 10 may include a stop motor sensor 142 that is tripped or actuated when contacted by the lower portion 228 of the firing trigger 20. When activated, the stop motor sensor 142 sends a signal to stop the reverse rotation of the motor 65.

Figure 32:
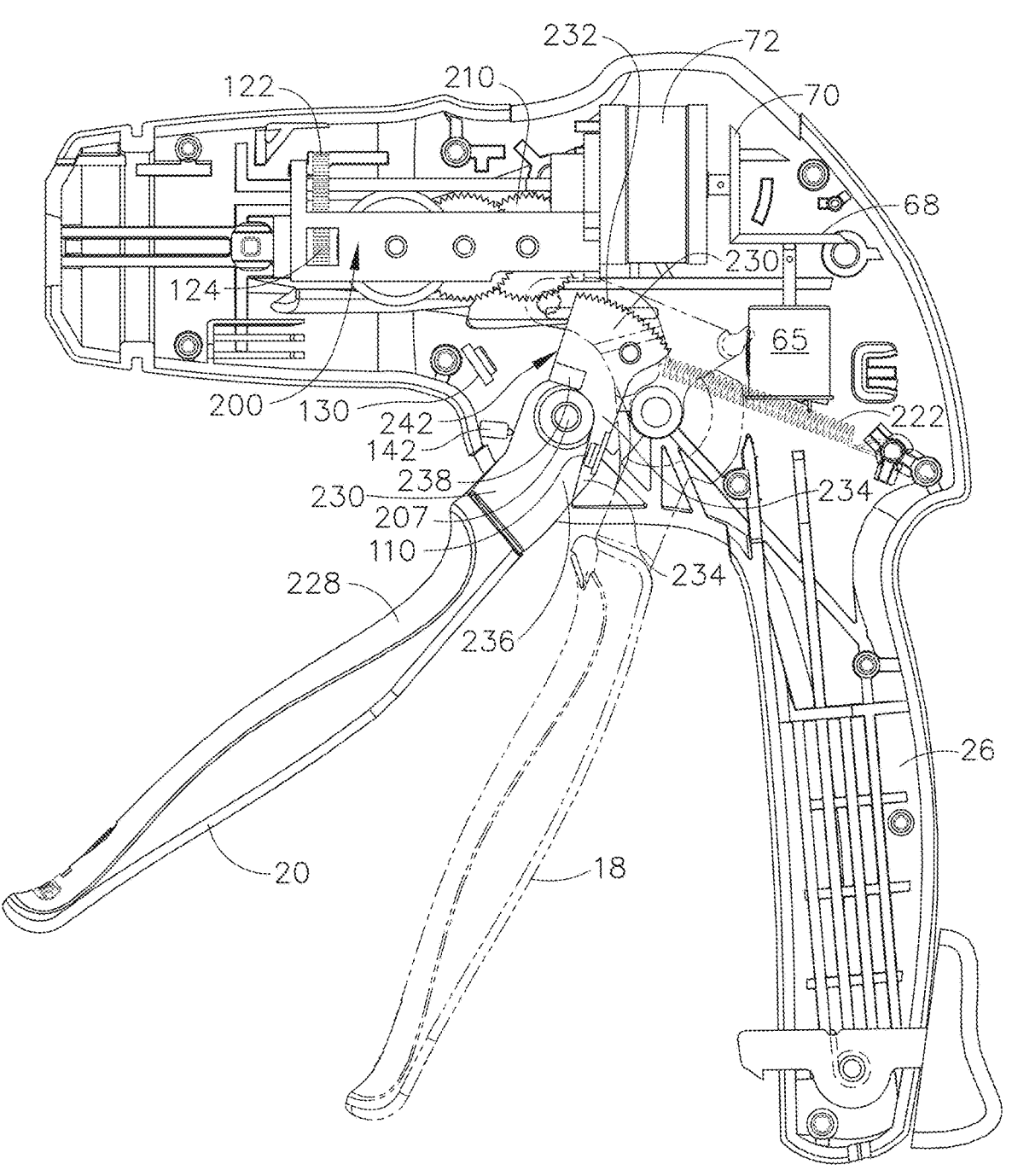
FIGS. 32-36 illustrate a surgical cutting and fastening instrument with power assist according to yet another embodiment of the present invention.
Figure 33:
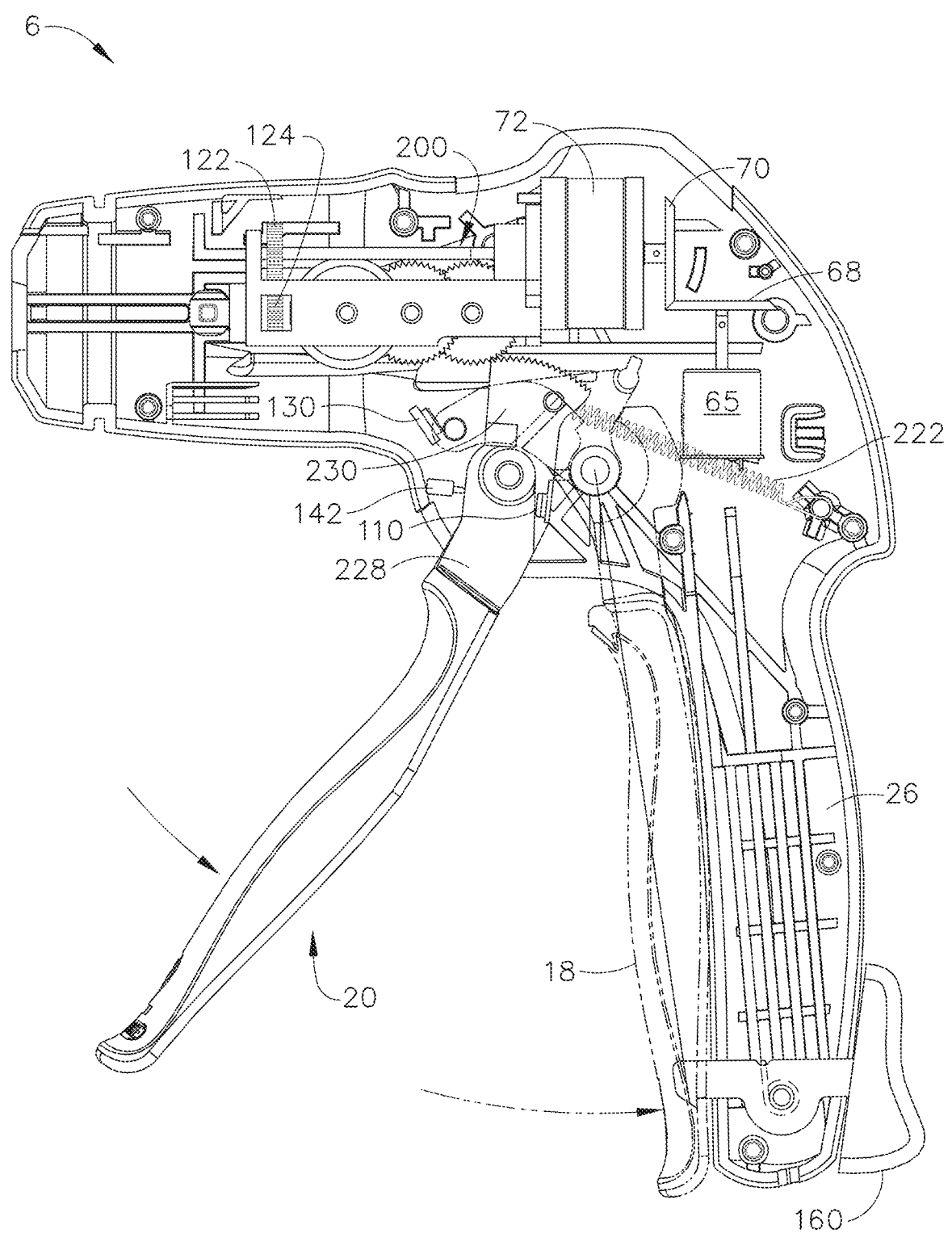
Figure 34:
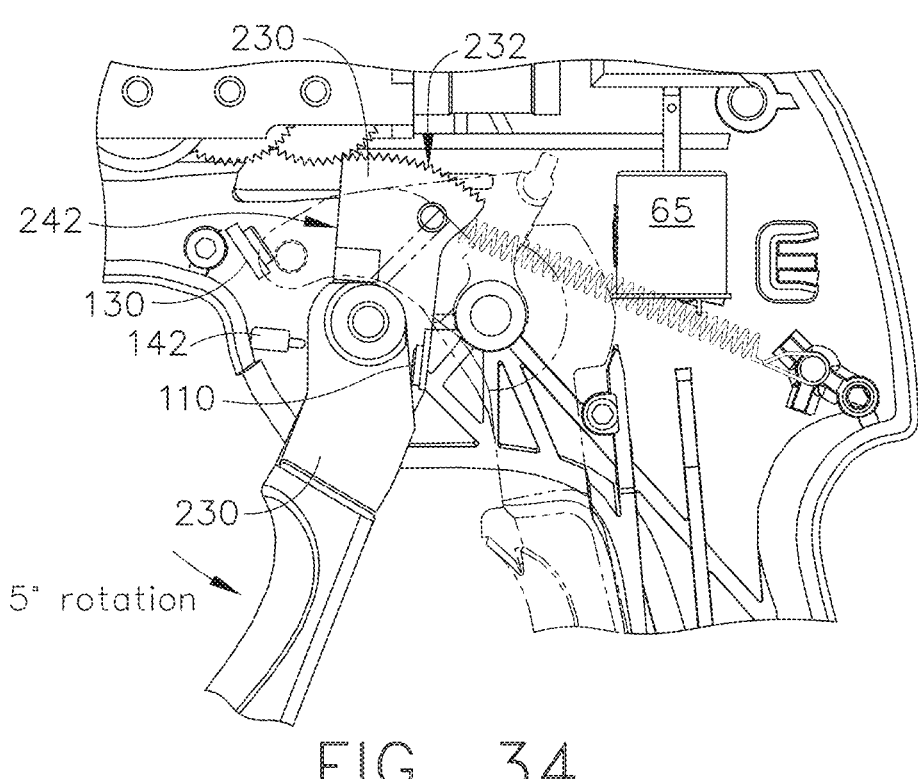
Figure 35:
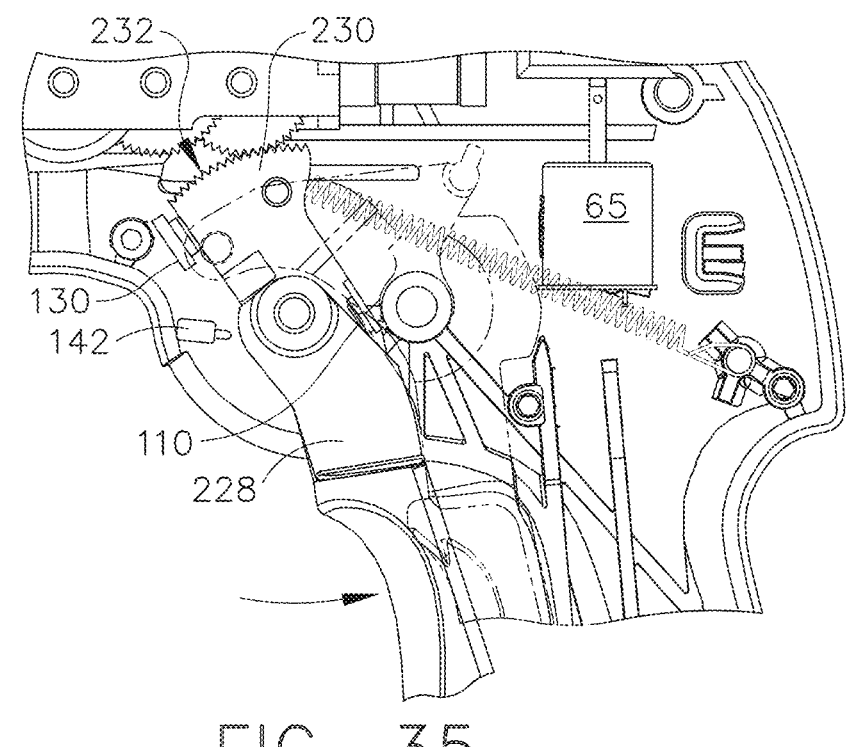
Figure 36:
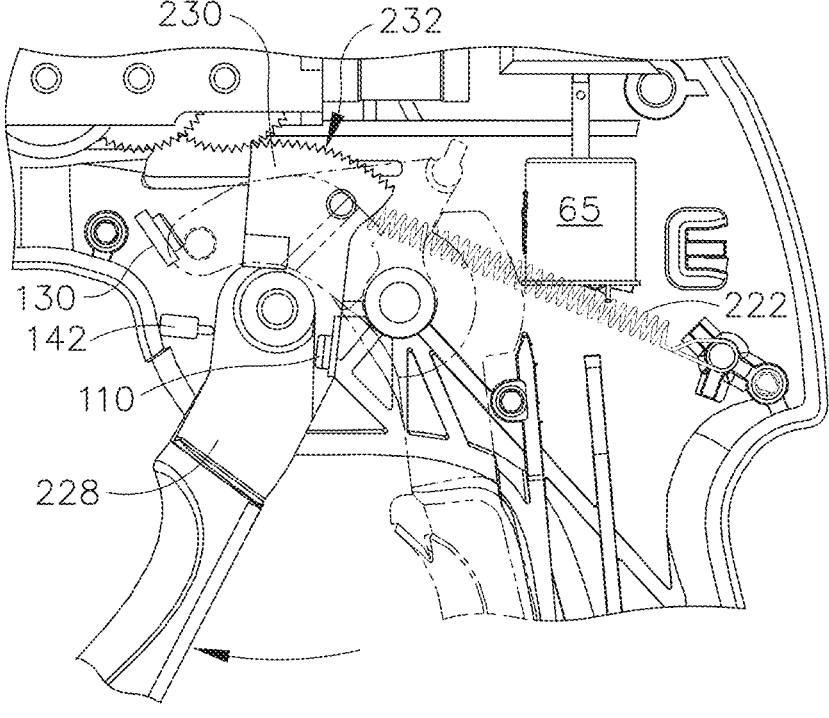

In operation, when an operator retracts the closure trigger 18 into the locked position, the firing trigger 20 is retracted slightly (through mechanisms known in the art, including U.S. Pat. No. 6,978,921 to Frederick Shelton, I V et. al and U.S. Pat. No. 6,905,057 to Jeffery S. Swayze et. al, which are incorporated herein by reference) so that the user can grasp the firing trigger 20 to initiate the cutting/stapling operation, as shown in FIGS. 32 and 33. At that point, as shown in FIG. 33, the gear portion 232 of the upper portion 230 of the firing trigger 20 moves into engagement with the first gear 210 of the gear box assembly 200. When the operator retracts the firing trigger 20, according to various embodiments, the firing trigger 20 may rotate a small amount, such as five degrees, before tripping the run motor sensor 110, as shown in FIG. 34. Activation of the sensor 110 causes the motor 65 to forward rotate at a rate proportional to the retraction force applied by the operator. The forward rotation of the motor 65 causes, as described above, the main drive shaft 48 to rotate, which causes the knife 32 in the end effector 12 to be deployed (i.e., begin traversing the channel 22). Rotation of the pinion gear 124, which is connected to the main drive shaft 48, causes the gears 210-220 in the gear box assembly 200 to rotate. Since the first gear 210 is in engagement with the gear portion 232 of the upper portion 230 of the firing trigger 20, the upper portion 232 is caused to rotate counter clockwise, which causes the lower portion 228 to also rotate counter clockwise.

When the knife 32 is fully deployed (i.e., at the end of the cutting stroke), the front face 242 of the upper portion 230 trips the reverse motor sensor 130, which sends a signal to the motor 65 to reverse rotational directional. This causes the main drive shaft assembly to reverse rotational direction to retract the knife 32. Reverse rotation of the main drive shaft assembly also causes the gears 210-220 in the gear box assembly to reverse direction, which causes the upper portion 230 of the firing trigger 20 to rotate clockwise, which causes the lower portion 228 of the firing trigger 20 to rotate clockwise until the lower portion 228 trips or actuates the stop motor sensor 142 when the knife 32 is fully retracted, which causes the motor 65 to stop. In that way, the user experiences feedback regarding deployment of the end effector 12 by way of the user's grip on the firing trigger 20. Thus, when the user retracts the firing trigger 20, the operator will experience a resistance related to the deployment of the end effector 12 and, in particular, to the loading force experienced by the knife 32. Similarly, when the operator releases the firing trigger 20 after the cutting/stapling operation so that it can return to its original position, the user will experience a clockwise rotation force from the firing trigger 20 that is generally proportional to the reverse speed of the motor 65.

It should also be noted that in this embodiment the user can apply force (either in lieu of or in addition to the force from the motor 65) to actuate the main drive shaft assembly (and hence the cutting/stapling operation of the end effector 12) through retracting the firing trigger 20. That is, retracting the firing trigger 20 causes the gear portion 232 of the upper portion 230 to rotate counter clockwise, which causes the gears of the gear box assembly 200 to rotate, thereby causing the pinion gear 124 to rotate, which causes the main drive shaft assembly to rotate.

The above-described embodiments employed power-assist user feedback systems, with or without adaptive control (e.g., using a sensor 110, 130, and 142 outside of the closed loop system of the motor 65, gear drive train, and end effector 12) for a two-stroke, motorized surgical cutting and fastening instrument. That is, force applied by the user in retracting the firing trigger 20 may be added to the force applied by the motor 65 by virtue of the firing trigger 20 being geared into (either directly or indirectly) the gear drive train between the motor 65 and the main drive shaft 48. In other embodiments of the present invention, the user may be provided with tactile feedback regarding the position of the knife 32 in the end effector, but without having the firing trigger 20 geared into the gear drive train. FIGS. 37-40 illustrate a motorized surgical cutting and fastening instrument with such a tactile position feedback system.

In the illustrated embodiment of FIGS. 37-40, the firing trigger 20 may have a lower portion 228 and an upper portion 230, similar to the instrument 10 shown in FIGS. 32-36. Unlike the embodiment of FIG. 32-36, however, the upper portion 230 does not have a gear portion that mates with part of the gear drive train. Instead, the instrument includes a second motor 265 with a threaded rod 266 threaded therein. The threaded rod 266 reciprocates longitudinally in and out of the motor 265 as the motor 265 rotates, depending on the direction of rotation. The instrument 10 also includes an encoder 268 that is responsive to the rotations of the main drive shaft 48 for translating the incremental angular motion of the main drive shaft 48 (or other component of the main drive assembly) into a corresponding series of digital signals, for example. In the illustrated embodiment, the pinion gear 124 includes a proximate drive shaft 270 that connects to the encoder 268.

The instrument 10 also includes a control circuit (not shown), which may be implemented using a microcontroller or some other type of integrated circuit, that receives the digital signals from the encoder 268. Based on the signals from the encoder 268, the control circuit may calculate the stage of deployment of the knife 32 in the end effector 12. That is, the control circuit can calculate if the knife 32 is fully deployed, fully retracted, or at an intermittent stage. Based on the calculation of the stage of deployment of the end effector 12, the control circuit may send a signal to the second motor 265 to control its rotation to thereby control the reciprocating movement of the threaded rod 266.

Figure 37:
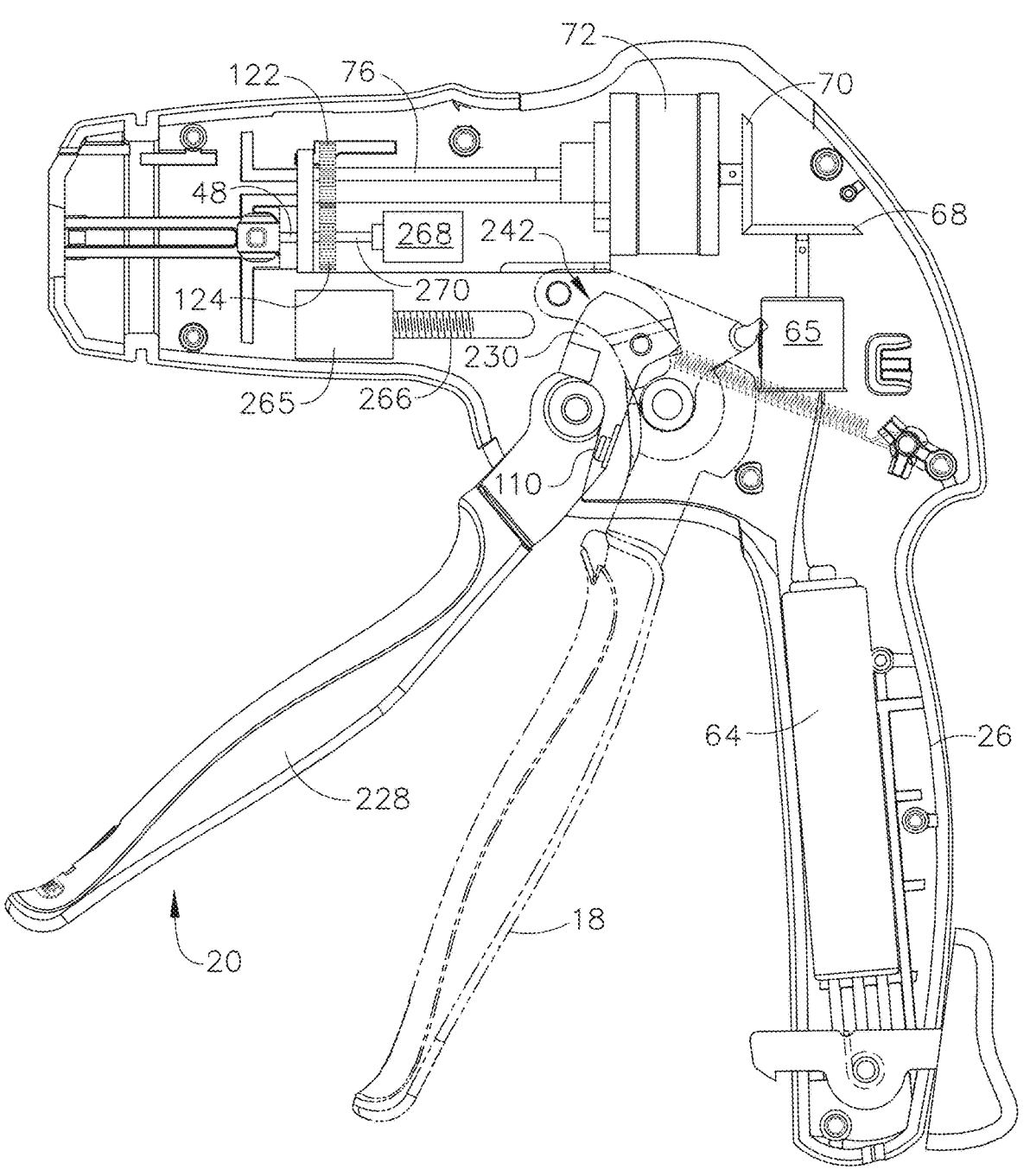
FIGS. 37-40 illustrate a surgical cutting and fastening instrument with tactile feedback to embodiments of the present invention.
Figure 38:
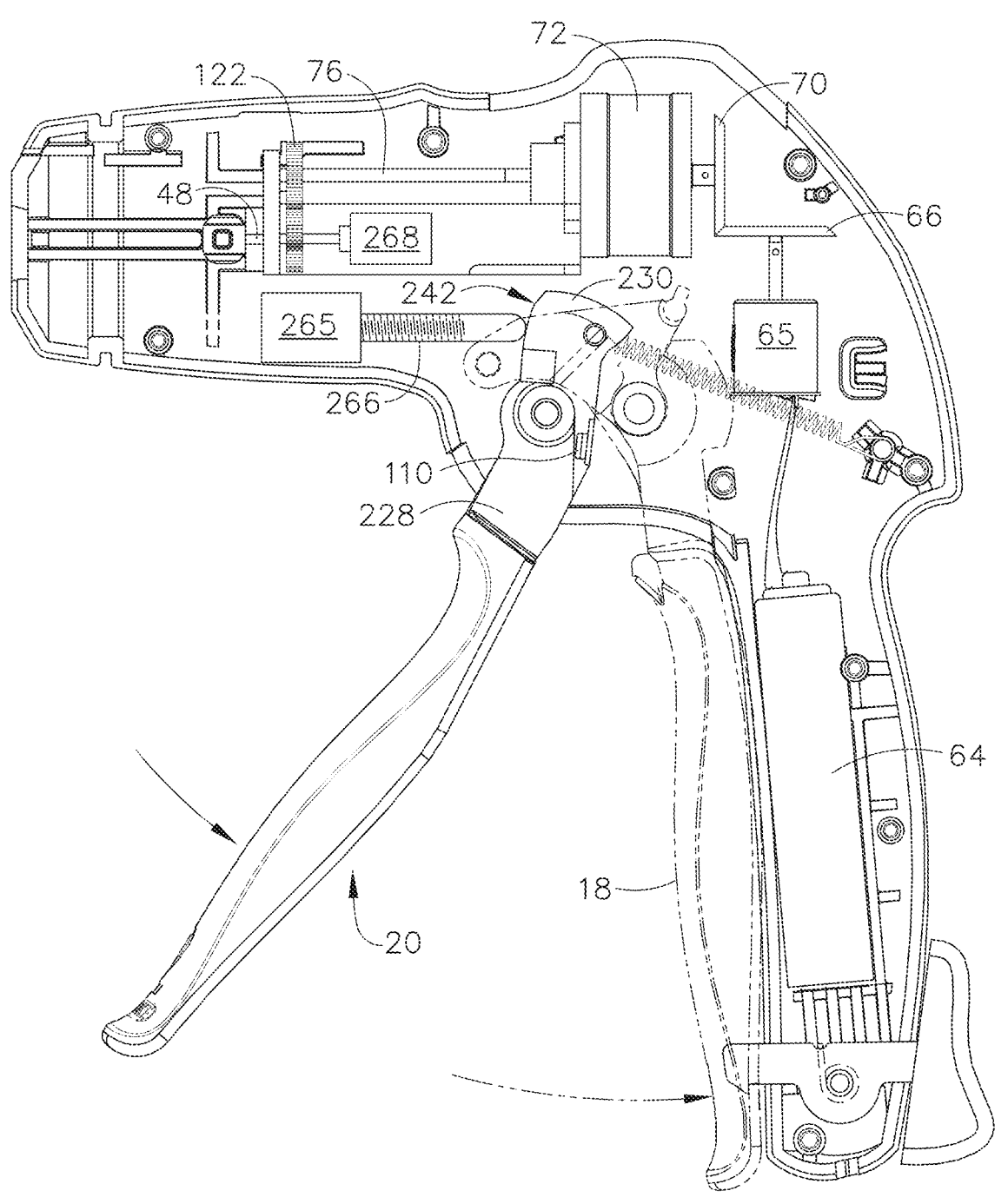
Figure 39:
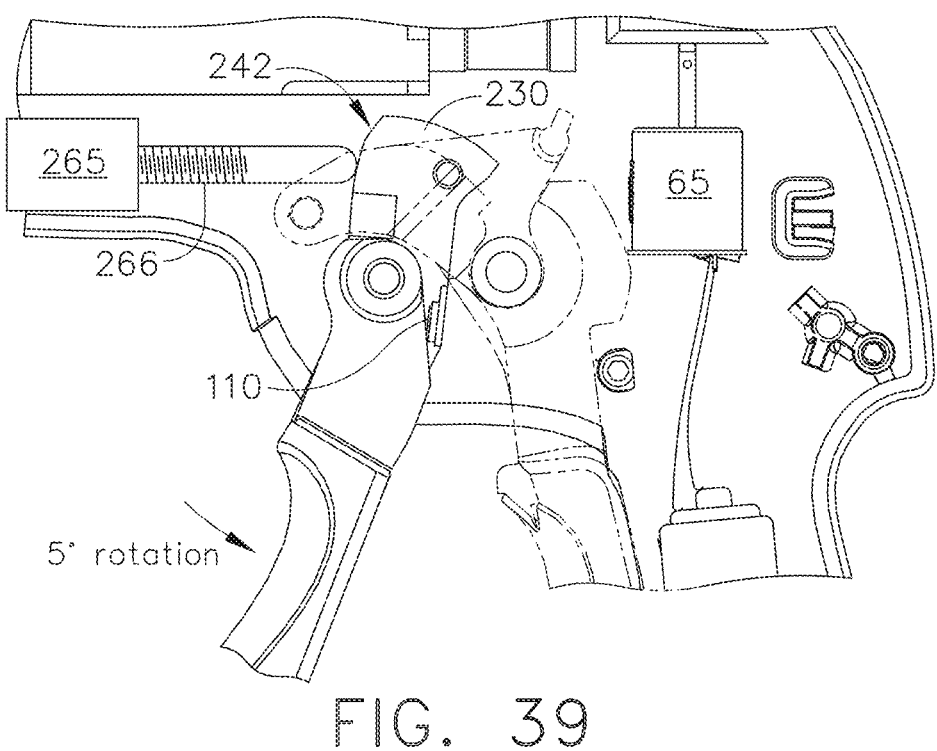
Figure 40:
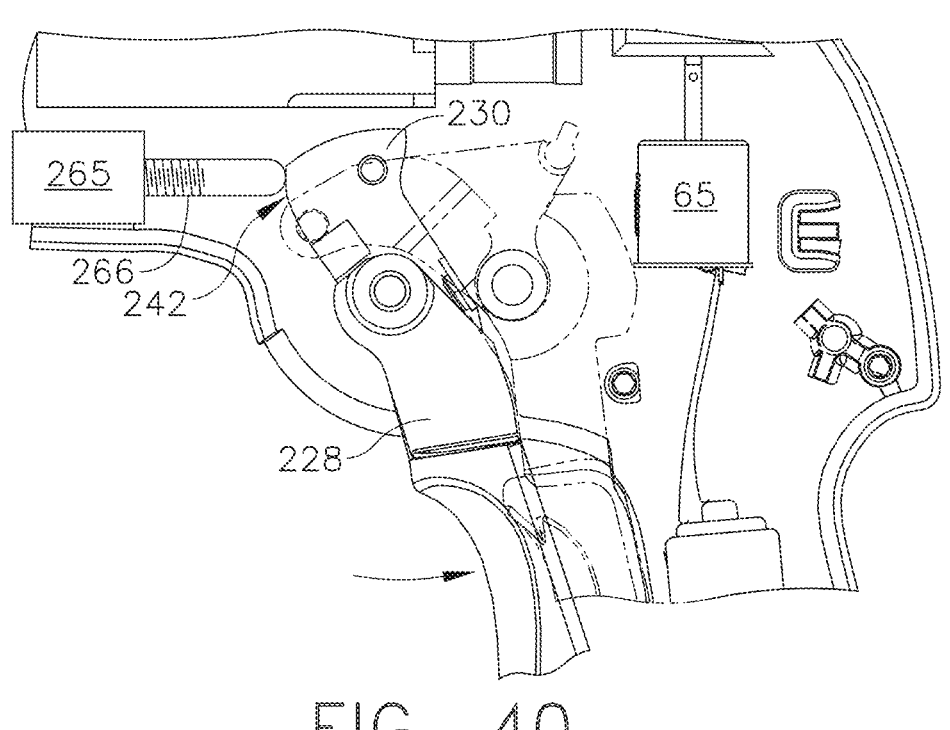

In operation, as shown in FIG. 37, when the closure trigger 18 is not locked into the clamped position, the firing trigger 20 rotated away from the pistol grip portion 26 of the handle 6 such that the front face 242 of the upper portion 230 of the firing trigger 20 is not in contact with the proximate end of the threaded rod 266. When the operator retracts the closure trigger 18 and locks it in the clamped position, the firing trigger 20 rotates slightly towards the closure trigger 20 so that the operator can grasp the firing trigger 20, as shown in FIG. 38. In this position, the front face 242 of the upper portion 230 contacts the proximate end of the threaded rod 266.

As the user then retracts the firing trigger 20, after an initial rotational amount (e.g. 5 degrees of rotation) the run motor sensor 110 may be activated such that, as explained above, the sensor 110 sends a signal to the motor 65 to cause it to rotate at a forward speed proportional to the amount of retraction force applied by the operator to the firing trigger 20. Forward rotation of the motor 65 causes the main drive shaft 48 to rotate via the gear drive train, which causes the knife 32 and sled 33 to travel down the channel 22 and sever tissue clamped in the end effector 12. The control circuit receives the output signals from the encoder 268 regarding the incremental rotations of the main drive shaft assembly and sends a signal to the second motor 265 to cause the second motor 265 to rotate, which causes the threaded rod 266 to retract into the motor 265. This allows the upper portion 230 of the firing trigger 20 to rotate counter clockwise, which allows the lower portion 228 of the firing trigger to also rotate counter clockwise. In that way, because the reciprocating movement of the threaded rod 266 is related to the rotations of the main drive shaft assembly, the operator of the instrument 10, by way of his/her grip on the firing trigger 20, experiences tactile feedback as to the position of the end effector 12. The retraction force applied by the operator, however, does not directly affect the drive of the main drive shaft assembly because the firing trigger 20 is not geared into the gear drive train in this embodiment.

By virtue of tracking the incremental rotations of the main drive shaft assembly via the output signals from the encoder 268, the control circuit can calculate when the knife 32 is fully deployed (i.e., fully extended). At this point, the control circuit may send a signal to the motor 65 to reverse direction to cause retraction of the knife 32. The reverse direction of the motor 65 causes the rotation of the main drive shaft assembly to reverse direction, which is also detected by the encoder 268. Based on the reverse rotation detected by the encoder 268, the control circuit sends a signal to the second motor 265 to cause it to reverse rotational direction such that the threaded rod 266 starts to extend longitudinally from the motor 265. This motion forces the upper portion 230 of the firing trigger 20 to rotate clockwise, which causes the lower portion 228 to rotate clockwise. In that way, the operator may experience a clockwise force from the firing trigger 20, which provides feedback to the operator as to the retraction position of the knife 32 in the end effector 12. The control circuit can determine when the knife 32 is fully retracted. At this point, the control circuit may send a signal to the motor 65 to stop rotation.

According to other embodiments, rather than having the control circuit determine the position of the knife 32, reverse motor and stop motor sensors may be used, as described above. In addition, rather than using a proportional sensor 110 to control the rotation of the motor 65, an on/off switch or sensor can be used. In such an embodiment, the operator would not be able to control the rate of rotation of the motor 65. Rather, it would rotate at a preprogrammed rate.

Figure 41:
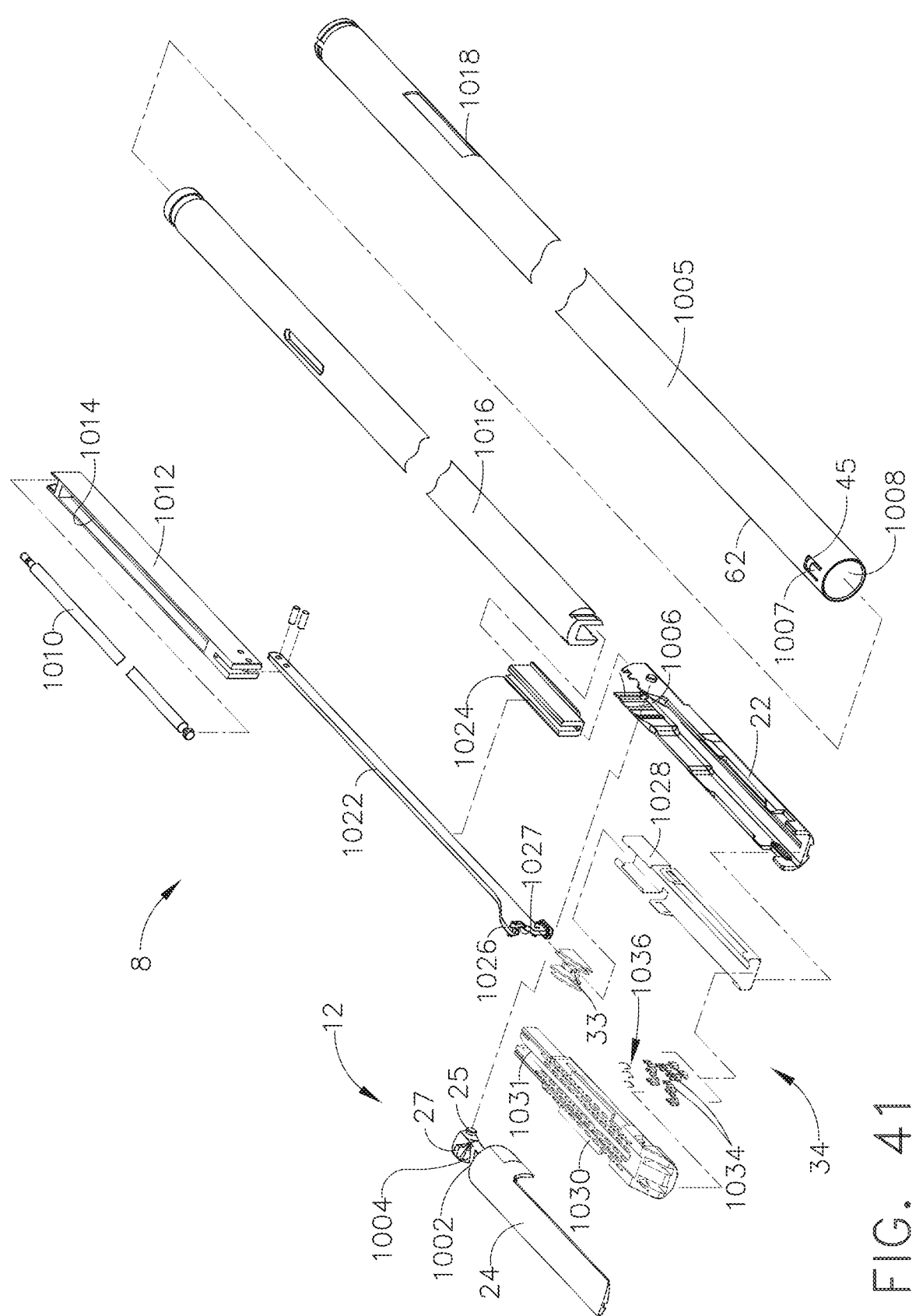
FIG. 41 illustrates an exploded view of an end effector and shaft of the instrument according to various embodiments of the present invention.
Figure 42:
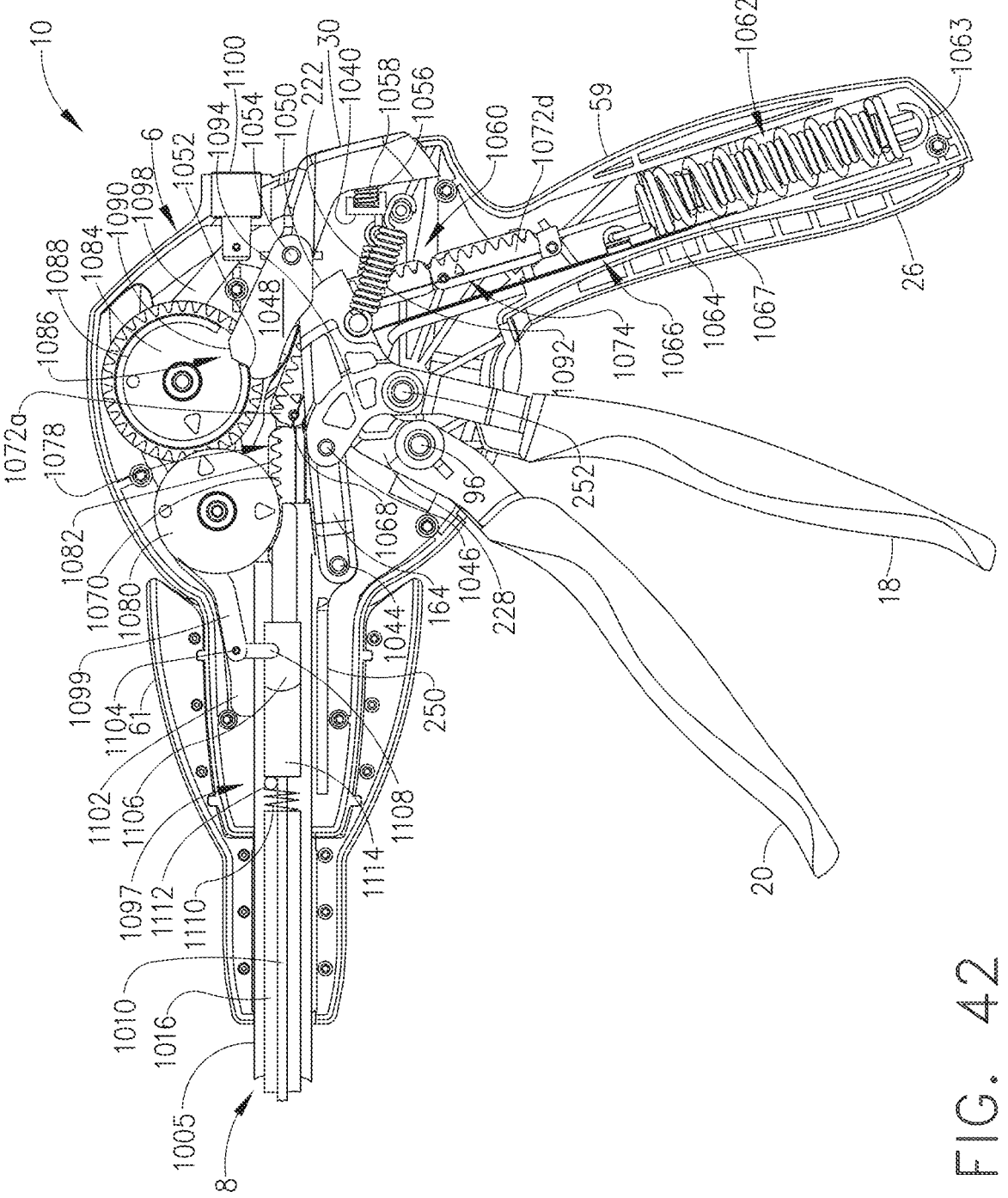
FIG. 42 illustrates a side view of the handle of a mechanically instrument according to various embodiments of the present invention.
Figure 43:
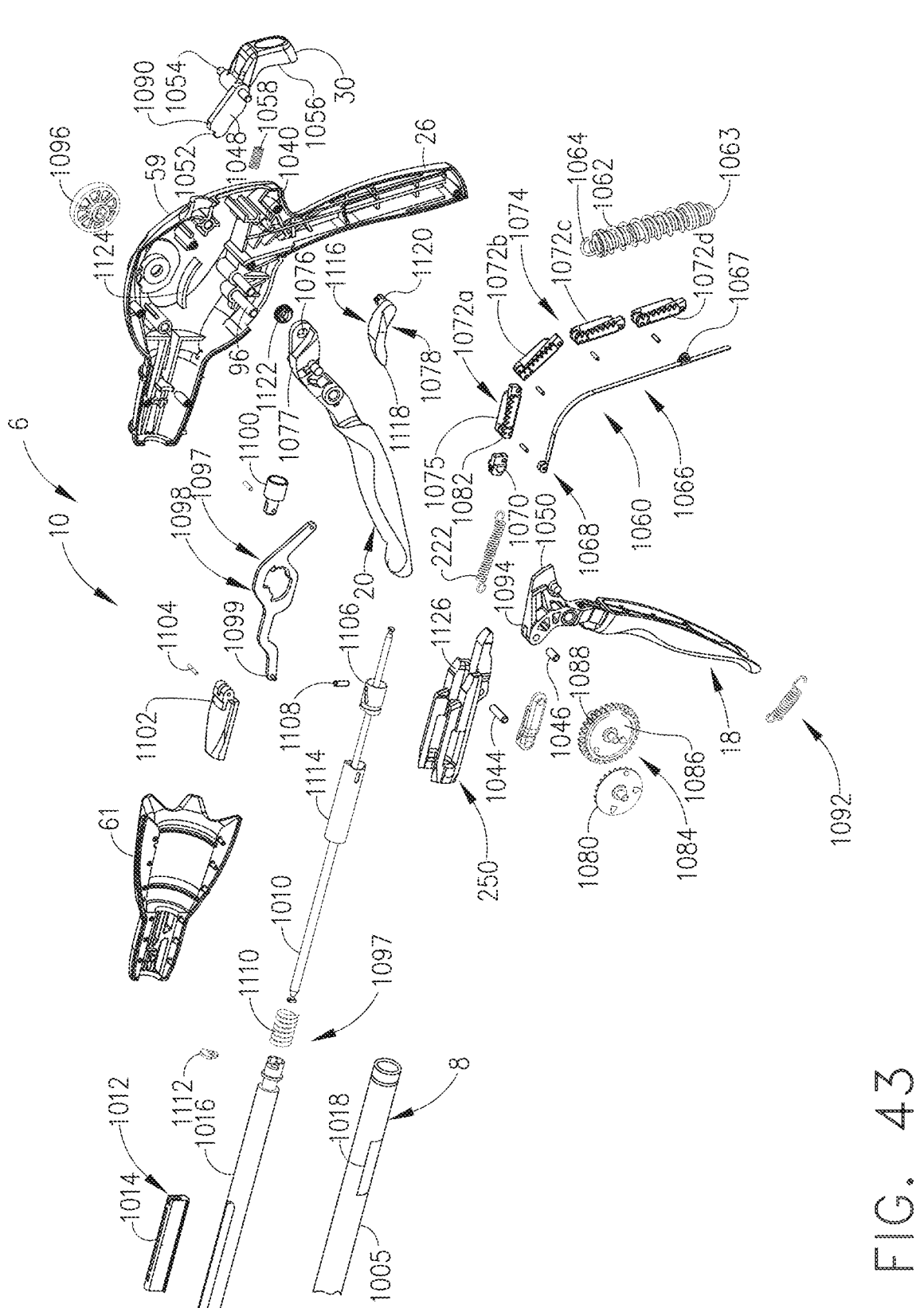
FIG. 43 illustrates an exploded view of the handle of the mechanically actuated instrument of FIG. 42.

FIGS. 41-43 illustrate an exemplary embodiment of a mechanically actuated endocutter, and in particular the handle 6, shaft 8 and end effector 12 thereof. Further details of a mechanically actuated endocutter may be found in U.S. patent application Ser. No. 11/052,632 entitled, MULTI-STROKE MECHANISM WITH AUTOMATIC END OF STROKE RETRACTION, now U.S. Pat. No. 7,083,075 which is incorporated herein by reference. With reference to FIG. 41, the end effector 12 responds to the closure motion from the handle 6 (not depicted in FIG. 41) first by including an anvil face 1002 connecting to an anvil proximal end 1004 that includes laterally projecting anvil pivot pins 25 that are proximal to a vertically projecting anvil tab 27. The anvil pivot pins 25 translate within kidney shaped openings 1006 in the staple channel 22 to open and close anvil 24 relative to channel 22. The tab 27 engages a bent tab 1007 extending inwardly in tab opening 45 on a distal end 1008 of the closure tube 1005, the latter distally terminating in a distal edge 1008 that pushes against the anvil face 1002. Thus, when the closure tube 1005 moves proximally from its open position, the bent tab 1007 of the closure tube 1005 draws the anvil tab 27 proximally, and the anvil pivot pins 25 follow the kidney shaped openings 1006 of the staple channel 22 causing the anvil 24 to simultaneously translate proximally and rotate upward to the open position. When the closure tube 1005 moves distally, the bent tab 1007 in the tab opening 45 releases from the anvil tab 27 and the distal edge 1008 pushes on the anvil face 1002, closing the anvil 24.

With continued reference to FIG. 41, the shaft 8 and end effector 12 also include components that respond to a firing motion of a firing rod 1010. In particular, the firing rod 1010 rotatably engages a firing trough member 1012 having a longitudinal recess 1014. Firing trough member 1012 moves longitudinally within frame 1016 in direct response to longitudinal motion of firing rod 1010. A longitudinal slot 1018 in the closure tube 1005 operably couples with the right and left exterior side handle pieces 61, 62 of the handle 6 (not shown in FIG. 41). The length of the longitudinal slot 1018 in the closure tube 1005 is sufficiently long to allow relative longitudinal motion with the handle pieces 61, 62 to accomplish firing and closure motions respectively with the coupling of the handle pieces 61, 62 passing on through a longitudinal slot 1020 in the frame 1016 to slidingly engage the longitudinal recess 1014 in the frame trough member 1012.

The distal end of the frame trough member 1012 is attached to a proximal end of a firing bar 1022 that moves within the frame 1016, specifically within a guide 1024 therein, to distally project the knife 32 into the end effector 12. The end effector 12 includes a staple cartridge 34 that is actuated by the knife 32. The staple cartridge 34 has a tray 290 that holds a staple cartridge body 1030, a wedge sled driver 33, staple drivers 1034 and staples 1036. It will be appreciated that the wedge sled driver 33 longitudinally moves within a firing recess (not shown) located between the cartridge tray 290 and the cartridge body 1030. The wedge sled driver 33 presents camming surfaces that contact and lift the staple drivers 1034 upward, driving the staples 1036. The staple cartridge body 1030 further includes a proximally open, vertical slot 1031 for passage of the knife 32. Specifically, a cutting surface 1027 is provided along a distal end of knife 32 to cut tissue after it is stapled.

It should be appreciated that the shaft 8 is shown in FIG. 4 as a non-articulating shaft. Nonetheless, applications of the present invention may include instruments capable of articulation, for example, as such shown above with reference to FIGS. 1-4 and described in the following U.S. patents and patent applications, the disclosure of each being hereby incorporated by reference in their entirety: (1) SURGICAL INSTRUMENT INCORPORATING AN ARTICULATION MECHANISM HAVING ROTATION ABOUT THE LONGITUDINAL AXIS, by Frederick E. Shelton I V, Brian J. Hemmelgarn, Jeffrey S. Swayze, Kenneth S. Wales, filed Jul. 9, 2003, now U.S. Pat. No. 7,111,769; (2) SURGICAL STAPLING INSTRUMENT INCORPORATING AN ARTICULATION JOINT FOR A FIRING TRACK, U.S. Pat. No. 6,786,382, to Brian J. Hemmelgarn; (3) A SURGICAL INSTRUMENT WITH A LATERAL-MOVING ARTICULATION CONTROL, U.S. Pat. No. 6,981,628, to Jeffrey S. Swayze; (4) SURGICAL STAPLING INSTRUMENT INCORPORATING A TAPERED FIRING BAR FOR INCREASED FLEXIBILITY AROUND THE ARTICULATION JOINT, U.S. Pat. No. 6,964,363, to Frederick E. Shelton I V, Michael Setser, Bruce Weisenburgh II; and (5) SURGICAL STAPLING INSTRUMENT HAVING ARTICULATION JOINT SUPPORT PLATES FOR SUPPORTING A FIRING BAR, U.S. Patent Application Publication No. 2005/0006431, by Jeffrey S. Swayze, Joseph Charles Hueil, filed Jul. 9, 2003, now U.S. Pat. No. 7,055, 731.

FIGS. 42-43 show an embodiment of the handle 6 that is configured for use in a mechanically actuated endocutter along with the embodiment of the shaft 8 and end effector 12 as shown above in FIG. 41. It will be appreciated that any suitable handle design may be used to mechanically close and fire the end effector 12. In FIGS. 42-43, the handle 6 of the surgical stapling and severing instrument 10 includes a linked transmission firing mechanism 1060 that provides features such as increased strength, reduced handle size, minimized binding, etc.

Closure of the end effector 12 (not shown in FIGS. 42-43) is caused by depressing the closure trigger 18 toward the pistol grip 26 of handle 6. The closure trigger 18 pivots about a closure pivot pin 252 that is coupled to right and left exterior lower side pieces 59, 60 the handle 6, causing an upper portion 1094 of the closure trigger 18 to move forward. The closure tube 1005 receives this closure movement via the closure yoke 250 that is pinned to a closure link 1042 and to the upper portion 1094 of the closure trigger 18 respectively by a closure yoke pin 1044 and a closure link pin 1046.

In the fully open position of FIG. 42, the upper portion 1094 of the closure trigger 18 contacts and holds a locking arm 1048 of the pivoting closure release button 30 in the position shown. When the closure trigger 18 reaches its fully depressed position, the closure trigger 18 releases the locking arm 1048 and an abutting surface 1050 rotates into engagement with a distal rightward notch 1052 of the pivoting locking arm 1048, holding the closure trigger 18 in this clamped or closed position. A proximal end of the locking arm 1048 pivots about a lateral pivotal connection 1054 with the pieces 59, 60 to expose the closure release button 30. An intermediate, distal side 1056 of the closure release button 30 is urged proximally by a compression spring 1058, which is compressed between a housing structure 1040 and closure release button 30. The result is that the closure release button 30 urges the locking arm 1048 counterclockwise (when viewed from the left) into locking contact with the abutting surface 1050 of closure trigger 18, which prevents unclamping of closure trigger 18 when the linked transmission firing system 1040 is in an un-retracted condition.

With the closure trigger 18 retracted and fully depressed, the firing trigger 20 is unlocked and may be depressed toward the pistol grip 26, multiple times in this embodiment, to effect firing of the end effector 12. As depicted, the linked transmission firing mechanism 1060 is initially retracted, urged to remain in this position by a combination tension/ compression spring 1062 that is constrained within the pistol grip 26 of the handle 6, with its nonmoving end 1063 connected to the pieces 59, 60 and a moving end 1064 connected to a downwardly flexed and proximal, retracted end 1067 of a steel band 1066.

A distally-disposed end 1068 of the steel band 1066 is attached to a link coupling 1070 for structural loading, which in turn is attached to a front link 1072a of a plurality of links 1072a-1072d that form a linked rack 1074. Linked rack 1074 is flexible yet has distal links that form a straight rigid rack assembly that may transfer a significant firing force through the firing rod 1010 in the shaft 6, yet readily retract into the pistol grip 26 to minimize the longitudinal length of the handle 6. It should be appreciated that the combination tension/compression spring 1062 increases the amount of firing travel available while essentially reducing the minimum length by half over a single spring.

The firing trigger 20 pivots about a firing trigger pin 96 that is connected to the handle pieces 59, 60. An upper portion 228 of the firing trigger 20 moves distally about the firing trigger pin 96 as the firing trigger 20 is depressed towards pistol grip 26, stretching a proximally placed firing trigger tension spring 222 proximally connected between the upper portion 228 of the firing trigger 20 and the pieces 59, 60. The upper portion 228 of the firing trigger 20 engages the linked rack 1074 during each firing trigger depression by a traction biasing mechanism 1078 that also disengages when the firing trigger 20 is released. Firing trigger tension spring 222 urges the firing trigger 20 distally when released and disengages the traction biasing mechanism 1078.

As the linked transmission firing mechanism 1040 actuates, an idler gear 1080 is rotated clockwise (as viewed from the left side) by engagement with a toothed upper surface 1082 of the linked rack 1074. This rotation is coupled to an indicator gear 1084, which thus rotates counterclockwise in response to the idler gear 1080. Both the idler gear 1080 and indicator gear 1084 are rotatably connected to the pieces 59, 60 of the handle 6. The gear relationship between the linked rack 1074, idler gear 1080 and indicator gear 1084 may be advantageously selected so that the toothed upper surface 1082 has tooth dimensions that are suitably strong and that the indicator gear 1084 makes no more than one revolution during the full firing travel of the linked transmission firing mechanism 1060.

As described in greater detail below, the indicator gear 1084 performs at least four functions. First, when the linked rack 1074 is fully retracted and both triggers 18, 20 are open as shown in FIG. 42, an opening 1086 in a circular ridge 1088 on the left side of the indicator gear 1084 is presented to an upper surface 1090 of the locking arm 1048. Locking arm 1048 is biased into the opening 1086 by contact with the closure trigger 18, which in turn is urged to the open position by a closure tension spring 1092. Closure trigger tension spring 1092 is connected proximally to the upper portion 1094 of the closure trigger 18 and the handle pieces 59, 60, and thus has energy stored during closing of the closure trigger 18 that urges the closure trigger 18 distally to its unclosed position.

A second function of the indicator gear 1084 is that it is connected to the indicating retraction knob 1096 externally disposed on the handle 6. Thus, the indicator gear 1084 communicates the relative position of the firing mechanism 1060 to the indicating retraction knob 1096 so that the surgeon has a visual indication of how many strokes of the firing trigger 20 are required to complete firing.

A third function of the indicator gear 1084 is to longitudinally and angularly move an anti-backup release lever 1098 of an anti-backup mechanism (one-way clutch mechanism) 1097 as the surgical stapling and severing instrument 10 is operated. During the firing strokes, proximal movement of anti-backup release lever 1098 by indicator gear 1084 activates the anti-backup mechanism 1097 that allows distal movement of firing bar 1010 and prevents proximal motion of firing bar 1010. This movement also extends the anti-backup release button 1100 from the proximal end of the handle pieces 59, 60 for the operator to actuate should the need arise for the linked transmission firing mechanism 1060 to be retracted during the firing strokes. After completion of the firing strokes, the indicator gear 1084 reverses direction of rotation as the firing mechanism 1060 retracts. The reversed rotation deactivates the anti-backup mechanism 1097, withdraws the anti-backup release button 1100 into the handle 6, and rotates the anti-backup release lever 1098 laterally to the right to allow continued reverse rotation of the indicator gear 1084.

A fourth function of the indicator gear 1084 is to receive a manual rotation from the indicating retraction knob 1096 (clockwise in the depiction of FIG. 42) to retract the firing mechanism 1060 with anti-backup mechanism 1097 unlocked, thereby overcoming any binding in the firing mechanism 1060 that is not readily overcome by the combination tension/compression spring 1062. This manual retraction assistance may be employed after a partial firing of the firing mechanism 1060 that would otherwise be prevented by the anti-backup mechanism 1097 that withdraws the anti-backup release button 1100 so that the latter may not laterally move the anti-backup release lever 1098.

Continuing with FIGS. 42-43, anti-backup mechanism 1097 consists of the operator accessible anti-backup release lever 1098 operably coupled at the proximal end to the anti-backup release button 1100 and at the distal end to an anti-backup yoke 1102. In particular, a distal end 1099 of the anti-backup release lever 1098 is engaged to the anti-backup yoke 1102 by an anti-backup yoke pin 1104. The anti-backup yoke 1102 moves longitudinally to impart a rotation to an anti-backup cam slot tube 1106 that is longitudinally constrained by the handle pieces 59, 90 and that encompasses the firing rod 1010 distally to the connection of the firing rod 1010 to the link coupling 1070 of the linked rack 1074. The anti-backup yoke 1102 communicates the longitudinal movement from the anti-backup release lever 1098 via a cam slot tube pin 1108 to the anti-backup cam slot tube 1106. That is, longitudinal movement of cam slot tube pin 1108 in an angled slot in the anti-backup cam slot tube 1106 rotates the anti-backup cam slot tube 1106.

Trapped between a proximal end of the frame 1016 and the anti-backup cam slot tube 1106 respectively are an anti-backup compression spring 1110, an anti-backup plate 1112, and an anti-backup cam tube 1114. As depicted, proximal movement of the firing rod 1010 causes the anti-backup plate 1112 to pivot top to the rear, presenting an increased frictional contact to the firing rod 1010 that resists further proximal movement of the firing rod 1010.

This anti-backup plate 1112 pivots in a manner similar to that of a screen door lock that holds open a screen door when the anti-backup cam slot tube 1106 is closely spaced to the anti-backup cam tube 1114. Specifically, the anti-backup compression spring 1110 is able to act upon a top surface of the plate 1112 to tip the anti-backup plate 1112 to its locked position. Rotation of the anti-backup cam slot tube 1106 causes a distal camming movement of the anti-backup cam tube 1114 thereby forcing the top of the anti-backup plate 1112 distally, overcoming the force from the anti-backup compression spring 1110, thus positioning the anti-backup plate 1112 in an untipped (perpendicular), unlocked position that allows proximal retraction of the firing rod 1010.

With particular reference to FIG. 43, the traction biasing mechanism 1078 is depicted as being composed of a pawl 1116 that has a distally projecting narrow tip 1118 and a rightwardly projecting lateral pin 1120 at its proximal end that is rotatably inserted through a hole 1076 in the upper portion 230 of the firing trigger 20. On the right side of the firing trigger 20 the lateral pin 1120 receives a biasing member, depicted as biasing wheel 1122. As the firing trigger 20 translates fore and aft, the biasing wheel 1122 traverses an arc proximate to the right half piece 59 of the handle 6, overrunning at its distal portion of travel a biasing ramp 1124 integrally formed in the right half piece 59. The biasing wheel 1122 may advantageously be formed from a resilient, frictional material that induces a counterclockwise rotation (when viewed from the left) into the lateral pin 1120 of the pawl 1116, thus traction biasing the distally projecting narrow tip 1118 downward into a ramped central track 1075 of the nearest link 1072a-d to engage the linked rack 1074.

As the firing trigger 20 is released, the biasing wheel 1122 thus tractionally biases the pawl 1116 in the opposite direction, raising the narrow tip 1118 from the ramped central track 1075 of the linked rack 1074. To ensure disengagement of the tip 1118 under high load conditions and at nearly full distal travel of the pawl 1116, the right side of the pawl 1116 ramps up onto a proximally and upwardly facing beveled surface 1126 on the right side of the closure yoke 250 to disengage the narrow tip 1118 from the ramped central track 1075. If the firing trigger 20 is released at any point other than full travel, the biasing wheel 1122 is used to lift the narrow tip 1118 from the ramped central track 1075. Whereas a biasing wheel 1122 is depicted, it should be appreciated that the shape of the biasing member or wheel 1122 is illustrative and may be varied to accommodate a variety of shapes that use friction or traction to engage or disengage the firing of the end effector 12.

Figure 44:
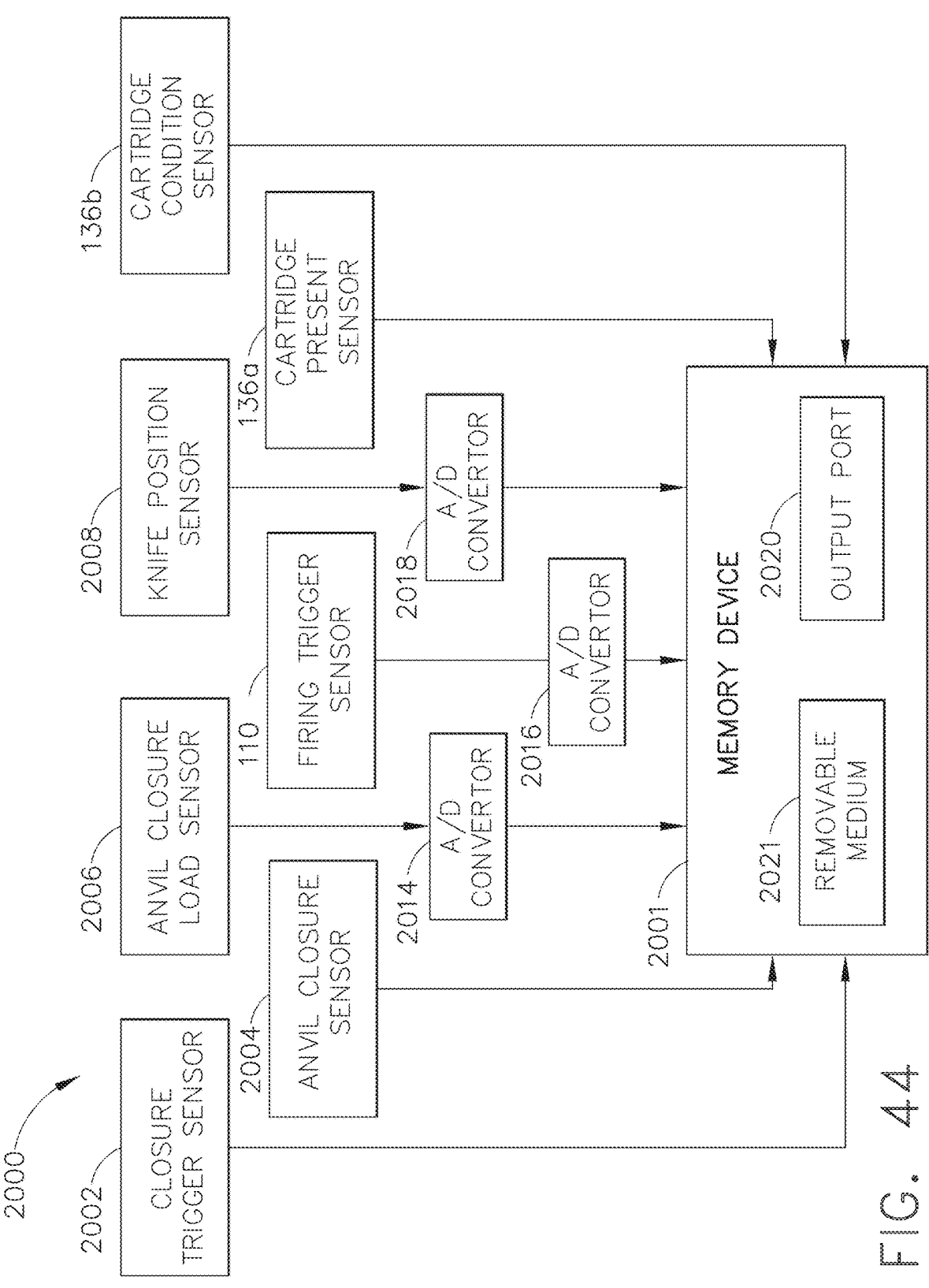
FIG. 44 illustrates a block diagram of a recording system for recording various conditions of the instrument according to various embodiments of the present invention.

Various embodiments of the surgical instrument 10 have the capability to record instrument conditions at one or more times during use. FIG. 44 shows a block diagram of a system 2000 for recording conditions of the instrument 10. It will be appreciated that the system 2000 may be implemented in embodiments of the instrument 10 having motorized or motor-assisted firing, for example, as described above with reference to FIGS. 1-40, as well as embodiments of the instrument 10 having mechanically actuated firing, for example, as described above with reference to FIGS. 41-43.

The system 2000 may include various sensors 2002, 2004, 2006, 2008, 136a, 136b for sensing instrument conditions. The sensors may be positioned, for example, on or within the instrument 10. In various embodiments, the sensors may be dedicated sensors that provide output only for the system 2000, or may be dual-use sensors that perform other functions within the instrument 10. For example, sensors 110, 130, 142 described above may be configured to also provide output to the system 2000.

Directly or indirectly, each sensor provides a signal to the memory device 2001, which records the signals as described in more detail below. The memory device 2001 may be any kind of device capable of storing or recording sensor signals. For example, the memory device 2001 may include a microprocessor, an Electrically Erasable Programmable Read Only Memory (EEPROM), or any other suitable storage device. The memory device 2001 may record the signals provided by the sensors in any suitable way. For example, in one embodiment, the memory device 2001 may record the signal from a particular sensor when that signal changes states. In another embodiment, the memory device 2001 may record a state of the system 2000, e.g., the signals from all of the sensors included in the system 2000, when the signal from any sensor changes states. This may provide a snap-shot of the state of the instrument 10. In various embodiments, the memory device 2001 and/or sensors may be implemented to include 1-WIRE bus products available from DALLAS SEMICONDUCTOR such as, for example, a 1-WIRE EEPROM.

In various embodiments, the memory device 2001 is externally accessible, allowing an outside device, such as a computer, to access the instrument conditions recorded by the memory device 2001. For example, the memory device 2001 may include a data port 2020. The data port 2020 may provide the stored instrument conditions according to any wired or wireless communication protocol in, for example, serial or parallel format. The memory device 2001 may also include a removable medium 2021 in addition to or instead of the output port 2020. The removable medium 2021 may be any kind of suitable data storage device that can be removed from the instrument 10. For example, the removable medium 2021 may include any suitable kind of flash memory, such as a Personal Computer Memory Card International Association (PCMCIA) card, a COMPACTFLASH card, a MULTIMEDIA card, a FLASHMEDIA card, etc. The removable medium 2021 may also include any suitable kind of disk-based storage including, for example, a portable hard drive, a compact disk (CD), a digital video disk (DVD), etc.

Figure 45:
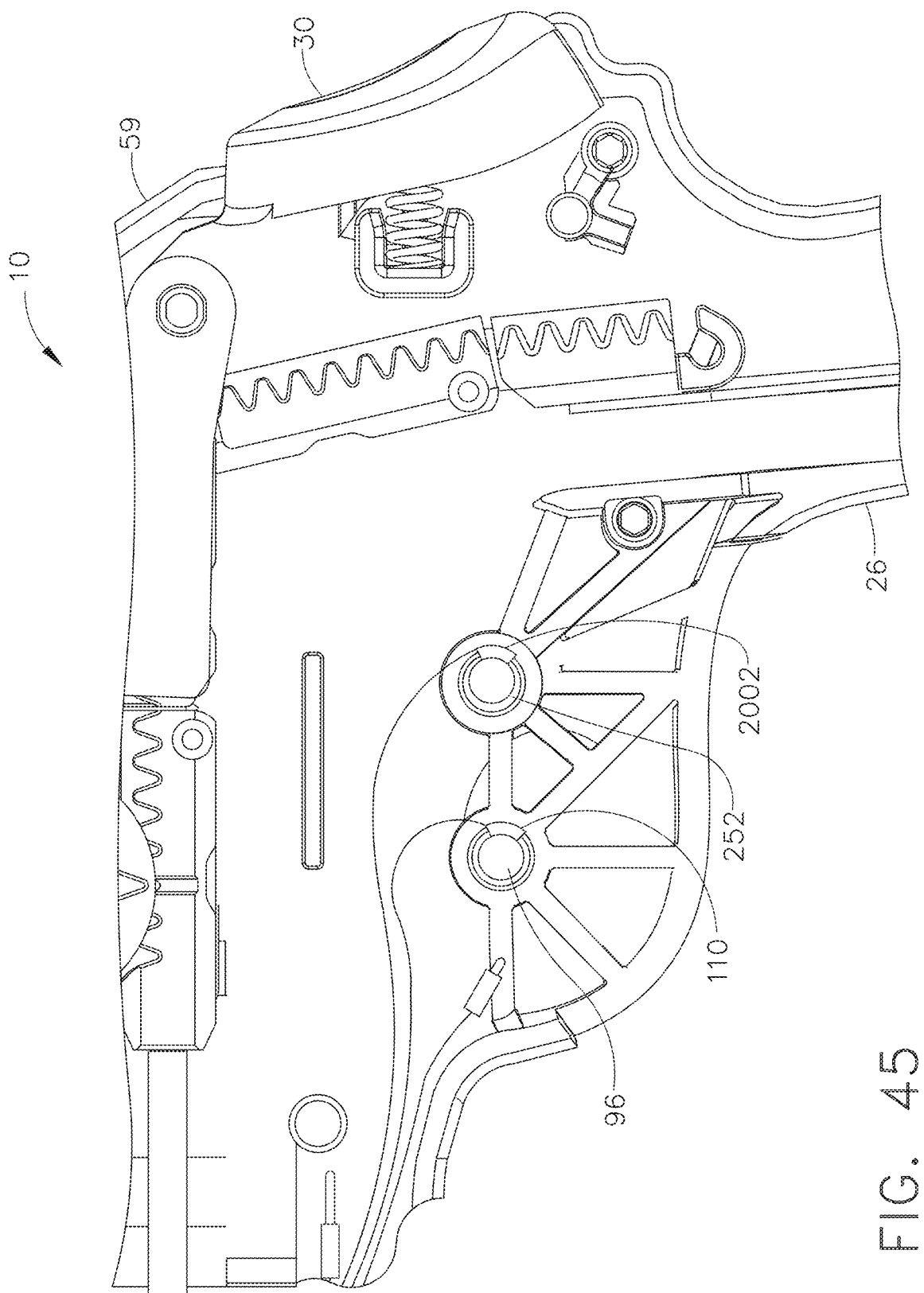
FIGS. 45-46 illustrate cut away side views of a handle of the instrument showing various sensors according to various embodiments of the present invention.
Figure 46:
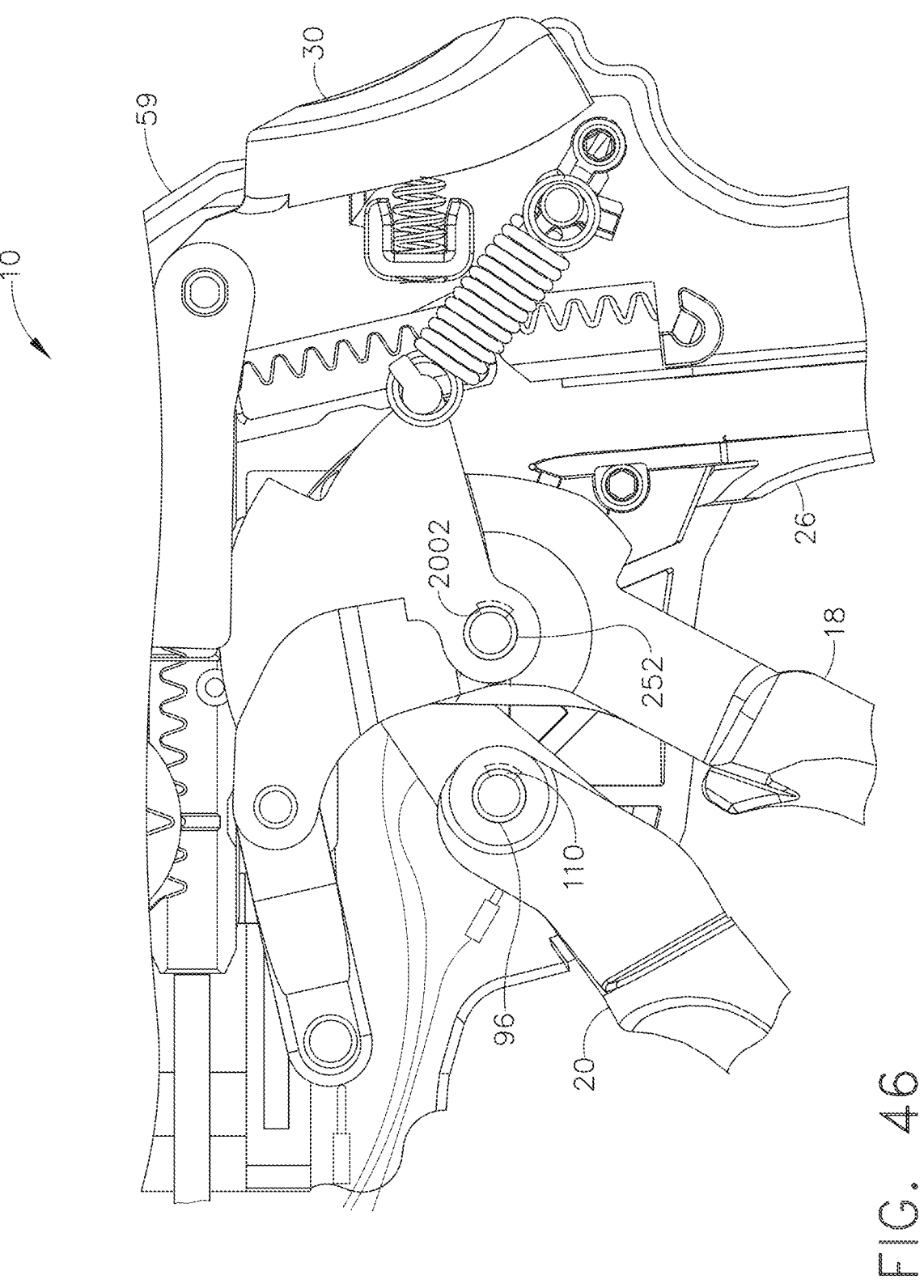

The closure trigger sensor 2002 senses a condition of the closure trigger 18. FIGS. 45 and 46 show an exemplary embodiment of the closure trigger sensor 2002. In FIGS. 45 and 46, the closure trigger sensor 2002 is positioned between the closure trigger 18 and closure pivot pin 252. It will be appreciated that pulling the closure trigger 18 toward the pistol grip 26 causes the closure trigger 18 to exert a force on the closure pivot pin 252. The sensor 2002 may be sensitive to this force, and generate a signal in response thereto, for example, as described above with respect to sensor 110 and FIGS. 10A and 10B. In various embodiments, the closure trigger sensor 2002 may be a digital sensor that indicates only whether the closure trigger 18 is actuated or not actuated. In other various embodiments, the closure trigger sensor 2002 may be an analog sensor that indicates the force exerted on the closure trigger 18 and/or the position of the closure trigger 18. If the closure trigger sensor 2002 is an analog sensor, an analog-to-digital converter may be logically positioned between the sensor 2002 and the memory device 2001. Also, it will be appreciated that the closure trigger sensor 2002 may take any suitable form and be placed at any suitable location that allows sensing of the condition of the closure trigger.

Figures 47, 48:
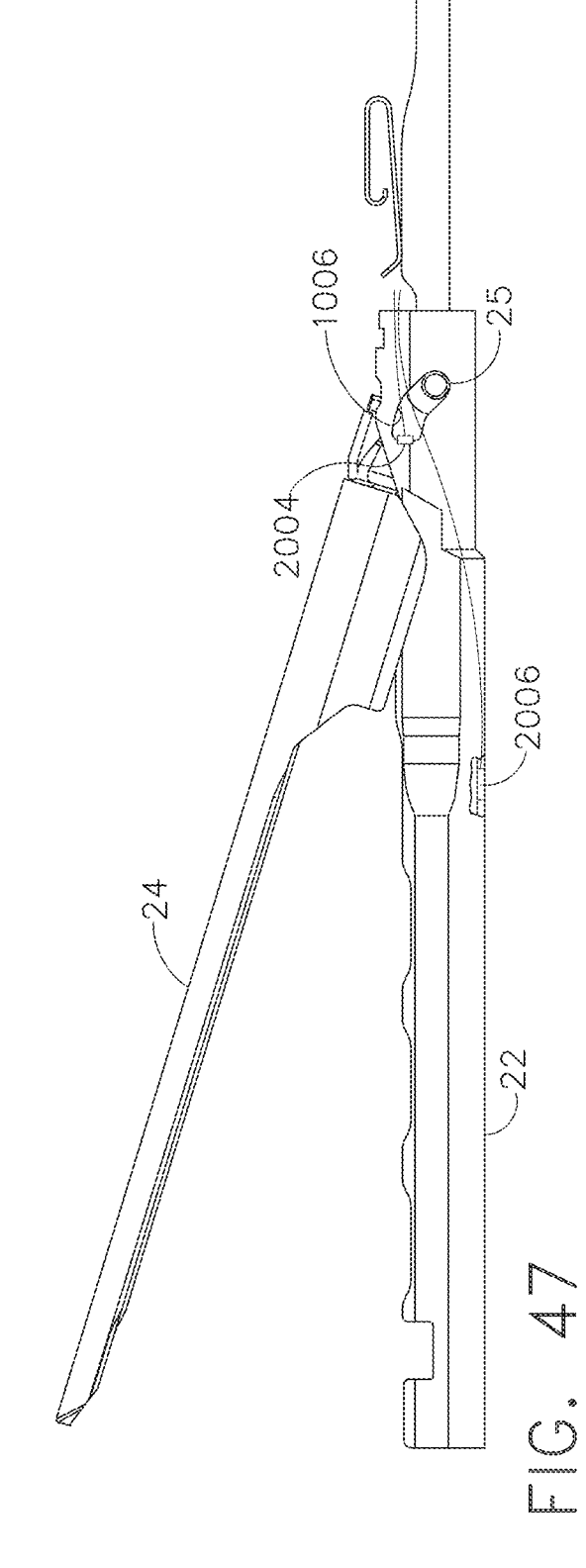
FIG. 47 illustrates the end effector of the instrument showing various sensors according to various embodiments of the present invention.
FIG. 48 illustrates a firing bar of the instrument including a sensor according to various embodiments of the present invention.
Figure 49:
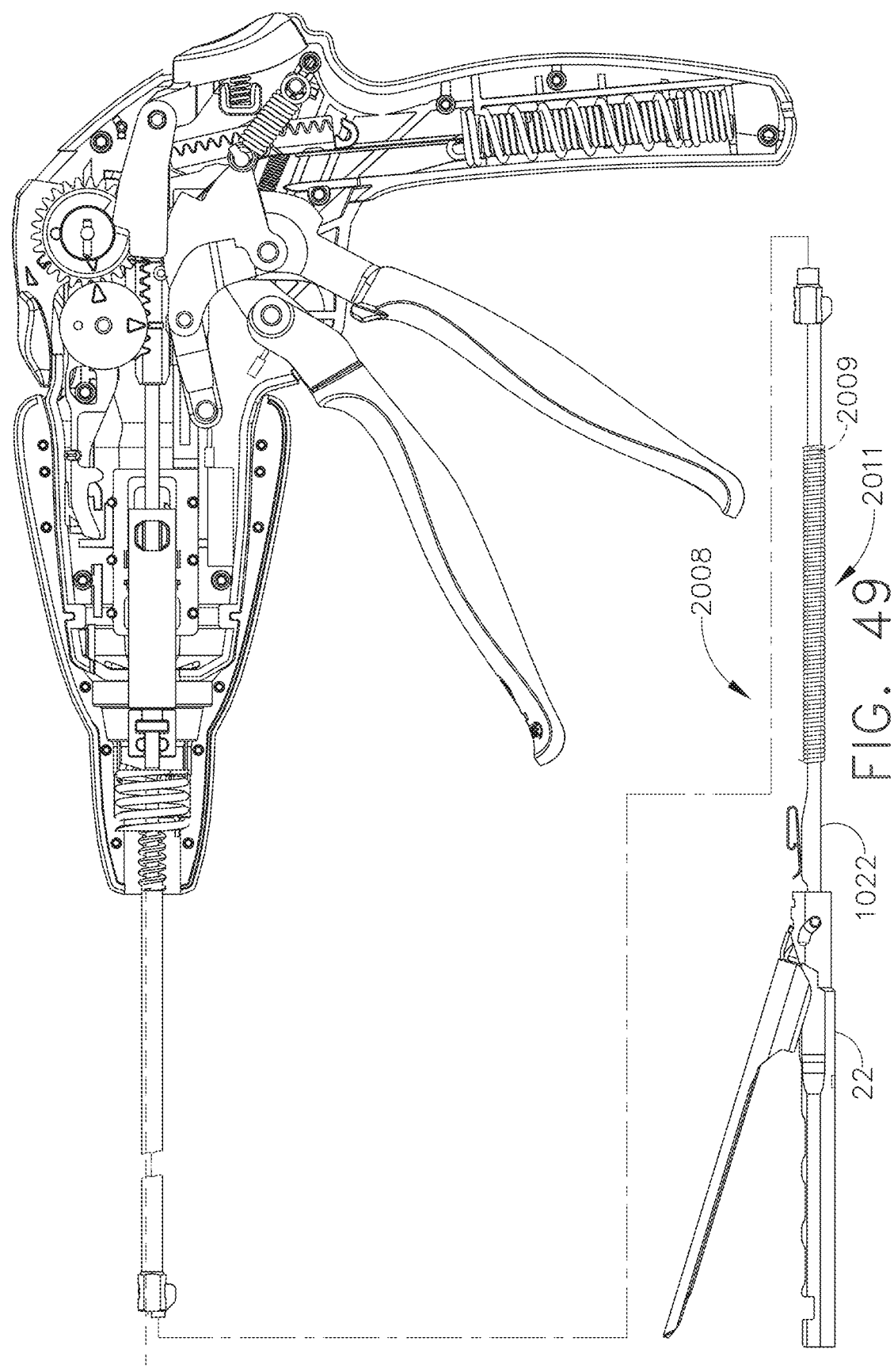
FIG. 49 illustrates a side view of the handle, end effector, and firing bar of the instrument showing a sensor according to various embodiments of the present invention.

The anvil closure sensor 2004 may sense whether the anvil 24 is closed. FIG. 47 shows an exemplary anvil closure sensor 2004. The sensor 2004 is positioned next to, or within the kidney shaped openings 1006 of the staple channel 22 as shown. As the anvil 24 is closed, anvil pivot pins 25 slides through the kidney shaped openings 1006 and into contact with the sensor 2004, causing the sensor 2004 to generate a signal indicating that the anvil 24 is closed. The sensor 2004 may be any suitable kind of digital or analog sensor including a proximity sensor, etc. It will be appreciated that when the anvil closure sensor 2004 is an analog sensor, an analog-to-digital converter may be included logically between the sensor 2004 and the memory device 2001.

Anvil closure load sensor 2006 is shown placed on an inside bottom surface of the staple channel 22. In use, the sensor 2006 may be in contact with a bottom side of the staple cartridge 34 (not shown in FIG. 46). As the anvil 24 is closed, it exerts a force on the staple cartridge 34 which is transferred to the sensor 2006. In response, the sensor 2006 generates a signal. The signal may be an analog signal proportional to the force exerted on the sensor 2006 by the staple cartridge 34 and due to the closing of the anvil 24. Referring the FIG. 44, the analog signal may be provided to an analog-to-digital converter 2014, which converts the analog signal to a digital signal before providing it to the memory device 2001. It will be appreciated that embodiments where the sensor 2006 is a digital or binary sensor may not include analog-to-digital converter 2014.

The firing trigger sensor 110 senses the position and/or state of the firing trigger 20. In motorized or motor-assisted embodiments of the instrument, the firing trigger sensor may double as the run motor sensor 110 described above. In addition, the firing trigger sensor 110 may take any of the forms described above, and may be analog or digital. FIGS. 45 and 46 show an additional embodiment of the firing trigger sensor 110. In FIGS. 45 and 46, the firing trigger sensor is mounted between firing trigger 20 and firing trigger pivot pin 96. When firing trigger 20 is pulled, it will exert a force on firing trigger pivot pin 96 that is sensed by the sensor 110. Referring to FIG. 44, In embodiments where the output of the firing trigger sensor 110 is analog, analog-to-digital converter 2016 is included logically between the firing trigger sensor 110 and the memory device 2001.

The knife position sensor 2008 senses the position of the knife 32 or cutting surface 1027 within the staple channel 22. FIGS. 47 and 48 show embodiments of a knife position sensor 2008 that are suitable for use with the mechanically actuated shaft 8 and end effector 12 shown in FIG. 41. The sensor 2008 includes a magnet 2009 coupled to the firing bar 1022 of the instrument 10. A coil 288a is positioned around the firing bar 1022, and may be installed; for example, along the longitudinal recess 1014 of the firing trough member 1012 (see FIG. 41). As the knife 32 and cutting surface 1027 are reciprocated through the staple channel 22, the firing bar 1022 and magnet 2009 may move back and forth through the coil 288a. This motion relative to the coil induces a voltage in the coil proportional to the position of the firing rod within the coil and the cutting edge 1027 within the staple channel 22. This voltage may be provided to the memory device 2001, for example, via analog-to-digital converter 2018.

In various embodiments, the knife position sensor 2008 may instead be implemented as a series of digital sensors (not shown) placed at various positions on or within the shaft 8. The digital sensors may sense a feature of the firing bar 1022 such as, for example, magnet 2009, as the feature reciprocates through the shaft 8. The position of the firing bar 1022 within the shaft 8, and by extension, the position of the knife 32 within the staple channel 22, may be approximated as the position of the last digital sensor tripped.

It will be appreciated that the knife position may also be sensed in embodiments of the instrument 10 having a rotary driven end effector 12 and shaft 8, for example, as described above, with reference to FIGS. 3-6. An encoder, such as encoder 268, may be configured to generate a signal proportional to the rotation of the helical screw shaft 36, or any other drive shaft or gear. Because the rotation of the shaft 36 and other drive shafts and gears is proportional to the movement of the knife 32 through the channel 22, the signal generated by the encoder 268 is also proportional to the movement of the knife 32. Thus, the output of the encoder 268 may be provided to the memory device 2001.

The cartridge present sensor 136a may sense the presence of the staple cartridge 34 within the staple channel 22. In motorized or motor-assisted instruments, the cartridge present sensor 136a may double as the cartridge lock-out sensor 136 described above with reference to FIG. 11. FIGS. 50A and 50B show an embodiment of the cartridge present sensor 136a. In the embodiment shown, the cartridge present sensor 136a includes two contacts, 288a and 288b. When no cartridge 34 is present, the contacts 288a, 288b form an open circuit. When a cartridge 34 is present, the cartridge tray 290 of the staple cartridge 34 contacts the contacts 288a, 288b, a closed circuit is formed. When the circuit is open, the sensor 136a may output a logic zero. When the circuit is closed, the sensor 136a may output a logic one. The output of the sensor 136a is provided to memory device 2001, as shown in FIG. 44.

The cartridge condition sensor 136b may indicate whether a cartridge 34 installed within the staple channel 22 has been fired or spent. As the knife 32 is translated through the end effector 12, it pushes the sled 33, which fires the staple cartridge. Then the knife 32 is translated back to its original position, leaving the sled 33 at the distal end of the cartridge. Without the sled 33 to guide it, the knife 32 may fall into lock-out pocket 2022. Sensor 136b may sense whether the knife 32 is present in the lock-out pocket 2022, which indirectly indicates whether the cartridge 34 has been spent. It will be appreciated that in various embodiments, sensor 136b may directly sense the present of the sled at the proximate end of the cartridge 34, thus eliminating the need for the knife 32 to fall into the lock-out pocket 2022.

FIGS. 52A and 52B depict a process flow 2200 for operating embodiments of the surgical instrument 10 configured as an endocutter and having the capability to record instrument conditions according to various embodiments. At box 2202, the anvil 24 of the instrument 10 may be closed. This causes the closure trigger sensor 2002 and or the anvil closure sensor 2006 to change state. In response, the memory device 2001 may record the state of all of the sensors in the system 2000 at box 2203. At box 2204, the instrument 10 may be inserted into a patient. When the instrument is inserted, the anvil 24 may be opened and closed at box 2206, for example, to manipulate tissue at the surgical site. Each opening and closing of the anvil 24 causes the closure trigger sensor 2002 and/or the anvil closure sensor 2004 to change state. In response, the memory device 2001 records the state of the system 2000 at box 2205.

At box 2208, tissue is clamped for cutting and stapling. If the anvil 24 is not closed at decision block 2210, continued clamping is required. If the anvil 24 is closed, then the sensors 2002, 2004 and/or 2006 may change state, prompting the memory device 2001 to record the state of the system at box 2213. This recording may include a closure pressure received from sensor 2006. At box 2212, cutting and stapling may occur. Firing trigger sensor 110 may change state as the firing trigger 20 is pulled toward the pistol grip 26. Also, as the knife 32 moves through the staple channel 22, knife position sensor 2008 will change state. In response, the memory device 2001 may record the state of the system 2000 at box 288b.

When the cutting and stapling operations are complete, the knife 32 may return to a pre-firing position. Because the cartridge 34 has now been fired, the knife 32 may fall into lock-out pocket 2022, changing the state of cartridge condition sensor 136b and triggering the memory device 2001 to record the state of the system 2000 at box 2015. The anvil 24 may then be opened to clear the tissue. This may cause one or more of the closure trigger sensor 2002, anvil closure sensor 2004 and anvil closure load sensor 2006 to change state, resulting in a recordation of the state of the system 2000 at box 2017. After the tissue is cleared, the anvil 24 may be again closed at box 2220. This causes another state change for at least sensors 2002 and 2004, which in turn causes the memory device 2001 to record the state of the system at box 2019. Then the instrument 10 may be removed from the patient at box 2222.

If the instrument 10 is to be used again during the same procedure, the anvil may be opened at box 2224, triggering another recordation of the system state at box 2223. The spent cartridge 34 may be removed from the end effector 12 at box 2226. This causes cartridge present sensor 136a to change state and cause a recordation of the system state at box 2225. Another cartridge 34 may be inserted at box 2228. This causes a state change in the cartridge present sensor 136a and a recordation of the system state at box 2227. If the other cartridge 34 is a new cartridge, indicated at decision block 2230, its insertion may also cause a state change to cartridge condition sensor 136b. In that case, the system state may be recorded at box 2231.

FIG. 53 shows an exemplary memory map 2300 from the memory device 2001 according to various embodiments. The memory map 2300 includes a series of columns 2302, 2304, 2306, 2308, 2310, 2312, 2314, 2316 and rows (not labeled). Column 2302 shows an event number for each of the rows. The other columns represent the output of one sensor of the system 2000. All of the sensor readings recorded at a given time may be recorded in the same row under the same event number. Hence, each row represents an instance where one or more of the signals from the sensors of the system 2000 are recorded.

Column 2304 lists the closure load recorded at each event. This may reflect the output of anvil closure load sensor 2006. Column 2306 lists the firing stroke position. This may be derived from the knife position sensor 2008. For example, the total travel of the knife 32 may be divided into partitions. The number listed in column 2306 may represent the partition where the knife 32 is currently present. The firing load is listed in column 2308. This may be derived from the firing trigger sensor 110. The knife position is listed at column 2310. The knife position may be derived from the knife position sensor 2008 similar to the firing stroke. Whether the anvil 24 is open or closed may be listed at column 2312. This value may be derived from the output of the anvil closure sensor 2004 and/or the anvil closure load sensor 2006. Whether the sled 33 is present, or whether the cartridge 34 is spent, may be indicated at column 2314. This value may be derived from the cartridge condition sensor 136b. Finally, whether the cartridge 34 is present may be indicated a column 2316. This value may be derived from cartridge present sensor 136a. It will be appreciated that various other values may be stored at memory device 2001 including, for example, the end and beginning of firing strokes, for example, as measured by sensors 130, 142.

As indicated above, there are several steps within the function of a stapler that generally must be accomplished in an established order. For example, once the closure trigger is clamped, the firing cycle may be actuated. After the knife has been fully deployed, then retraction of the system is the next sequential step. With the inclusion of a power source other than the user (i.e. batteries or pneumatics) the ability to reduce user initiated steps (and therefore device complexity) the system itself, as was discussed above, can begin to accomplish these steps itself.

It may be desirable, however, for the user to intuitively be able to delay, slow or stop these otherwise "automatic" actuations. For example, the same actuation button that would allow for firing initiation in a tactile feedback device like the devices disclosed in U.S. patent application Ser. No. 11/344,035, now U.S. Pat. No. 7,422,139, the disclosure of which is herein incorporated by reference in its entirety could be used to slow or stop an automatic return system by the user depressing the button during the retraction.

For example, FIGS. 54 and 55 illustrate another embodiment of the present invention including an embodiment of an instrument 3010 wherein a retraction trigger 3121 is supported on the firing trigger 3020 (similar to firing trigger 20 described herein above) for travel therewith. More specifically, the retraction trigger 3121 is pivotally supported on firing trigger pin 96 and protrudes through a slot (not shown) in the firing trigger 3020. A spring 3125 is attached between a coupling portion 3123 of the firing trigger 3020 and a mounting portion 3127 of the retraction trigger 3121 to bias the retraction trigger 3121 into an unactuated position. A second, normally-closed, retraction switch 3131 is mounted within the handle and is oriented such that, as the firing trigger 3020 is moved between a fully actuated position to a fully unactuated position, an activation portion 3129 of the retraction trigger 3121 does not activate the retraction switch 3131. However, the mounting portion 3127 and activation portion 3129 of the retraction trigger 3121 are so configured such that the activation portion 3129 may be brought into activation contact with the retraction switch 3131 by depressing the retraction trigger 3121 towards the firing trigger 3020 regardless of where the firing trigger 3020 is located during the retraction process.

The embodiment shown in FIGS. 54-55 may also include various components that operate in a manner similar that described herein above, for example, with respect to FIG. 10. For example, reverse motor or end-of-stroke sensor 3130 and stop motor or beginning-of-stroke sensor 3142 may operate in a manner similar to the respective sensors 130, 142 described herein above. Mechanical components, 3122,

3078, 3072, 3070, 3068, 3074, 3090 may operate in a manner similar to the respective mechanical components 122, 78, 72, 68, 74, 90. Motor 3065 may operate in a manner similar to the motor 65. Also, the main drive shaft 3048 may operate in a manner similar to the main drive shaft 48 described herein above. For example, the main drive shaft 3048 may cause actuation of an end effector 12, including for example, actuation of a knife 32 and sled 33.

As was discussed above, when the end effector 12 reaches the end of its stroke, the end of stroke switch 3130 will be activated. As shown in the example of FIG. 55, the retraction switch 3131 is in series with the end-of-stroke switch 3130. Because the retraction switch 3131 is normally closed, the inductor 3134 of the relay 3132 will be energized when both switches 3130, 3131 are closed. This causes the relay 3132 to assume its energized state, which causes current to bypass the cartridge lockout sensor 3136 and variable resistor 3110. Current flows to the double pole, double throw relay 3140 and to the motor 3065, but in a manner, via the relay 3140, that causes the motor 3065 to reverse its rotational direction. Because the beginning-of-stroke switch 3142 is closed, current will flow back to the relay 3132 to keep it closed until the switch 3142 opens. When the knife 32 is fully retracted, the beginning-of-stroke switch 3142 is opened, thereby removing power from the motor 3065. If, however, the user wants to slow down the retraction process, the user may depress the retraction trigger 3121 to activate the variable resistance portion 3133 of the retraction switch 3131. When the retraction trigger 3121 is not depressed, the resistance of the variable resistance portion 3133 is a minimum. When the trigger 3121 is depressed, the resistance of the variable resistance portion 3133 increases in proportion to the depressing force of the retraction trigger 3121 to reduce the current to the motor 3065. Further depression of the retraction trigger 3121 will slow the retraction process until the normally closed contact 3135 portion of the retraction switch 3131 opens and stops the current flow to the motor 3065. In various embodiments, once the user releases the retraction trigger 3121, the spring 3125 will move the retraction trigger 3121 to an unactuated position and the contact portion 3135 of switch 3131 will return to the normally closed position and thereby permit current to flow again to the motor 3065 to complete the retraction process.

The unique and novel features of the retraction switch and retraction trigger arrangements described above may also be employed in connection with the various embodiments disclosed in U.S. Patent Application Publication No. US 2010/0076474 A1, now U.S. Pat. Nos. 8,210,411 and 7,422, 139 which have both been herein incorporated by reference in their respective entireties. For example, FIG. 56 shows another embodiment of a current control circuit of the present invention. When (i) the run motor (or fire) switch 3110 is closed (it is shown in an open state in FIG. 56), (ii) the safety switch 3240 is closed (it is shown open in FIG. 56) indicating that the device safety is set, and (iii) the normally-closed lockout switch 3242 is opened indicating that the instrument is not in a lock-out condition, current flows through the safety switch 3240, through the lockout indicator 3244 (which may be a LED as shown in FIG. 56) to the motor 3065. When the end of the cutting stroke is reached, the end-of-stroke or direction switch 3130 is switched, reversing the direction of the motor 3065 (with the fire switch 3110 also having been released). In this state, current also flows through a reverse direction indicator 3246, such as an LED, providing a visual indication that the motor direction has been reversed.

As shown in FIG. 56, the circuit may also comprise a manual return switch 3248. The operator may manually actuate this switch if the cutting instrument 32 has only been partially fired. Switching the manual return switch 3248 causes the motor 3065 to reverse rotate, causing the cutting instrument 32 to return to its original or home position. If, the user desires to slow down or stop the retraction process, the user depresses the retraction trigger 3121 to activate the variable resistance portion 3133 of the retraction switch 3131. When the trigger 3121 is depressed, the resistance increases in proportion to the depressing force to reduce the current to the motor 3065. Further depression of the retraction trigger 3121 will slow the retraction process until the normally closed contact 3135 portion of the retraction switch 3131 opens and stops the current flow to the motor 3065. In various embodiments, once the user releases the retraction trigger 3121, the spring 3125 will move the retraction trigger 3121 to an unactuated position and the contact portion 3135 of switch 3131 will return to the normally closed position and thereby permit current to flow again to the motor 3065 to complete the retraction process.

Figure 57:
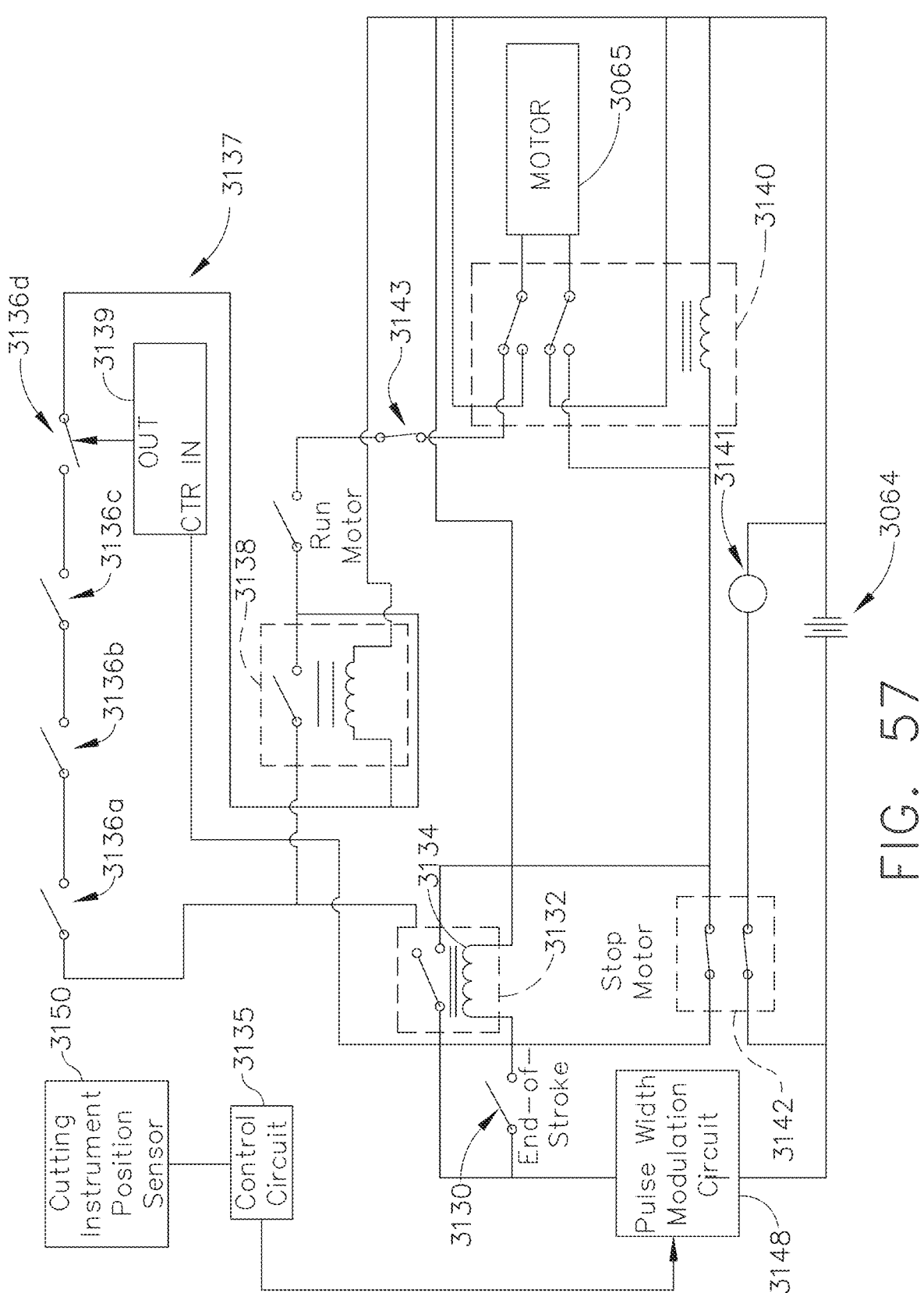

Additional configurations for motorized surgical instruments are disclosed in published U.S. Patent Application Publication No. US 2010/0076474 A1, entitled MOTOR-DRIVEN SURGICAL CUTTING INSTRUMENT, now U.S. Pat. No. 8,210,411 which is incorporated herein by reference in its entirety. For example, FIG. 57 is a schematic diagram of another current control circuit according to various embodiments of the present invention. In various embodiments, the motor control circuit may include one of more integrated circuits (ICs), such as, for example, a processor, memory, microcontroller, time circuits, etc. In other embodiments, the motor control circuit may not comprise any ICs. Such a non-IC current control circuit may be advantageous because it is often difficult, complicated, and expensive to sterilize a surgical instrument including ICs.

When an operator initially applies an actuation motion to the firing trigger 3020 after locking the closure trigger 18, the run motor switch 3110 is activated (or closed), allowing current to flow therethrough. If the normally open reverse motor sensor switch 3130 is open (meaning the end of the end effector stroke has not been reached), current will flow to a single pole, double throw relay 3132. When the reverse motor sensor switch 3130 is not closed, a coil 3134 of the relay 3132 will not be energized, so the relay 3132 will be in its de-energized state.

Figure 57A:
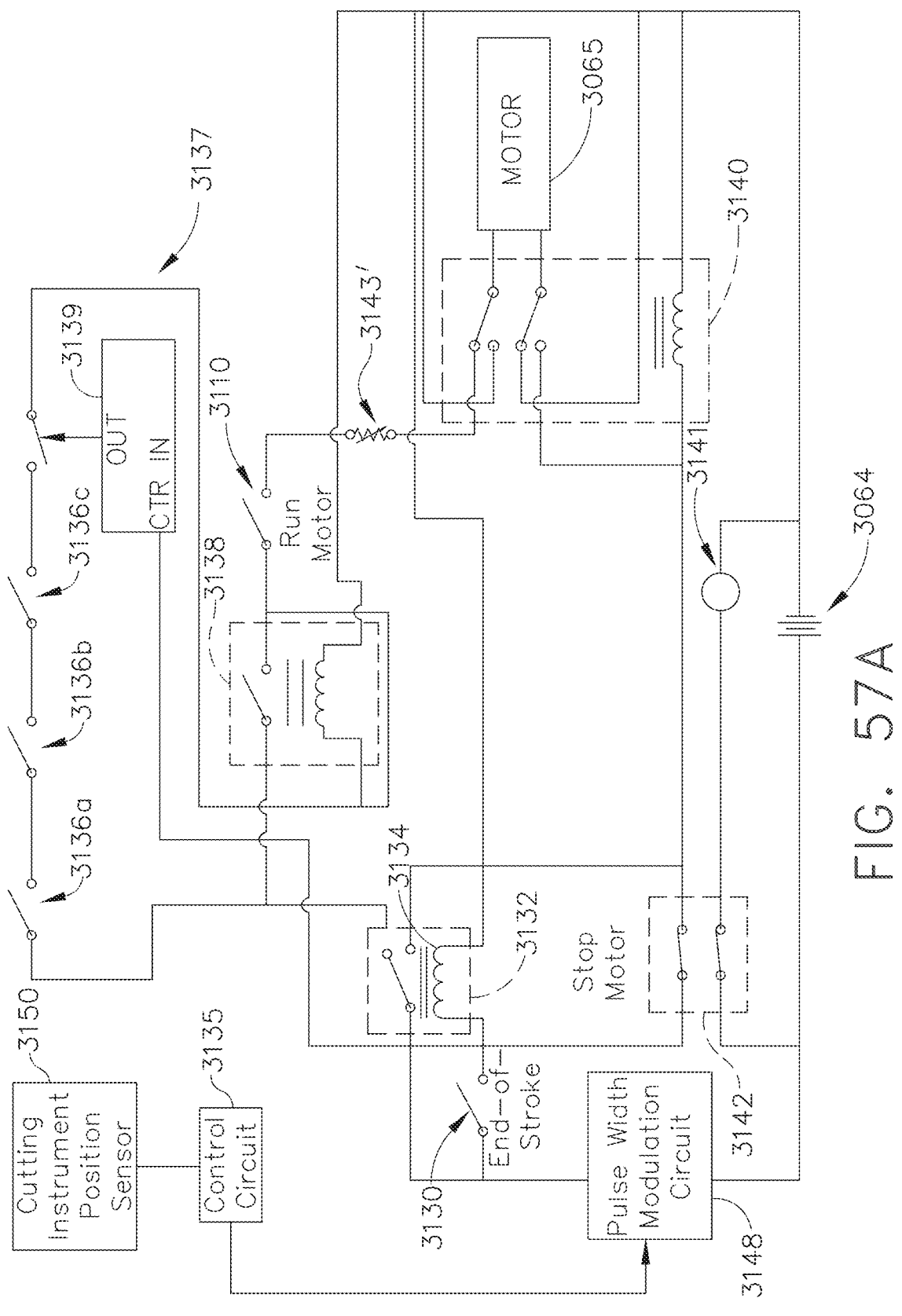
Figure 57B:
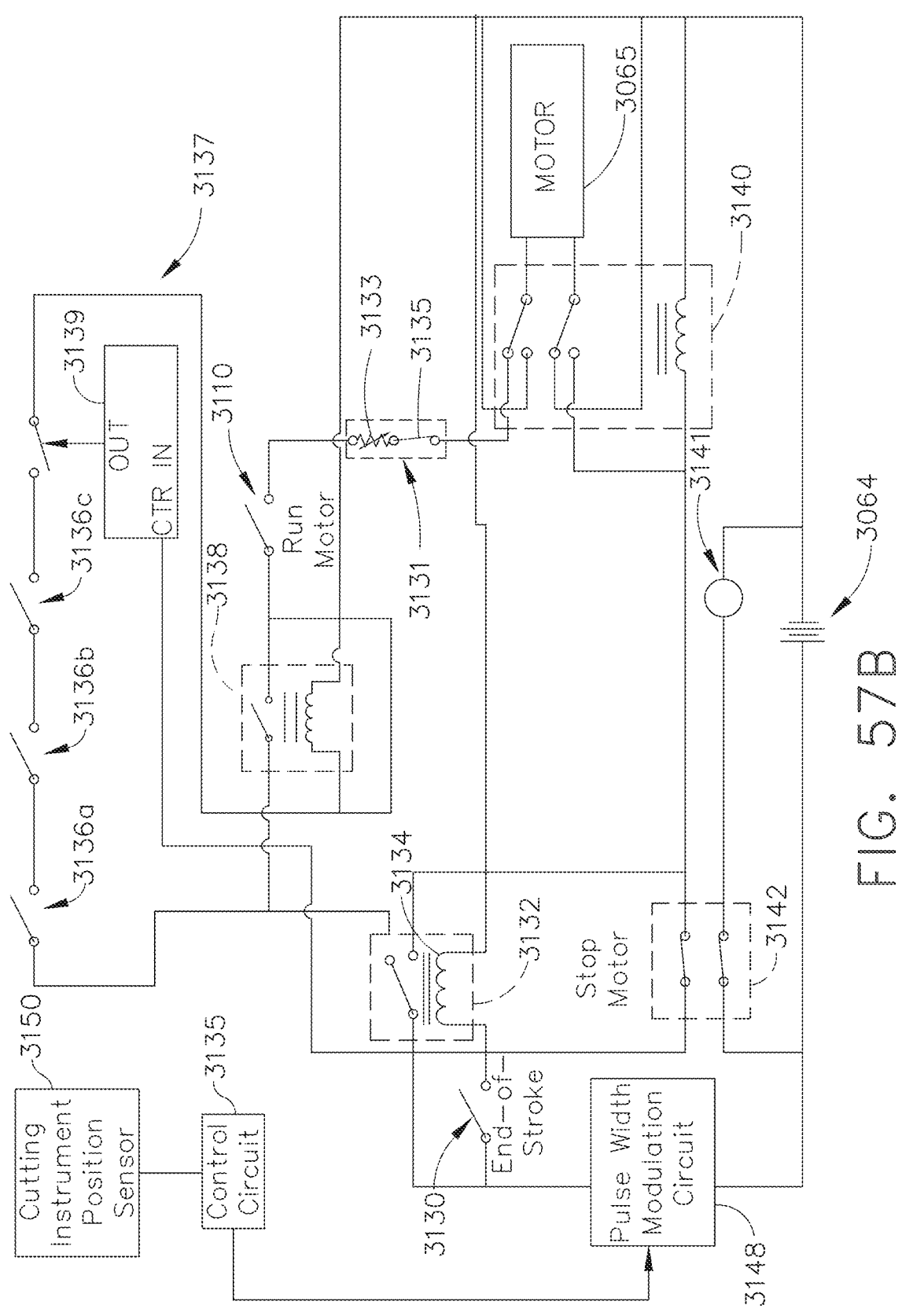
Figure 57C:
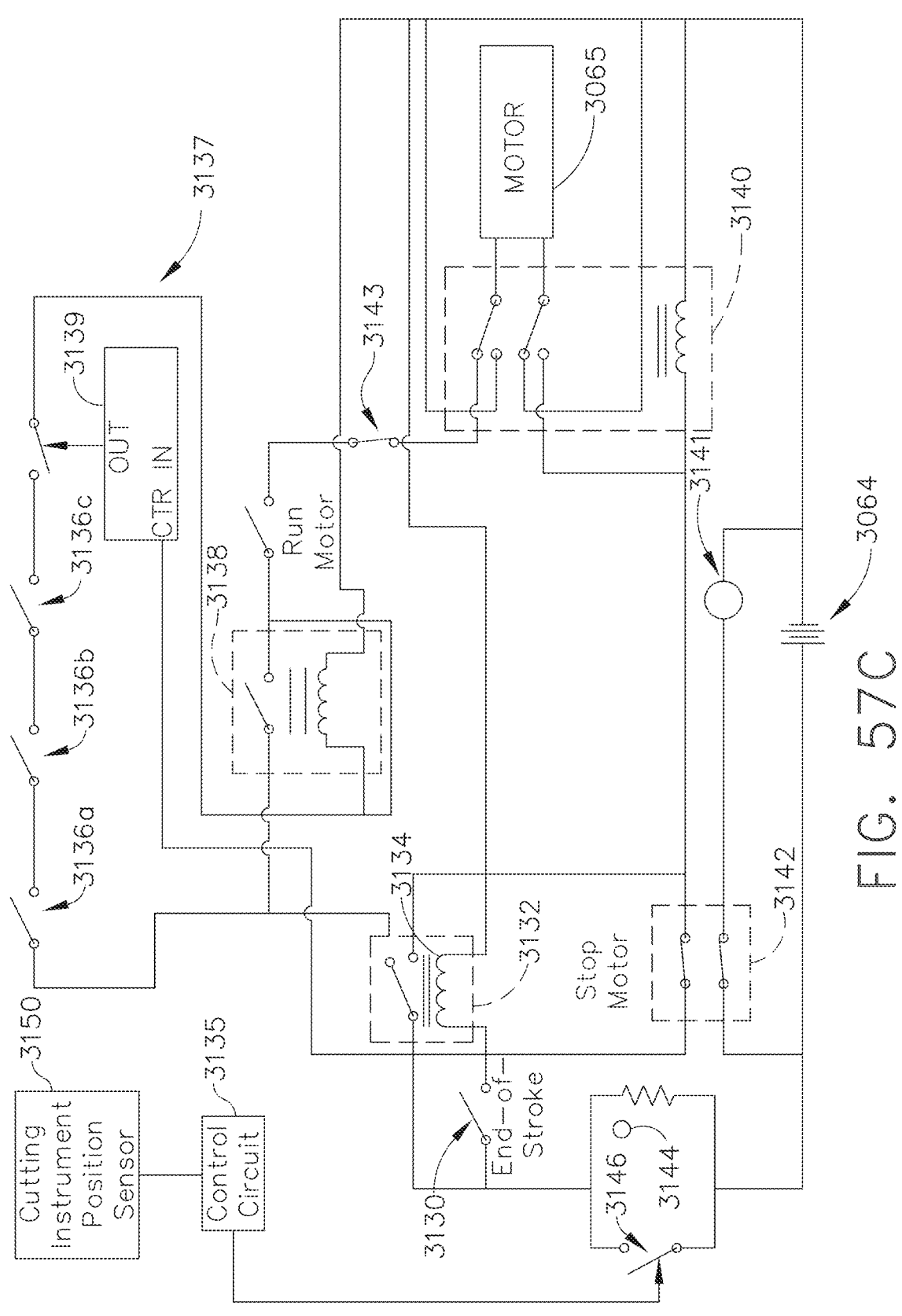

As shown in FIG. 57C, the circuit may also include a resistive element 3144 and a switch 3146 connected in parallel, with the paralleled elements connected in series with the relay 3132. The resistive element 3144 and the switch 3146 are also connected to the power source 3064. The switch 3146 may be controlled by a control circuit 3135 that is responsive to the cutting instrument position sensor 3150. According to various embodiments, the control circuit 3135 may open the switch 3146 when the cutting instrument 32 is (i) very near to the beginning of its stroke and (ii) very near to the end of its stroke. For example, the control circuit may open the switch when the cutting instrument 32 is (i) 0.001 inches from the beginning point of its stroke and (ii) 0.001 inches from the end of its stroke, as determined by the cutting instrument position sensor 3150. With the switch 3142 open, current flows through the resistive element 3144, and then through the relay 3132, the relay 3138, the run motor sensor switch 3110, to the motor 3065. Current flowing through the resistive element 3144 reduces the magnitude of the current delivered to the motor 3065, thereby reducing the power delivered by the motor 3065.

Thus, when the cutting instrument 32 is (i) very near to the beginning of its stroke or (ii) very near to the end of its stroke, the power delivered by the motor 3065 is reduced. Conversely, once the cutting instrument 32 moves sufficiently far from its beginning point or end of stroke point, the control circuit 3135 may close the switch 3146, thereby shorting the resistive element 3144, thereby increasing the current to the motor 3065, thereby increasing the power delivered by the motor.

Alternatively, the resistive element 3144 and switch 3146 may be replaced by and/or supplemented with a pulse width modulation circuit 3148, as illustrated in FIGS. 57, 57A, 57B. The pulse width modulation circuit 3148, as shown, may be connected in series between the power source 3064 and the motor 3065. The pulse width modulation circuit 3148 may receive signals from the control circuit 3135 causing the circuit 3148 to switch between an open and a closed circuit. The duty cycle or pulse width of the resulting signal may control the average current, and therefore the power, provided to the motor 3065. When the cutting instrument 32 is near the beginning or the end of its stroke, the pulse wide modulation circuit 3148 may decrease the duty cycle or pulse width of the current provided to the motor 3065, thus reducing the delivered power.

According to various embodiments, the current control circuit further includes lockout sensor switches 3136a-d collectively defining an interlock circuit 3137 through which current from the relay 3132, when de-energized, passes in order for electrical operation of the motor 3065 to be initiated. Each lockout sensor switch 3136a-d may be configured to maintain an open (i.e., non-conductive) switch state or a closed (i.e., conductive) switch state responsive to the presence or absence, respectively, of a corresponding condition. Any of the corresponding conditions, if present when the instrument 10 is fired, may result in an unsatisfactory cutting and stapling operation and/or damage to the instrument 10. Conditions to which the lockout sensor switches 3136a-d may respond include, for example, (a) the absence of the staple cartridge 34 in the channel 22, (b) the presence of a spent (e.g., previously fired) staple cartridge 34 in the channel 22, and (c) an open (or otherwise insufficiently closed) position of the anvil 24 with respect to the channel 22. Other conditions to which the lockout sensor switches 3136a-d may respond, such as component wear, may be inferred based upon an accumulated number of firing operations produced by the instrument 3010. Accordingly, in various embodiments, if any of these conditions exists, the corresponding lockout sensor switches 3136a-d maintain an open switch state, thus preventing passage of the current necessary to initiate operation of the motor 3065. Passage of current by the lockout sensors 3136a-d is allowed, in various embodiments, only after all of the conditions have been remedied. It will be appreciated that the above-described conditions are provided by way of example only, and that additional lockout sensor switches for responding to other conditions detrimental to operation of the instrument 3010 may be provided. It will similarly be appreciated that for embodiments in which one or more of the above-described conditions may not exist or are of no concern, the number of lockout sensor switches may be fewer than that depicted.

As shown in FIG. 57, the lockout sensor switch 3136a may be implemented using a normally open switch configuration such that a closed switch state is maintained when the staple cartridge 34 is in a position corresponding to its proper receipt by the channel 22. When the staple cartridge 34 is not installed in the channel 22, or is installed improperly (e.g., mis-aligned), the lockout sensor switch 3136a maintains an open switch state. Lockout sensor switch 3136b may be implemented using a normally open switch configuration such that a closed switch state is maintained only when an unspent staple cartridge 34 (i.e., a staple cartridge 34 having a sled 3033 in the unfired position) is present in the channel 22. The presence of a spent staple cartridge 34 in the channel 22 causes the lockout sensor switch 3136b to maintain an open switch state. Lockout sensor switch 3136c may be implemented using a normally open switch configuration such that a closed switch state is maintained when the anvil 24 is in a closed position with respect to the channel 22. The lockout sensor switch 3136c may be controlled in accordance with a time delay feature wherein a closed switch state is maintained only after the anvil 24 is in the closed position for a pre-determined period of time.

Lockout sensor switch 3136d may be implemented using a normally closed switch configuration such that a closed switch state is maintained only when an accumulated number of firings produced by the instrument 3010 is less than a pre-determined number. The lockout sensor switch 3136d may be in communication with a counter 3139 configured for maintaining a count representative of the accumulated number of firing operations performed by the instrument 3010, comparing the count to the pre-determined number, and controlling the switch state of the lockout sensor switch 3136d based upon the comparison. Although shown separately in FIG. 57, it will be appreciated that counter 3139 may be integral with the lockout sensor switch 3136d so as to form a common device. Preferably, the counter 3139 is implemented as an electronic device having an input for incrementing the maintained count based upon the transition of a discrete electrical signal provided thereto. It will be appreciated that a mechanical counter configured for maintaining the count based upon a mechanical input (e.g., retraction of the firing trigger 3020) may be used instead. When implemented as an electronic device, any discrete signal present in the electrical circuit that transitions once for each firing operation may be utilized for the counter 3139 input. As shown in FIG. 57, for example, the discrete electrical signal resulting from actuation of the end-of-stroke sensor 3130 may be utilized. The counter 3139 may control the switch state of lockout sensor switch 3136d such that a closed switch state is maintained when the maintained count is less than a pre-determined number stored within the counter 3139. When the maintained count is equal to the pre-determined number, the counter 3139 causes the lockout sensor switch 3136d to maintain an open switch state, thus preventing the passage of current therethrough. It will be appreciated that the pre-determined number stored by the counter 3139 may be selectively adjusted as required. According to various embodiments, the counter 3304 may be in communication with an external display (not shown), such as an LCD display, integral to the instrument 3010 for indicating to a user either the maintained count or the difference between the pre-determined number and the maintained count.

According to various embodiments, the interlock circuit 3137 may comprise one or more indicators visible to the user of the instrument 3010 for displaying a status of at least one of the lockout sensor switches 3136a-d. More details regarding such indicators may be found in published U.S. Patent Application Publication No. 2007/0175956, entitled ELECTRONIC LOCKOUTS AND SURGICAL INSTRUMENT INCLUDING SAME, now U.S. Pat. No. 7,644,848, which is incorporated herein by reference in its entirety. This application also includes example mounting arrangements and configurations for the lockout sensor switches 3136a-d.

In the illustrated embodiment, when the lockout sensor switches 3136a-d collectively maintain a closed switch state, a single pole, single throw relay 3138 is energized. When the relay 3138 is energized, current flows through the relay 3138, through the run motor switch sensor 3110, and to the motor 3065 via a double pole, double throw relay 3140, thereby powering the motor 3065, allowing it to rotate in the forward direction. According to various embodiments, because the output of the relay 3138, once energized, maintains the relay 3138 in an energized state until relay 332 is energized, the interlock circuit 3137 will not function to prevent operation of the motor 3165 once initiated, even if one or more of the interlock sensor switches 3136a-d subsequently maintains an open switch state. In other embodiments, however, it may be necessary or otherwise desirable to connect the interlock circuit 3137 and the relay 3138 such that one or more the lockout sensor switches 3136a-d must maintain a closed switch state in order to sustain operation of the motor 3165 once initiated.

Rotation of the motor 3065 in the forward direction causes the ring to move distally and thereby de-actuate the stop motor sensor switch 3142 in various embodiments. Because the switch 3142 is normally closed, a solenoid 3141 connected to the switch 3142 may be energized. The solenoid 3141 may be a conventional push-type solenoid that, when energized, causes a plunger (not shown) to be axially extended. Extension of the plunger may operate to retain the closure trigger 18 in the retracted position, thus preventing the anvil 24 from opening while a firing operation is in progress (i.e., while the switch 3142 is not actuated). Upon de-energization of the solenoid 3141, the plunger is retracted such that manual release of the closure trigger 18 is possible.

When the actuation member portion reaches the distal most end of its stroke, the reverse motor switch 3130 will be activated, thereby closing the switch 3130 and energizing the relay 3132. This causes the relay 3132 to assume its energized state, which causes current to bypass the interlock circuit 3137 and run motor sensor switch 3110, and instead causes current to flow to both the normally-closed double pole, double throw relay 3140 and back to the motor 3065, but in a manner, via the relay 3140, that causes the motor 3065 to reverse its rotational direction. Because the stop motor sensor switch 3142 is normally closed, current will flow back to the relay 3132 to keep it energized until the switch 3142 opens. When the knife 32 is fully retracted, the stop motor sensor switch 3142 is activated, causing the switch 3142 to open, thereby removing power from the motor 3065, and de-energizing the solenoid 3141.

In the embodiment depicted in FIG. 57, a normally closed retraction switch 3143 is employed which interfaces with retraction trigger 3121 (not shown in FIG. 57). When retraction switch 3143 is activated, it opens to stop the flow of current to the motor 3065. In alternative embodiments (FIG. 57A), the normally closed retraction switch 3143 could be replaced with a variable resistor 3143' that interfaces with retraction trigger 3121. In such embodiment, when the retraction trigger 3121 is not depressed, the resistance of the variable resistor is minimal to allow maximum current to flow to the motor 3065. When depressed the resistance increases in proportion to the depressing force to reduce current to the motor. Such variable resistor may also be replaced with the retraction switch 3131 as described above (see FIG. 57B).

Accidental actuation prevention for a powered endocutter: With the introduction of powered systems that no longer limit the device function to the force capabilities of the user, inadvertent initiation of the firing cycle may become a much more prevalent issue. It will be increasing ease to "bump" the activation control and have the instrument begin firing thereby tripping the lockout of the cartridge or even "jamming" it on tissue, as the user is unaware it has already begun firing. Various lockout arrangements are disclosed in U.S. Pat. No. 7,644,848, entitled ELECTRONIC LOCKOUTS AND SURGICAL INSTRUMENT INCLUDING SAME to Swayze et al., the disclosure of which is herein incorporated by reference in its entirety. To eliminate this issue secondary unlock activator switches or buttons could be used to unlock the firing mechanism. This is much the same as the two switch systems used in the power saw industry as well as the military to protect against accidental actuation. The secondary switch can either release the lock on the firing trigger or merely energize the power to the control.

As mentioned above, in using a two-stroke motorized instrument, the operator first pulls back and locks the closure trigger 18. FIGS. 58 and 59 show one embodiment of a way to lock the closure trigger 18 to the pistol grip portion 3026 of the handle 3006. In the illustrated embodiment, the pistol grip portion 3026 includes a hook 3150 that is biased to rotate CCW about a pivot point 3151 by a torsion spring 3152. Also, the closure trigger 18 includes a closure bar 3154. As the operator draws in the closure trigger 18, the closure bar 3154 engages a sloped portion 3156 of the hook 3150, thereby rotating the hook 3150 upward (or CW in FIGS. 58 and 59) until the closure bar 3154 completely passes the sloped portion 3156 passes into a recessed notch 3158 of the hook 3150, which locks the closure trigger 18 in place. The operator may release the closure trigger 18 by pushing down on a slide button release 3160 on the back or opposite side of the pistol grip portion 3026. Pushing down the slide button release 3160 rotates the hook 3150 CW such that the closure bar 3154 is released from the recessed notch 3158. Other arrangements for releasably locking the closure trigger 18 are disclosed in U.S. Pat. No. 7,422,139 which has been herein incorporated by reference.

As can be seen in FIGS. 58 and 59, in various embodiments, a closure lock switch 3151 may be mounted in the hook 3150 such that that is activated only when the hook 3150 is latched in place. However, the closure lock switch 3151 may be mounted in the pistol grip portion 26 for activation by the closure trigger 18 when the closure trigger 18 is locked in position. In still other alternative embodiments, the closure lock switch 3151 is mounted to the end effector 12 such that it is activated only when the anvil or other movable portion is in the "closed" position. Regardless of the specific location of the closure lock switch 3151, in various embodiments, the closure lock switch 3151 is a normally open switch that will be closed upon locking of the closure trigger 18 or otherwise manipulating the end effector to a "closed" position.

FIG. 60 is a schematic diagram of an electrical circuit of the instrument 3010 according to various embodiments of the present invention illustrating the use of the closure lock switch 3151. As can be seen in that Figure, current will not be permitted to flow from the battery 3064 to the motor 3065 even if a cartridge is present unless the closure lock switch 3151 is closed. Thus, the motor 3065 cannot be operated unless the closure trigger is in the locked closed position which also reflects that the end effector is in the closed state.

Various embodiments may further include a start switch 3153 that must be activated by the surgeon before current will be permitted to flow from the battery 3064 to the other circuit components and ultimately to the motor 3065. Start switch 3153 is normally open and may be located at a convenient location on the handle 3006. See FIG. 61. Thus, in these embodiments, even if the end effector 12 contains a cartridge and the closure trigger 18 is locked in a closed position, current will not be permitted to flow to the motor 3065 until the start switch 3153 is closed by the surgeon. In alternative embodiments, the start switch 3153 may comprise a mechanical switch that prevents the firing trigger 3020 from being physically rotated toward the pistol grip portion unless the switch 3153 is moved to an actuated position.

Active adjustable staple height for a powered endocutter: Staple height that is adjustable to the tissue thickness and type has been pursued for many years. Most recently, U.S. patent application Ser. No. 11/231,456, filed Sep. 21, 2005, now U.S. Pat. No. 7,407,078 and U.S. patent application Ser. No. 11/540,735, filed Sep. 29, 2006, now U.S. Pat. No. 7,467,740, the disclosures of which are each hereby incorporated by reference in their respective entireties generally involve a flexible coupling member or supports that would allow the gap of the instrument to enlarge with loads induced by thicker tissue in the device. This "passive" variable staple height allows the thickness of the tissue to create larger staple forms.

With the introduction of a power source within the instrument this allows for the use of electricity to change the height of an internal element within the dynamic coupling element with would change the height of the staple "actively" by the surgeon or instrument setting the desired height. This internal element could be a shape memory material and the electricity changes its temperature and therefore allows it to change its physical height due to preset configuration. Another viable method would be the inclusion of an electro-active polymer (EAP) that through the introduction of an electric field allows it to change its height and width. Yet a third embodiment would be to utilize a traditional linear electrical stepper element that can ratchet a small adjustable screw element within the coupling beam that would adjust its height.

Figure 62:
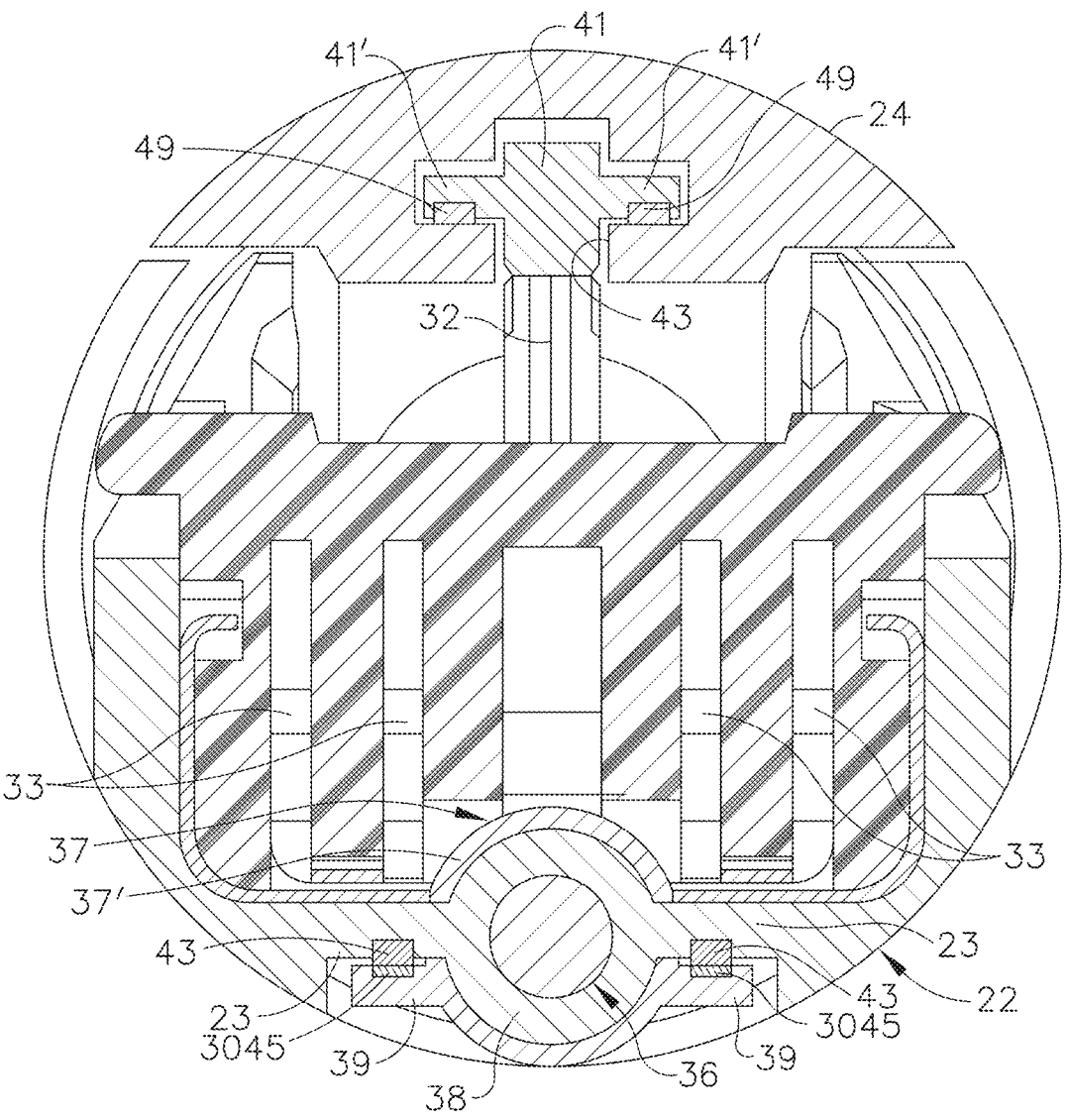
Figure 63:
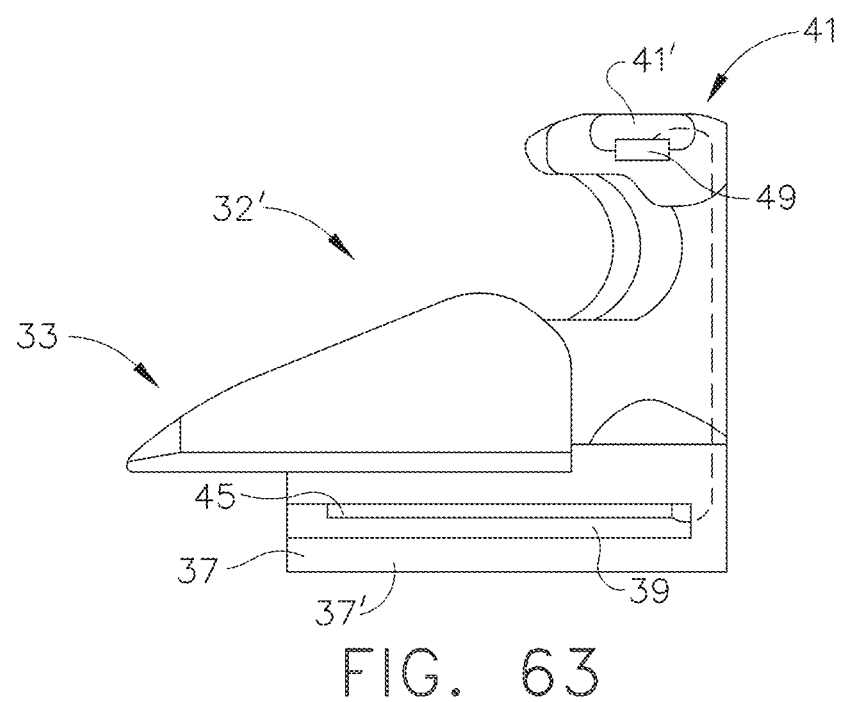

More specifically and with reference to FIGS. 62 and 63, an end effector 12 of various embodiments of the present invention is shown in cross-section with the anvil 24 in a closed or clamped position. As can be seen, the cutting instrument or knife 32 has a lower actuator portion 37 that has a threaded sleeve or nut portion 37' that is configured to threadably engage the helical screw shaft 36. In addition, a fin 39 protrudes laterally from each lateral side of the nut portion 37 to confront corresponding slide portions 3023 of the channel 22. As can also be seen in FIG. 62, the knife 32 has an upper actuator portion 41 that is sized to be received within a longitudinal T-shaped slot 43 in the anvil 24. As can be seen in FIG. 62, a pair of upper retainer pins 41' protrude laterally from each side of the upper actuator portion 41 of the knife 32. Each upper retainer pin 41' is configured to extend into a corresponding portion of the T-shaped slot 43 provided in the anvil 24. Thus, as the knife 32 is driven distally through the end effector 12, the fins 39 and the retainer pins 41' serve to limit the amount of space between the anvil 24 and the cartridge 34 to a maximum amount of predetermined space.

Various embodiments of the present invention are provided with means for adjusting the amount of space between the anvil 24 and the cartridge 34 installed within the channel 22. For example, in some embodiments, each fin 39 supports a sled contact 3045 for sliding contact with corresponding electrical contacts 47 that are mounted within each slide portion 3023 of the channel 22. The electrical contacts 47 are elongated and extend within the channel 22 so that the sled contacts 3045 are always on contact with their corresponding electrical contact 47 as the knife 32 is driven within the channel 22. Electrical contacts 47 are connected to the power source or battery 3064 and are configured to receive current therefrom when the motor 3065 is powered to drive the knife 32 distally. Also in certain embodiments, an electrically responsive height adjustment member 49 is mounted to each retainer pin 41' as shown in FIG. 62. The height adjustment members 49 are electrically coupled to the sled contacts 3045 to receive electrical current therefrom. In various embodiments, the height adjustment members 49 may comprise shape memory material that, when electrified, changes its physical height due to a preset configuration. Thus, depending upon the amount of current received, the height adjust member members 49 may expand and force the anvil 24 towards the cartridge 34 to thereby reduce the amount of space therebetween. The amount that such material is proportional to the amount of current received and is known. A control circuit (not shown) may be employed to control the amount of expansion and hence the amount of space between the anvil 24 and the cartridge 34. In other embodiments, the height adjustment material comprises an electro-active polymer (EAP) that is retained within a pocket in the pin 41 or is otherwise attached thereto.

Figure 64:
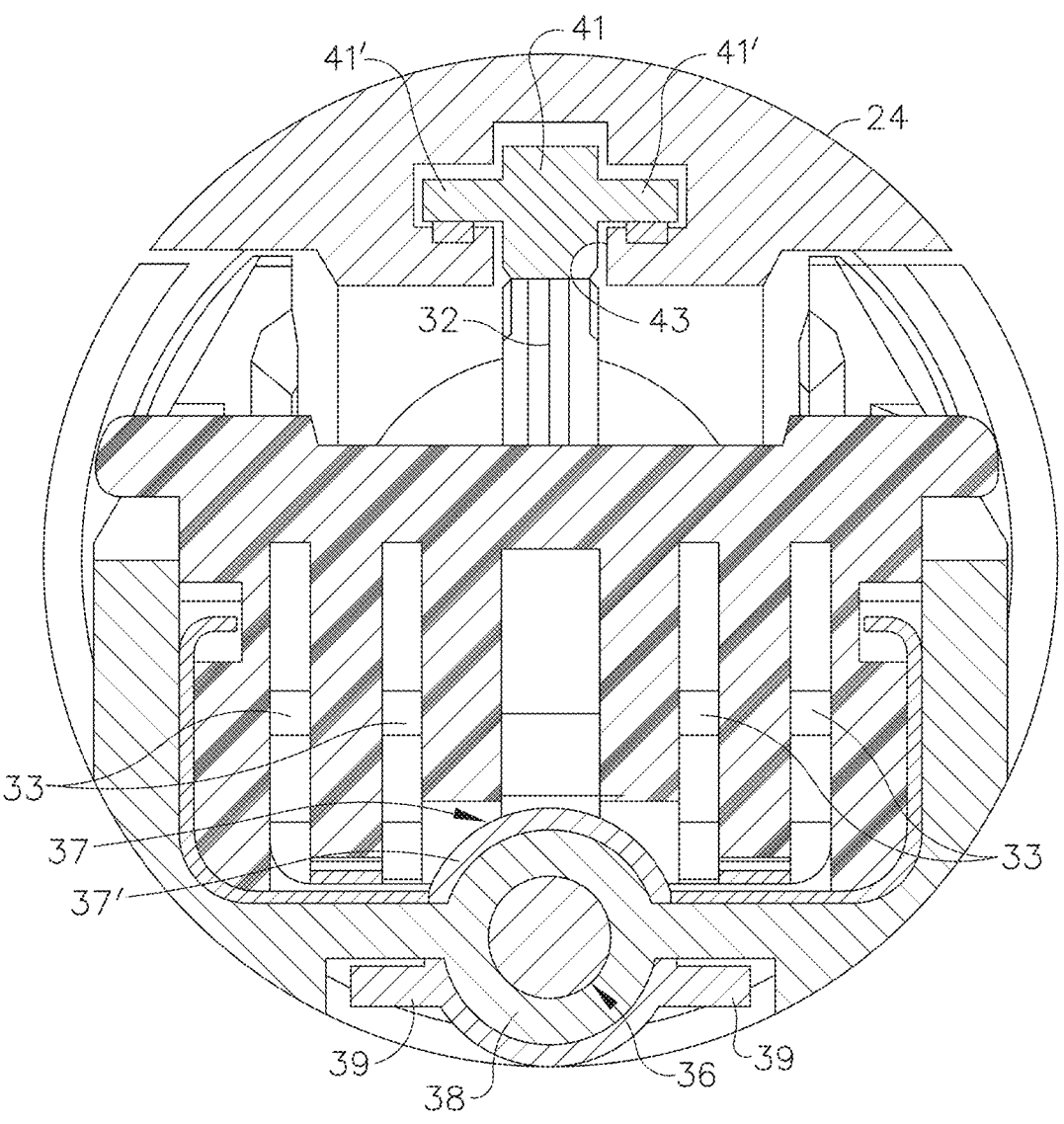

FIG. 64 illustrates another embodiment that is similar to the embodiment depicted in FIG. 62. However, in this embodiment, the height adjustment members 49 are mounted in the anvil 24 and receive current from the power source through conductors attached directly thereto. Thus, in this embodiment, the contacts 43 and 3045 as described above are not needed.

Figure 65:
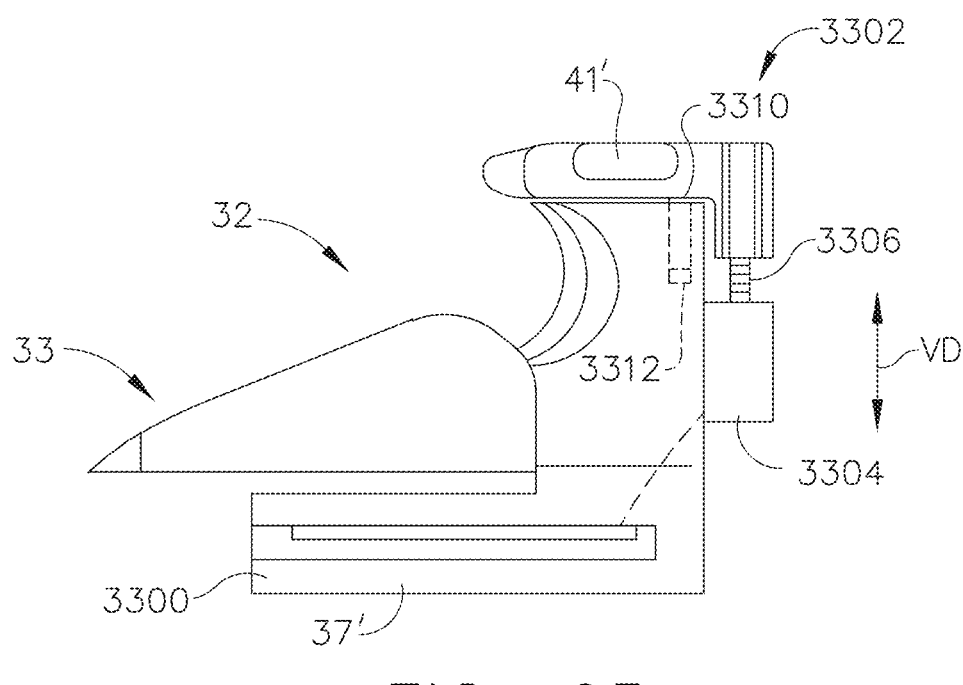

FIG. 65 illustrates an alternative knife assembly 32' that is substantially identical to the knife assembly 32 described above, except that the retainer pins 41' are mounted to a separate upper actuator portion 3302 that is selectively movable in a vertical direction "VD" relative to a lower portion 3300 of the knife assembly 32'. A second motor 3304 may be mounted to the lower portion 3300 and have a lead screw 3306 that threadably engages a nut portion 3308 of the upper retainer portion 3302. The upper retainer portion has a "T"-shaped tongue portion 3310 that slidably extends into a correspondingly shaped slot 3312 in the lower portion 3300 to prevent rotation of the upper retainer portion 3302 relative to the lower retainer portion 3300 while permitting the upper retainer portion 3302 to move vertically relative thereto. Thus, the distance between the upper and lower retainer portions 3302, 3300 may be adjusted by powering the second motor 3304. Accordingly, if the surgeon wants to reduce the amount of space between the anvil 24 and the cartridge 34, second motor 3304 is powered to rotate in a first direction to draw the upper retainer portion 3302 towards the lower retainer portion 3300. If however, the surgeon desires to increase the amount of space between the anvil 24 and the cartridge 34, the second motor 3304 is rotated in an opposite direction.

Various embodiments of the present invention include end-effector illumination methods and methods for illuminating the surgical site when employing a powered endocutter. Currently when the end-effector is in or near its deployment position it is sometimes difficult for the surgeon to visualize the treatment site as there are shadows cast by adjacent structures as well as the end-effector may even be behind another structure entirely. FIG. 66 illustrates in general form, a distal end 3402 of a surgical stapler 3400 of various embodiments of the present invention which includes an anvil 3404, a cartridge body 3406, and channel 3408. As seen from that Figure, an additional light source 3410 may be positioned on the end of the cartridge body 3406 to illuminate tissue 3401. This light source 3410 could be any combination of practical means that convert electrical energy to light including but not limited to semiconductor (such as LED), a conventional incandescent or filament bulb, electroluminescent or laser that may be powered from a battery supported in the instrument handle or in other embodiments, powered by alternating current. Such arrangements would allow the surgeon to not only light up the treatment site directly, they could allow for backlighting of structures to see the internal components like vasculature and facilitate the use of a laser pointer through a traditional scope to point out areas of interest to others.

In various embodiments, one or more contacts 3420 are provided on the back of the cartridge body 3406 that are configured to engage contacts 3422 within the channel 3408. See FIG. 67. This would allow the surgeon to energize the light 3410 as needed by energizing contact set via a switch positioned on the handle 3430. This switch could even have variable intensity as the one described in could control the actuation speed of the main, device. Other lighting arrangements for lighting the end of an anvil attached to a circular surgical stapler are disclosed in U.S. Pat. No. 7,918,377, entitled SURGICAL STAPLING INSTRUMENT WITH APPARATUS FOR PROVIDING ANVIL POSITION FEEDBACK, the entire disclosure of which is hereby incorporated by reference.

U.S. Pat. No. 8,708,213, entitled SURGICAL INSTRUMENT HAVING A FEEDBACK SYSTEM, the entire disclosure of which is hereby incorporated by reference, further discloses in FIGS. 45-47 of that Publication output displays that could show among other this position feedback of the end-effector, lockout status, number of firings etc. This would minimize one of the more difficult issues for the user, which is the identification of the status of a device, especially the lockout status of the device without actuating the device. An additional feedback that would be helpful for the user would be immediate feedback as to the status of the cartridge when it is loaded. As in the above application it could be rolled up into the lockout indication on the handle 3430. An indicator 3432 (such as an LED, glass bulb, LCD, sonic enunciator, vibrator, etc.) could solely be associated with the status of a cartridge lockout means or mechanism such that it providing this information to the surgeon. This LED could be located on the handle 3430. See FIG. 69. Alternatively an indicator 3434 could be located near the distal end 3402 which would provide immediate information to the surgeon and loader if the cartridge is "good to go" or not. See FIG. 68. This can be accomplished with a switch or set of contacts associated directly with the mechanical lockout. The switch or contacts complete a circuit such that the indicator provides appropriate information. This completed contact set could be through a conductive element within the sled (part 33 in U.S. Patent Application Publication No. US 2007/0175958, now U.S. Pat. No. 7,766,210) and the two contacts could be in the proximal position of the channel (part 22). Another way to detect lockout status is indirectly through instrument status (example I: loaded cartridge and no attempt to fire would indicate lockout is not engaged; example 2: fired instrument and no new cartridge installed would indicate lockout is engaged; etc.). Another embodiment would be to place the LED or visual indication cue on the cartridge itself. When the cartridge is snapped into place it creates a contact that supplies the cartridge with power. Should the cartridge be fired not only does the mechanical lockout stop the advancement of the knife the cartridge circuit light up the LED on the cartridge informing the surgeon on the scope monitor that the cartridge is locked out. This could be further expanded by placing a small battery or other charge accumulator within the cartridge itself to eliminate the need for a power connection to the main device. Also the cartridge circuit could be set to light the lockout light whenever the device is closed to inform the user there is a spent cartridge in the device.

Indication feedback for powered articulation and cartridge color: Indicating the type of cartridge installed (color) and angle of articulation is considered useful to the surgeon. The indication of articulation angle could be indicated in several ways including numerically or graphically as in an arc of LEDs. The location of this indication could be on the handle in a convenient location or on the shaft of the device just proximal to the end-effector. The end-effector feedback could be passive or active. The active would light up additional LEDs to show the angle. The passive could just show a half pie lighted up so the surgeon could intuit how articulated the end-effector is. As we further explore the surgical procedures it becomes more and more obvious that the surgeon's eyes need to be on the surgical site not on the handle of the instrument. We also begin to understand the surgeon's need for complete status feedback from the device. Articulation angle could be illuminated as part of the articulation joint itself. With lights, LEDs, etc. denoting the differing angle or even a small LCD denoting angle in degrees. This would allow the surgeon to have some feedback on the angle off of straight so he/she can easily navigate back to this angle after removal and reinsertion. Another issue is "obvious" indication of what color cartridge is in the device. This can be accomplished by a color coded light array on either the end-effector or the cartridge. This information could also be transmitted back to the handle to display a "redundant" display to assure there is minimal confusion as to what cartridge is in the jaws. Another improvement could include a small leaf spring contact connected to the proximal deck of the cartridge that indicates if a minimum tissue pressure has been achieved within the jaws. This minimum pressure would at the very least indicate if a thick tissue cartridge is being used in thin tissue applications, as it would not light if insufficient tissue pressure on the deck were present.

There is a possible need of a method for the introduction of non-sterile battery packs (possibly with the electronics integral to the battery pack if programmable logic becomes a key customer need). A patent already exists within the orthopedic drill industry for the insertion of a non-sterile battery pack within a separately sterilized re-useable device. This innovation is intended to improve that concept by utilizing the disposable device sterile packaging to protect the sterility of the instrument during the insertion of the non-sterile battery pack. A further improvement would be the inclusion of a "hatch" door designed within the instrument and closable after the pack has been inserted but before the device is removed from the final sterile packaging. This hatch would then "contain" the non-sterile battery that could contaminate the sterile surgical field. The method here would be to include an additional layer of packaging that would have a perforated area that the battery could be pushed through, either rupturing the extra layer and allowing the battery through or going with the electrode set of the battery only to be ruptured by the exposable pin tips of the battery at complete insertion. An alternative of this would be to have the internal terminals of the gun (deep inside the battery protection cavity) rupture the sterile barrier and seat within pinholes in the battery pack. The hatch could then be closed through the sterile pack sealing the system. The gun could then be handed into the sterile field normally as any sterile device could.

Position Locator Embodiments/Linear encoder and load control of motor parameters: U.S. Pat. Nos. 6,646,307 and 6,716,223 disclose the mechanisms for the measurement of rotation and related torque to control motor parameters and optimizing of those parameters based on identification of end-effector configurations and loading. U.S. Pat. No. 7,766, 210 shows a method through the use of a threaded length of the primary shaft in FIGS. 8-13 how this type of linear motion control could be used to control the trigger location. The same type of method could be used for electronic linear control methods. The end-effector could identify its length and type mechanically by depressing at least one spring biased plunger, which could identify to the handle the type, and length it would allow the motor to run. The motor rotation could be converted from rotary motion to linear rack or cable motion, which could then be used to adjust motor voltage, current, and speed to affect the desired linear motion of the control slide. The control slide could then be directly coupled to the knife drive motion. This control slide could have discrete or continuous "stop" locations that the plunger identifier marks as the max "go to" linear displacement before retraction Identification of modular reloads with linear drive: A useful feature for a surgical instrument is the ability to identify which end-effector has been attached to the instrument. In the case of a powered surgical stapler, several different types of end-effectors could be attached. Additionally, a type of end-effector may have at least one function and/or feature that is selectively utilized or enabled. Disclosed are means for identifying which end-effector is attached. Note that the "type" of end-effector referenced below is not limited to mechanical, pneumatic or hydraulically coupled end-effectors. The instrument may take different actions, adjust operating parameters, indicate available functions etc. as a result of detecting this end effector.

The end-effector has an electrical connection that is made when it is attached to the instrument. The instrument communicates with the end-effector and reads at least one of several types of signals. A switch position or contact position indicates which type of end-effector is present. A passive element is measured for impedance and the result indicates which type of end-effector is present.

The end-effector has a radio frequency link to the instrument and data is transferred in at least one direction between the end-effector and the instrument.

The end-effector has an acoustic link to the instrument and data is transferred in at least one direction between the end-effector and the instrument.

The end-effector has an optical link to the instrument and data is transferred in at least one direction between the end-effector and the instrument.

The end-effector has mechanical link that engages elements (such as switches or contacts) in the instrument that identify it and thereby data is transferred in at least one direction between the end-effector and the instrument.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, although the embodiments described above have advantages for an endoscopically employed surgical severing and stapling instrument 10, a similar embodiments may be used in other clinical procedures. It is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to a surgical instrument for use only in conjunction with an endoscopic tube (i.e., trocar). On the contrary, it is believed that the present invention may find use in any procedure where access is limited to a small incision, including but not limited to laparoscopic procedures, as well as open procedures.

Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical stapling system, comprising:
an end effector comprising a first jaw and a second jaw, wherein the first jaw is movable from an open position towards a clamped position;
a motor-driven firing bar movable when a firing motion is applied thereto;
a sensor to monitor a stapling condition; and
a control circuit to:
receive a sensor signal from the sensor indicative of the stapling condition;
initiate a timer based on the sensor signal; and
transmit a firing signal to generate the firing motion based on the timer satisfying a threshold.

2. The surgical stapling system of claim 1, wherein the threshold is selected to delay the firing motion to stabilize patient tissue.

3. The surgical stapling system of claim 2, further comprising a display, wherein the control circuit is to cause the display to indicate that the motor-driven firing bar is being prevented from moving through the firing motion before the timer satisfies the threshold.

4. The surgical stapling system of claim 3, wherein the display comprises a light emitting diode (LED) display.

5. The surgical stapling system of claim 4, and wherein one of the first jaw and the second jaw is configured to removably receive a staple cartridge comprising a plurality of ejectable staples.

6. The surgical stapling system of claim 5, further comprising the staple cartridge, wherein the firing motion of the motor-driven firing bar is to eject the plurality of ejectable staples from the staple cartridge.

7. The surgical stapling system of claim 6, further comprising a motor to generate the firing motion, wherein the control circuit is further to cause the motor to generate the firing motion based on the timer satisfying the threshold.

8. The surgical stapling system of claim 7, wherein the timer comprises an on-delay timer.

9. The surgical stapling system of claim 1, wherein the threshold corresponds to a pre-set time delay.

10. The surgical stapling system of claim 1, wherein the threshold corresponds to a selectively adjustable delay.

11. The surgical stapling system of claim 1, wherein the threshold comprises a force threshold.

12. A surgical stapling system, comprising:
an end effector comprising a first jaw and a second jaw, wherein the first jaw is movable from an open position towards a clamped position, and wherein one of the first jaw and the second jaw is configured to removably receive a staple cartridge comprising a plurality of staples;
a motor-driven firing driver movable when a firing motion is applied thereto;
a force sensor; and
a control circuit to:
receive a sensor signal from the force sensor;
initiate a timer based on the sensor signal; and
transmit a firing signal to generate the firing motion based on the timer satisfying a threshold.

13. The surgical stapling system of claim 12, further comprising the staple cartridge, wherein the firing motion of the motor-driven firing driver is to eject the plurality of staples from the staple cartridge.

14. The surgical stapling system of claim 13, further comprising a motor to generate the firing motion, wherein the control circuit is further to cause the motor to generate the firing motion based on the timer satisfying the threshold.

15. The surgical stapling system of claim 14, wherein the threshold corresponds to a delay for stabilizing patient tissue.

16. The surgical stapling system of claim 15, wherein the timer comprises an on-delay timer.

17. The surgical stapling system of claim 15, wherein the threshold corresponds to a pre-set time delay.

18. The surgical stapling system of claim 15, wherein the threshold corresponds to a selectively adjustable delay.

19. The surgical stapling system of claim 12, further comprising a display, wherein the control circuit is to cause the display to indicate that a status of the timer.

20. The surgical stapling system of claim 12, wherein the sensor signal corresponds to a clamping force.

* * * * *